(12) United States Patent
Oost et al.

(10) Patent No.: US 9,346,794 B1
(45) Date of Patent: May 24, 2016

(54) SUBSTITUTED 4-PYRIDONES AND THEIR USE AS INHIBITORS OF NEUTROPHIL ELASTASE ACTIVITY

(71) Applicant: Boehringer Ingelheim International GmbH, Ingelheim am Rhein (DE)

(72) Inventors: Thorsten Oost, Biberach an der Riss (DE); Dennis Fiegen, Biberach an der Riss (DE); Christian Gnamm, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/981,999

(22) Filed: Dec. 29, 2015

Related U.S. Application Data

(63) Continuation of application No. 13/971,378, filed on Aug. 20, 2013, now abandoned.

(30) Foreign Application Priority Data

Aug. 23, 2012 (EP) ..................... 12181542

(51) Int. Cl.
| | | |
|---|---|---|
| *A61K 31/54* | (2006.01) | |
| *A61K 31/50* | (2006.01) | |
| *A61K 31/501* | (2006.01) | |
| *A61K 38/00* | (2006.01) | |
| *A61P 11/06* | (2006.01) | |
| *A61P 17/00* | (2006.01) | |
| *A61P 29/00* | (2006.01) | |
| *C07D 215/00* | (2006.01) | |
| *C07D 213/62* | (2006.01) | |
| *C07D 417/04* | (2006.01) | |
| *C07D 213/82* | (2006.01) | |
| *C07D 401/04* | (2006.01) | |
| *C07D 413/04* | (2006.01) | |
| *C07D 405/04* | (2006.01) | |

(52) U.S. Cl.
CPC ............ *C07D 417/04* (2013.01); *C07D 213/82* (2013.01); *C07D 401/04* (2013.01); *C07D 405/04* (2013.01); *C07D 413/04* (2013.01)

(58) Field of Classification Search
None
See application file for complete search history.

(56) References Cited

U.S. PATENT DOCUMENTS

| 4,844,732 A | 7/1989 | Goto et al. |
|---|---|---|
| 2006/0035938 A1 | 2/2006 | Bladh et al. |
| 2012/0149735 A1 | 6/2012 | Millet et al. |

FOREIGN PATENT DOCUMENTS

| EP | 1562902 A1 | 8/2005 |
|---|---|---|
| EP | 2261211 A1 | 12/2010 |
| WO | 2006098683 A1 | 9/2006 |
| WO | 2009094417 A1 | 7/2009 |

OTHER PUBLICATIONS

International Search Report, form PCT/ISA/210, and Written Opinion, form PCT/ISA/237, for corresponding application PCT/EP2013/067425, date of mailing Oct. 2, 2013.

*Primary Examiner* — Jeffrey S Lundgren
*Assistant Examiner* — Tori M Strong
(74) *Attorney, Agent, or Firm* — Michael P. Morris; Edward S. Lazer

(57) ABSTRACT

This invention relates to substituted 4-pyridones of formula 1

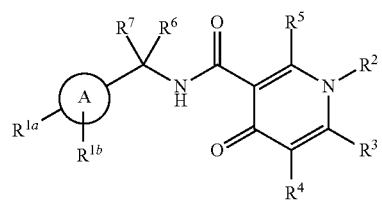

and their use as inhibitors of neutrophil elastase activity, pharmaceutical compositions containing the same, and methods of using the same as agents for treatment and/or prevention of pulmonary, gastrointestinal and genitourinary diseases, inflammatory diseases of the skin and the eye and other auto-immune and allergic disorders, allograft rejection, and oncological diseases.

6 Claims, No Drawings

SUBSTITUTED 4-PYRIDONES AND THEIR USE AS INHIBITORS OF NEUTROPHIL ELASTASE ACTIVITY

FIELD OF THE INVENTION

This invention relates to substituted 4-pyridones and their use as inhibitors of neutrophil elastase activity, pharmaceutical compositions containing the same, and methods of using the same as agents for treatment and/or prevention of pulmonary, gastrointestinal and genitourinary diseases, inflammatory diseases of the skin and the eye and other auto-immune and allergic disorders, allograft rejection, and oncological diseases.

BACKGROUND INFORMATION

The following references describe neutrophil elastase inhibitors with a 2-pyridone central core: WO04043924, WO05026123, WO05026124, WO06098683, WO06098684, WO07129962, WO10094964, WO11039528.

The following references describe neutrophil elastase inhibitors with a 2-pyrazinone central core: WO07129963, WO09061271, WO09058076, WO11110852.

For a review on various inhibitors of neutrophil elastase see: P. Sjö (*Future Med. Chem.* 2012, 4, 651-660).

BRIEF SUMMARY OF THE INVENTION

Neutrophil elastase is a 29 kDa serine protease. It is expressed in bone marrow precursor cells, stored in the granula of peripheral blood granulocytes at high concentrations and it is released upon cellular activation. To the substrates of NE belong major elements of the extracellular matrix: elastin, fibronectin, laminin, collagen and proteoglycans. Neutrophil elastase activity leads to ECM degradation, increases migration and chemotaxis of monocytes and vascular smooth muscle cells and directly affects components of the coagulation and fibrinolytic pathways (PAI-1 and TFPI). Increased activity of neutrophil elastase is associated with chronic inflammatory and fibrotic diseases of several organs. Inhibitors of neutrophil elastase will therefore have an important role for the treatment of different diseases like COPD, fibrosis, cancer and others.

The compounds according to the present invention, including the physiologically acceptable salts, are effective as inhibitors of neutrophil elastase and exhibit favourable inhibitory potency, as determined by the half maximal inhibitory concentration ($IC_{50}$), in an enzymatic inhibition assay.

Some compounds according to the present invention, including the physiologically acceptable salts, exhibit favourable inhibitory potency, as determined by the half maximal effective concentration ($EC_{50}$), in a plasma or whole-blood assay, for instance as described in T. Stevens et al., J. Pharm. Exp. Ther. 339, 313-320 (2011).

Some compounds according to the present invention, including the physiologically acceptable salts, exhibit favourable in vivo potency, as determined, for example, by the half maximal effective dose ($ED_{50}$), in models of human neutrophil elastase-induced lung injury in mice, rat or hamster, for instance as described in Tremblay et al. (*Chest* 2002, 121, 582-588) or T. Stevens et al. (*J. Pharm. Exp. Ther.* 2011, 339, 313-320).

Some compounds according to the present invention, including the physiologically acceptable salts, exhibit favourable metabolic stability in an in vitro microsomal assay for metabolic stability as described in E. Kerns & L. Di, Drug-like properties: concepts, structure design and methods: from ADME to toxicity optimization, Elsevier, 1$^{st}$ ed, 2008, chapter 29 and references therein.

Some compounds according to the present invention, including the physiologically acceptable salts, exhibit favourable metabolic stability in an in vitro hepatocytes assay for metabolic stability as described in E. Kerns & L. Di, Drug-like properties: concepts, structure design and methods: from ADME to toxicity optimization, Elsevier, 1$^{st}$ ed, 2008, chapter 29 and references therein.

An improved metabolic stability in an in vitro test system is expected to translate into a reduced in vivo clearance (CL), because the metabolic conversion in the liver is reduced. Based on the pharmacokinetic equation $CL/F_{oral}=Dose/AUC$ ($F_{oral}$: oral bioavailability, AUC: area under the curve), a reduced in vivo clearance is expected lead to higher dose-normalized systemic exposure (AUC) of the drug.

Some compounds according to the present invention, including the physiologically acceptable salts, exhibit favourable permeability in an in vitro Caco-2 cell layer method for permeability as described in E. Kerns & L. Di, Drug-like properties: concepts, structure design and methods: from ADME to toxicity optimization, Elsevier, 1$^{st}$ ed, 2008, chapter 26 and references therein. For an oral drug, improved permeability is expected to translate into a higher fraction of the drug absorbed in the intestinal tract, thus, resulting in higher dose-normalized systemic exposure (AUC).

Comparatively higher dose-normalized systemic exposure (AUC) can be advantageous in several ways: (1) If a certain systemic exposure (AUC) needs to be achieved for efficacy, the drug can be dosed in a lower amount. Lower dosages have the advantages of lower drug load (parent drug and metabolites thereof) for the patient causing potentially less side effects, and lower production costs for the drug product. (2) Comparatively higher dose-normalized systemic exposure (AUC) can lead to increased efficacy or prolonged duration of action of the drug when the same dose is applied.

Some compounds according to the present invention, including the physiologically acceptable salts, exhibit favourable metabolic stability and favourable permeability. Accordingly, some compounds of the present invention are expected to exhibit favourable pharmacokinetic (PK) properties, in particular favourable systemic exposure (area under the curve, AUC).

Some compounds according to the present invention, including the physiologically acceptable salts, exhibit favourable pharmacokinetic (PK) properties. The PK properties can be determined in pre-clinical animal species, for example mouse, rat, dog, guinea pig, mini pig, cynomolgus monkey, rhesus monkey. The PK properties of a compound can be described, for example, by the following parameters: Mean residence time (MRT), elimination half-live ($t_{1/2}$), volume-of-distribution ($V_D$), area under the curve (AUC), clearance (CL), bioavailability after oral administration ($F_{oral}$).

DETAILED DESCRIPTION OF THE INVENTION

Compounds of formula 1

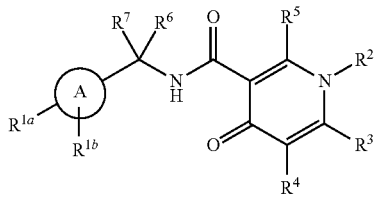

wherein

A is phenyl or a five- or six-membered, aromatic heteroring, wherein one, two or three elements are replaced by an element selected independent from each other from the group consisting of N, $(O^-)$—$N^+$, O and S;

$R^{1a}$ is

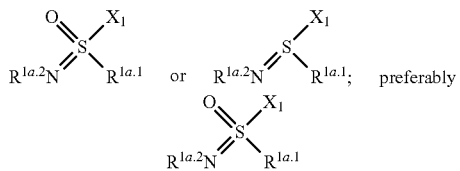

$R^{1a.1}$ is $C_{1-4}$-alkyl-, $C_{3-6}$-cycloalkyl-, $C_{1-4}$-haloalkyl-, $H_2N$—, $C_{1-4}$-alkyl-NH—, $C_{3-6}$-cycloalkyl-NH—, $(C_{1-4}$-alkyl$)_2N$—, $(C_{3-6}$-cycloalkyl$)(C_{1-4}$-alkyl$)N$—, azetidinyl, pyrrolidinyl, piperidinyl, morpholinyl, piperazinyl, piperazinyl-$C_{1-4}$-alkyl-, $C_{1-4}$-alkyl-O—NH—, $(C_{1-4}$-alkyl-O$)(C_{1-4}$-alkyl$)N$—;

$R^{1a.2}$ is H, NC—, $O_2N$—, $C_{1-4}$-alkyl-$SO_2$—, aryl-$SO_2$—, (aromatic heteroring)-$SO_2$—, $C_{1-4}$-alkyl-O—(O)C—, $C_{1-4}$-alkyl-(O)C—, $C_{3-6}$-cycloalkyl-(O)C—, $H_2N$—(O)C—, $C_{1-4}$-alkyl-NH—(O)C—, $C_{3-6}$-cycloalkyl-NH—(O)C—, $(C_{1-4}$-alkyl$)_2N$—(O)C—, $(C_{3-6}$-cycloalkyl$)(C_{1-4}$-alkyl$)N$—(O)C—, azetidinyl-(O)C—, pyrrolidinyl-(O)C—, piperidinyl-(O)C—, morpholinyl-(O)C—, piperazinyl-(O)C—, piperazinyl-$C_{1-4}$ alkyl-(O)C—, $C_{1-4}$-alkyl-, $C_{3-6}$-cycloalkyl-, $C_{1-4}$-haloalkyl-, aryl, heteroaryl;

$R^{1b}$ is H, $C_{1-4}$-alkyl-, $C_{3-6}$-cycloalkyl-, $C_{1-4}$-haloalkyl- or halogen;

or $R^{1a}$ and $R^{1b}$ are together $C_{2-4}$-alkylene forming a carbocyclic heteroring;

$R^2$ is $C_{1-6}$-alkyl or a residue selected from the group consisting of $C_{3-6}$-cycloalkyl-, wherein one element of the ring is optionally replaced by O; phenyl-$C_{1-4}$-alkyl-, (aromatic heteroring)-$C_{1-4}$-alkyl- and a five- or six-membered, aromatic heteroring, wherein one, two or three elements are replaced by an element selected independent from each other from the group consisting of N, O and S; each element of one of the rings optionally substituted with one or two groups selected from $C_{1-4}$-alkyl-, $C_{3-6}$-cycloalkyl-, halogen, $C_{1-4}$-haloalkyl-, $C_{1-4}$-alkyl-O—, $C_{1-4}$-alkyl-$SO_2$— or NC—;

$R^3$ is H or $C_{1-4}$-alkyl-;

is $R^4$ is phenyl, a five- or six-membered, aromatic heteroring containing one, two or three atoms selected from N, O and S; each ring optionally substituted with one or two residues selected independently from each other from the group consisting of $C_{1-4}$-alkyl-, $C_{3-6}$-cycloalkyl-, halogen or $C_{1-4}$-haloalkyl-;

$R^5$ is H, $C_{1-4}$-alkyl-, $C_{1-4}$-haloalkyl-, halogen;

$R^6$ is H or $C_{1-4}$-alkyl-;

$R^7$ is H or $C_{1-4}$-alkyl-;

or $R^6$ and $R^7$ are forming together a $C_{2-5}$-alkylene, wherein one element of the formed ring is optionally replaced by O;

or a pharmaceutically acceptable salt thereof.

PREFERRED EMBODIMENTS

Preferred are the above compounds of formula 1, wherein A is phenyl or pyridinyl; preferably phenyl; $R^{1a}$ is

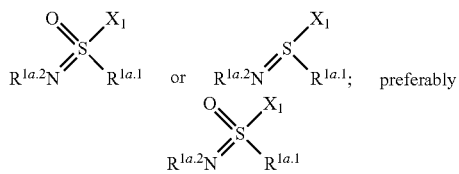

$R^{1a.1}$ is $C_{1-4}$-alkyl-, $C_{3-6}$-cycloalkyl-, $C_{1-4}$-alkyl-NH— or $(C_{1-4}$-alkyl$)_2N$—, preferably $C_{1-4}$-alkyl- or $C_{3-6}$-cycloalkyl-;

$R^{1a.2}$ is H, methyl, NC—, Me-$SO_2$—;

$R^{1b}$ is H, methyl, F, preferably H;

and $R^2$, $R^3$, $R^4$, $R^5$, $R^6$, $R^7$ have the above given meaning; or a pharmaceutically acceptable salt thereof.

Preferred are the above compounds of formula 1, wherein A is phenyl or pyridinyl; preferably phenyl; $R^{1a}$ is

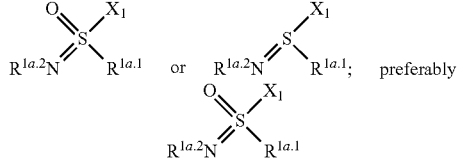

$R^{1a.1}$ is methyl, ethyl, i-propyl, cyclopropyl;

$R^{1a.2}$ is NC—;

$R^{1b}$ is H;

and $R^2$, $R^3$, $R^4$, $R^5$, $R^6$, $R^7$ have the above given meaning; or a pharmaceutically acceptable salt thereof.

Preferred are the above compounds of formula 1, wherein $R^3$ is methyl;

and A, $R^{1a}$, $R^{1b}$, $R^2$, $R^4$, $R^5$, $R^6$, $R^7$ have the above given meaning; or a pharmaceutically acceptable salt thereof.

Preferred are the above compounds of formula 1, wherein $R^4$ is selected from a group consisting of

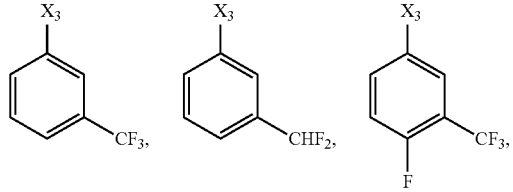

-continued

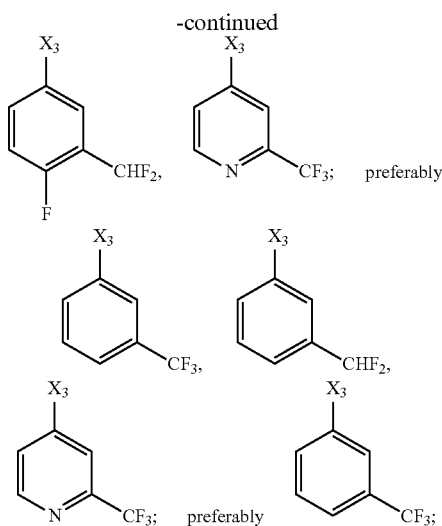

and A, $R^{1a}$, $R^{1b}$, $R^2$, $R^4$, $R^5$, $R^6$, $R^7$ have the above given meaning; or a pharmaceutically acceptable salt thereof.

Preferred are the above compounds of formula 1, wherein
$R^5$ is H;
$R^6$ is H;
$R^7$ is H;
and A, $R^{1a}$, $R^{1b}$, $R^2$, $R^3$, $R^4$, have the above given meaning; or a pharmaceutically acceptable salt thereof.

Preferred are the above compounds of formula 1, wherein
A is phenyl or pyridinyl;
$R^{1a}$ is

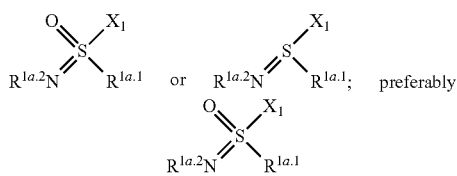

$R^{1a.1}$ is $C_{1-4}$-alkyl-;
$R^{1a.2}$ is NC—;
$R^{1b}$ is H;
$R^2$ is $C_{1-6}$-alkyl or a residue selected from the group consisting of $C_{3-6}$-cycloalkyl-, phenyl-$C_{1-4}$-alkyl- and a five- or six-membered, aromatic heteroring containing one or two nitrogen atoms, each of the above rings optionally substituted with $C_{1-4}$-alkyl-, halogen or NC—;
$R^3$ is methyl;
$R^4$ is phenyl, a five- or six-membered, aromatic ring containing one or two nitrogen atom, each ring optionally substituted with one or two residues selected independently from each other from the group consisting of $C_{1-4}$-alkyl-, halogen or $C_{1-4}$-haloalkyl-;
$R^5$ is H;
$R^6$ is H;
$R^7$ is H;
or a pharmaceutically acceptable salt thereof.

Preferred are the above compounds of formula 1, wherein
A is phenyl or pyridinyl;
$R^{1a}$ is

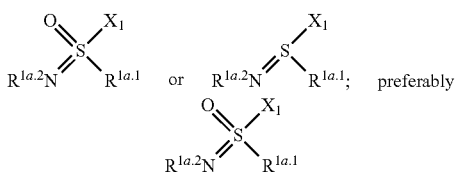

$R^{1a.1}$ is $C_{1-4}$-alkyl-;
$R^{1a.2}$ is NC—;
$R^{1b}$ is H;
$R^2$ is $C_{1-6}$-alkyl or a residue selected from the group consisting of $C_{3-6}$-cycloalkyl-, phenyl-$C_{1-4}$-alkyl- and a five-membered, aromatic ring containing two nitrogen atoms; each optionally substituted with methyl or NC—;
$R^3$ is methyl;
$R^4$ is phenyl or a six-membered, aromatic heteroring containing one or two nitrogen atom; each ring optionally substituted with one or two residues selected independently from each other from the group consisting of $C_{1-4}$-alkyl-, halogen or $C_{1-4}$-haloalkyl-;
$R^5$ is H;
$R^6$ is H;
$R^7$ is H;
or a pharmaceutically acceptable salt thereof.

Preferred are the above compounds of formula 1, wherein
A is phenyl or pyridinyl;
$R^{1a}$ is

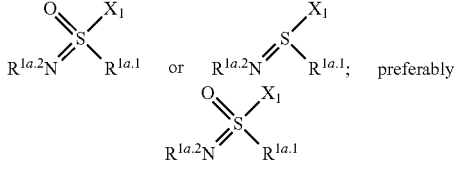

$R^{1a.1}$ is methyl, ethyl, i-propyl, n-propyl;
$R^{1a.2}$ is NC—;
$R^{1b}$ is H;
$R^2$ is ethyl, i-propyl, 2-butyl, cyclobutyl, 1-methylpyrazolyl, or benzyl or 4-NC-benzyl;
$R^3$ is methyl;
$R^4$ is phenyl or pyridinyl, each ring optionally substituted with one or two residues selected independently from each other from the group consisting of methyl, ethyl, propyl, F, Br, Cl, $F_2HC$— or $F_3C$—;
$R^5$ is H;
$R^6$ is H;
$R^7$ is H;
or a pharmaceutically acceptable salt thereof.

Preferred are the above compounds of formula 1, wherein
A is phenyl;
$R^{1a}$ is

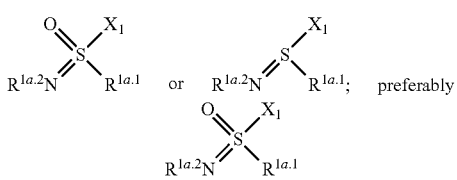

$R^{1a.1}$ is methyl;
$R^{1a.2}$ is NC—;
$R^{1b}$ is H;
$R^2$ is ethyl, i-propyl, cyclobutyl, 1-methylpyrazolyl, benzyl or 4-NC-benzyl;
$R^3$ is methyl;
$R^4$ is phenyl or pyridinyl, each ring optionally substituted with one or two residues selected independently from each other from the group consisting of F, $F_2HC$— or $F_3C$—;
$R^5$ is H;
$R^6$ is H;
$R^7$ is H;
or a pharmaceutically acceptable salt thereof.

Preferred are the above compounds of formula 1, wherein
A is phenyl;
$R^{1a}$ is

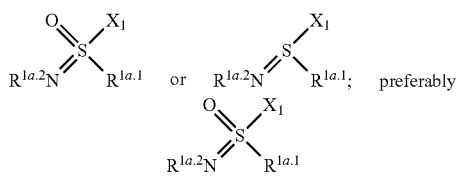

$R^{1a.1}$ is methyl;
$R^{1a.2}$ is NC—;
$R^{1b}$ is H;
$R^2$ is selected from a group consisting of

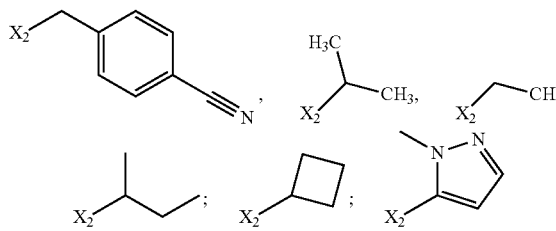

$R^3$ is methyl;
$R^4$ is selected from a group consisting of

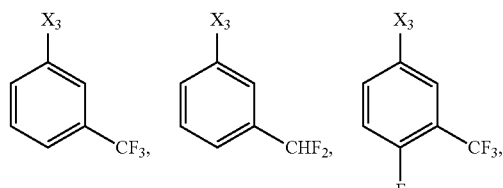

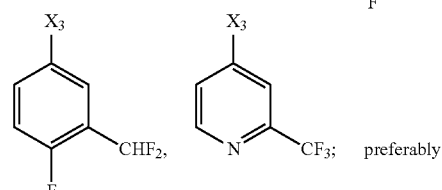

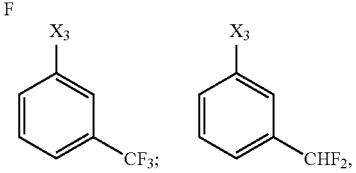

$R^5$ is H;
$R^6$ is H;
$R^7$ is H;
or a pharmaceutically acceptable salt thereof.

In a preferred embodiment of the invention $R^4$ is one of the above mentioned ring carrying the above mentioned optional substituted in meta-position to the element connection $R^4$ with the compound of formula 1.

From the above mentioned compounds those are preferred wherein $R^4$ is

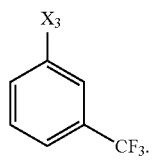

From the above mentioned compounds those are preferred wherein $R^4$ is

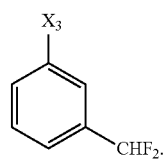

From the above mentioned compounds those are preferred wherein $R^4$ is

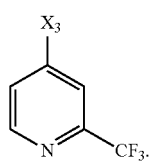

From the above mentioned compounds those are preferred wherein $R^4$ is

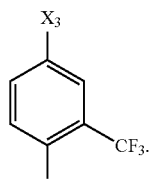

From the above mentioned compounds those are preferred wherein $R^4$ is

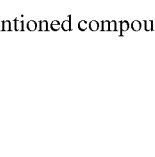

[Structure of X$_3$-substituted phenyl with CHF$_2$ and F groups]

In another embodiment of the invention preferred are the above compounds of formula 1, wherein A is phenyl or pyridinyl; preferably phenyl;

R$^{1a}$ is

[Structure: R$^{1a.2}$N-S(=O)(X$_1$)-R$^{1a.1}$];

R$^{1a.1}$ is C$_{1-4}$-alkyl-, C$_{3-6}$-cycloalkyl-, C$_{1-4}$-alkyl-NH— or (C$_{1-4}$-alkyl)$_2$N—, preferably C$_{1-4}$-alkyl- or C$_{3-6}$-cycloalkyl-;

R$^{1a.2}$ is H, methyl, NC—, Me-SO$_2$—;

R$^{1b}$ is H, methyl, F, preferably H;

R$^2$ is C$_{1-6}$-alkyl or a residue selected from the group consisting of C$_{3-6}$-cycloalkyl-, and a five-membered, aromatic heteroring containing one or two nitrogen atoms, each of the above rings optionally substituted with C$_{1-4}$-alkyl-;

R$^3$ is H or C$_{1-4}$-alkyl-;

R$^4$ is phenyl, a six-membered, aromatic heteroring containing one or two N; each optionally substituted with one or two residues selected independently from each other from the group consisting of halogen or C$_{1-4}$-haloalkyl-; preferably F, F$_2$HC— or F$_3$C—;

R$^5$ is H;

R$^6$ is H;

R$^7$ is H;

or a pharmaceutically acceptable salt thereof.

In another embodiment of the invention preferred are the above compounds of formula 1, wherein A is phenyl;

R$^{1a}$ is

[Structure: R$^{1a.2}$N-S(=O)(X$_1$)-R$^{1a.1}$];

R$^{1a.1}$ is C$_{1-4}$-alkyl-;

R$^{1a.2}$ is NC—;

R$^2$ is ethyl, i-propyl, cyclopropyl, cyclobutyl, 1-methyl-pyrazolyl;

R$^3$ is methyl;

R$^4$ is phenyl; substituted with one or two residues selected independently from each other from the group consisting of F, F$_2$HC— or F$_3$C—;

R$^{1b}$, R$^5$, R$^6$ and R$^7$ is H;

or a pharmaceutically acceptable salt thereof.

Preferred are

| Example# | Structure |
|---|---|
| 1 | [Structure of compound 1] |
| 2 | [Structure of compound 2] |
| 4 | [Structure of compound 4] |

-continued
| Example# | Structure |
|---|---|
| 5 | 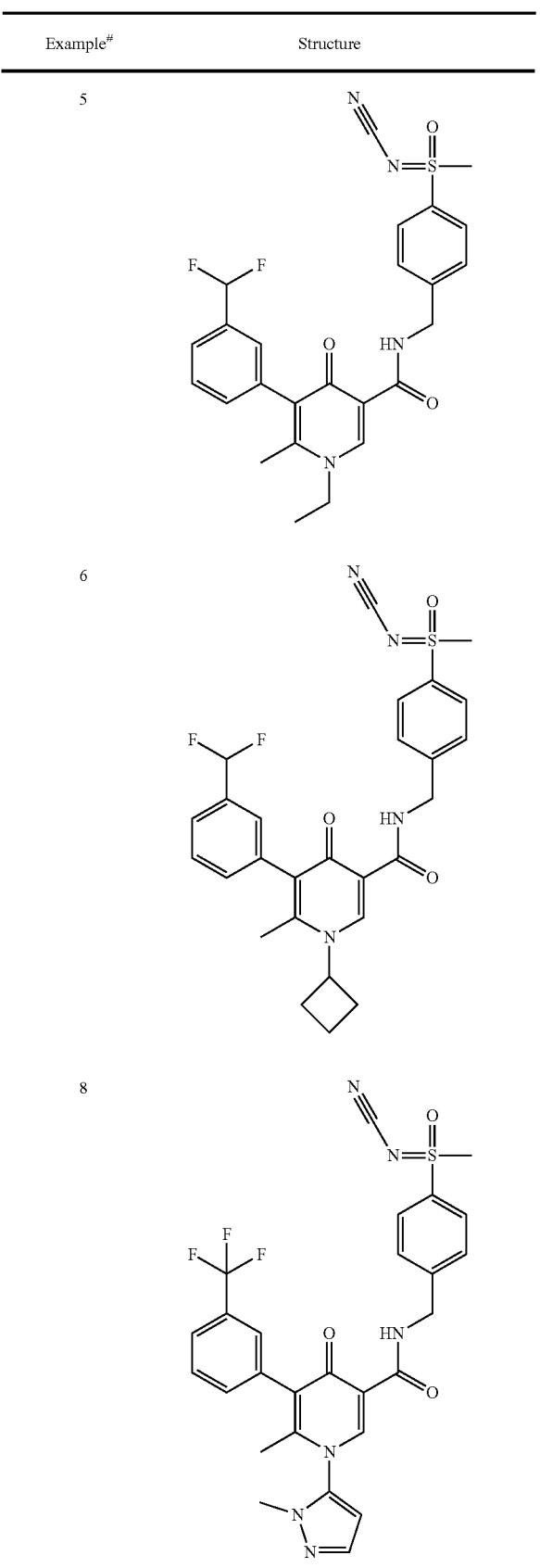 |
| 6 | 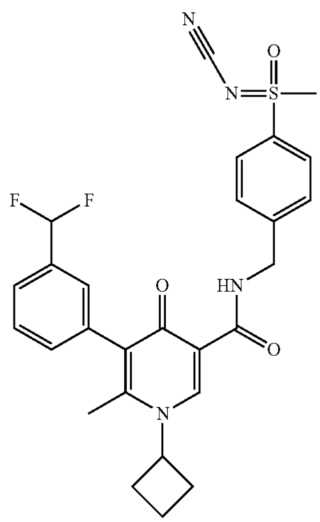 [SMILES: Cc1c(-c2cccc(C(F)F)c2)c(=O)c(C(=O)NCc2ccc(S(C)(=O)=NC#N)cc2)cn1C1CCC1] |
| 8 | 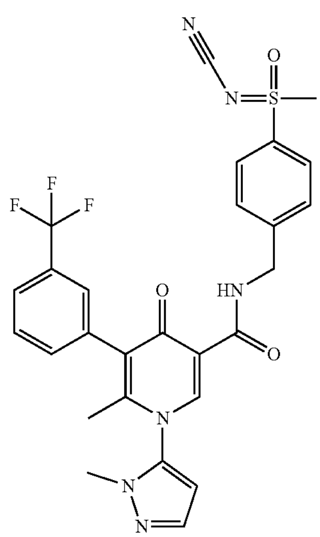 [SMILES: Cc1c(-c2cccc(C(F)(F)F)c2)c(=O)c(C(=O)NCc2ccc(S(C)(=O)=NC#N)cc2)cn1-c1ccnn1C] |
-continued
| Example# | Structure |
|---|---|
| 10 | 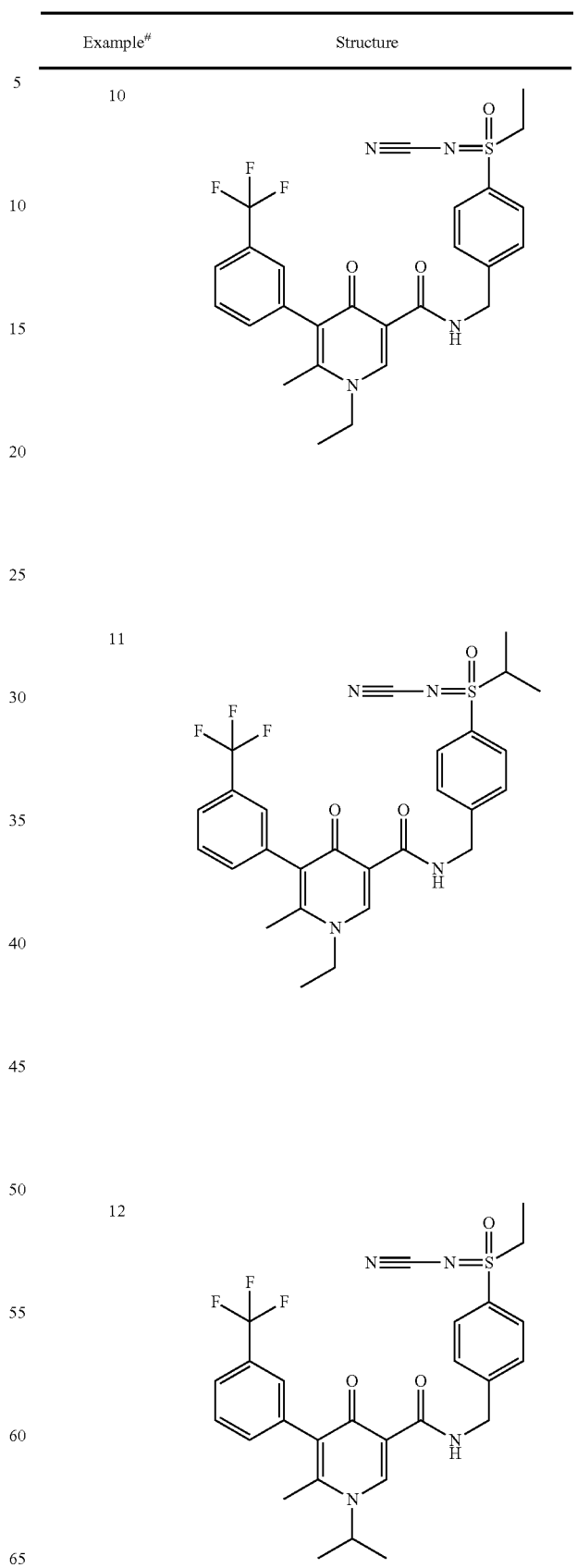 |
| 11 | 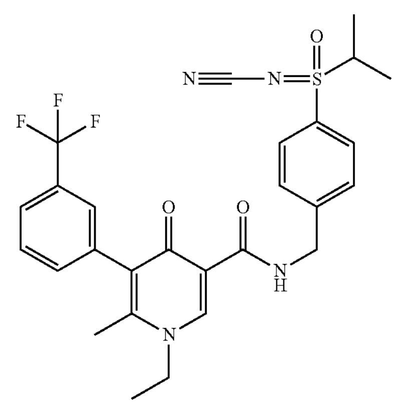 |
| 12 | 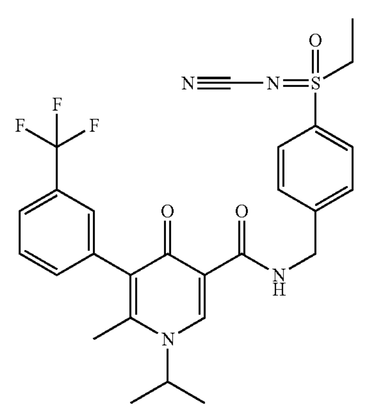 |

-continued
| Example# | Structure |
|---|---|
| 18 | 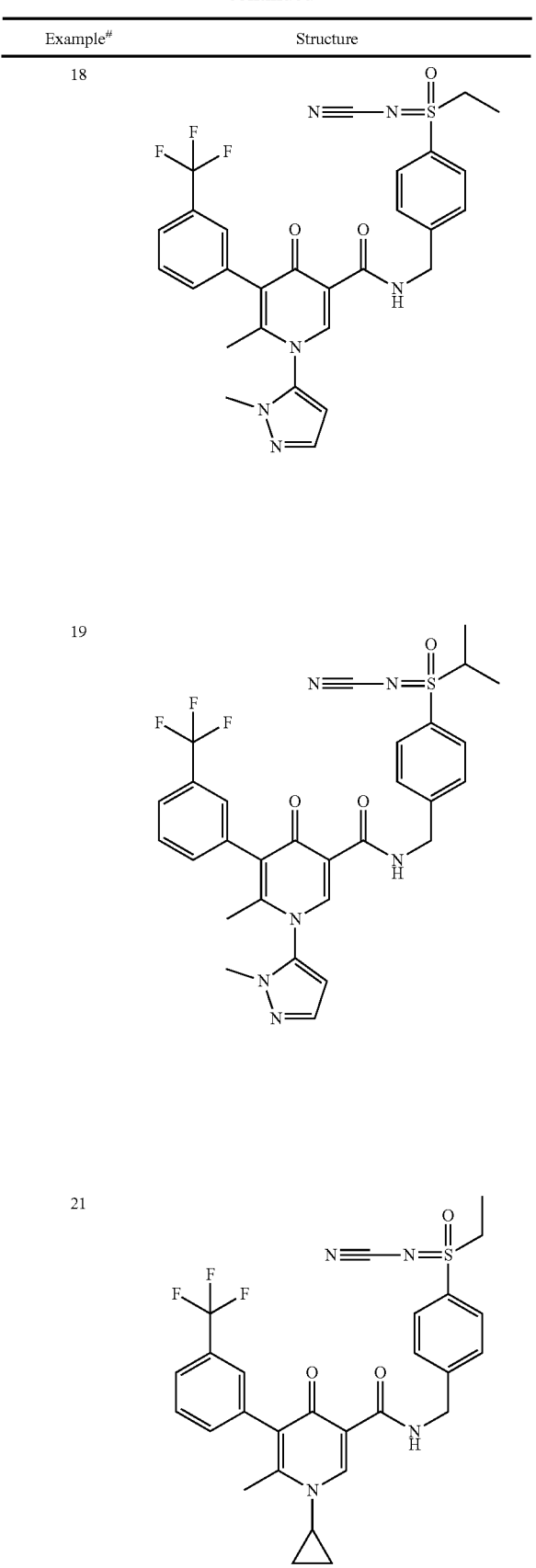 |
| 19 | 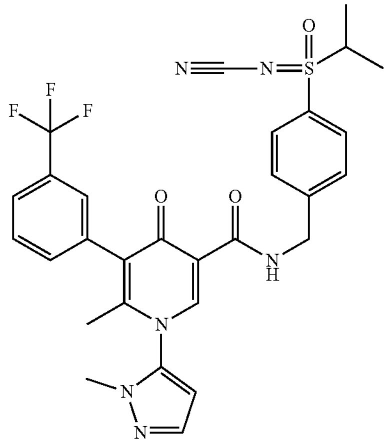 [SMILES: Cc1c(-c2cccc(C(F)(F)F)c2)c(=O)c(C(=O)NCc2ccc(S(=O)(=NC#N)C(C)C)cc2)cn1-c1ccnn1C] |
| 21 | 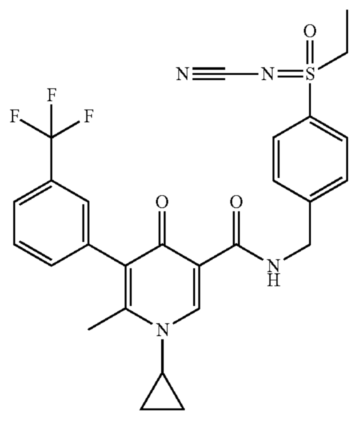 [SMILES: CCS(=O)(=NC#N)c1ccc(CNC(=O)c2cn(C3CC3)c(C)c(-c3cccc(C(F)(F)F)c3)c2=O)cc1] |
-continued
| Example# | Structure |
|---|---|
| 29 | 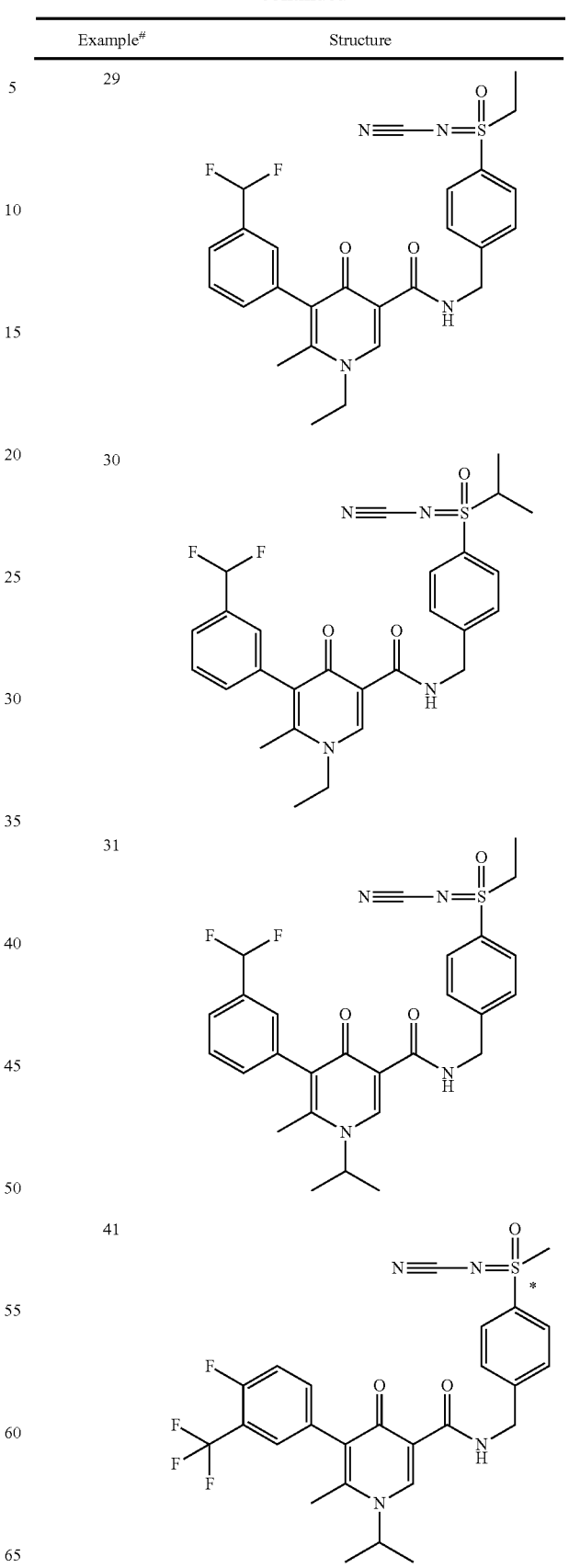 |
| 30 | 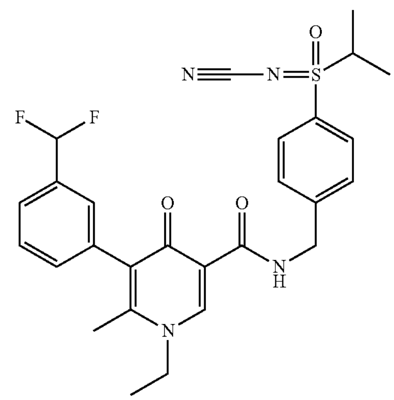 [SMILES: CCn1cc(C(=O)NCc2ccc(S(=O)(=NC#N)C(C)C)cc2)c(=O)c(-c2cccc(C(F)F)c2)c1C] |
| 31 | 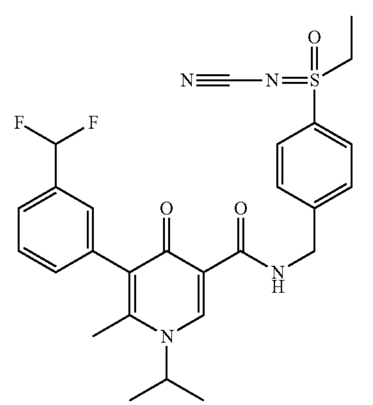 [SMILES: CCS(=O)(=NC#N)c1ccc(CNC(=O)c2cn(C(C)C)c(C)c(-c3cccc(C(F)F)c3)c2=O)cc1] |
| 41 | 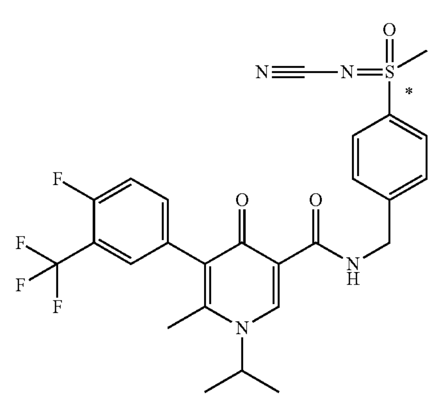 [SMILES: Cc1c(-c2ccc(F)c(C(F)(F)F)c2)c(=O)c(C(=O)NCc2ccc(S(C)(=O)=NC#N)cc2)cn1C(C)C] |

| Example# | Structure |
|---|---|
| 42 | 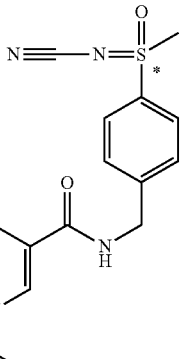 |
| 47 | 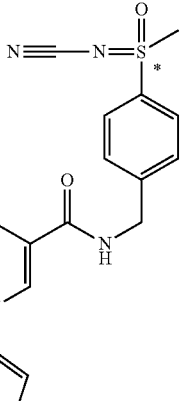 | example numbers are according to the numbering in the Preparation/experimental section The residue $R^{1a}$ is chiral, preferred is the Eutomer.

USED TERMS AND DEFINITIONS

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$-alkyl means an alkyl group or radical having 1 to 6 carbon atoms.

In general in single groups like HO, $H_2N$, OS, $O_2S$, NC (cyano), HOOC, $F_3C$ or the like, the skilled artisan can see the radical attachment point(s) to the molecule from the free valences of the group itself. For combined groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail. An asterisk, a dashed or a dotted line may be used in sub-formulas to indicate the bond which is connected to the core molecule as defined.

For example, the term "3-carboxypropyl-group" represents the following substituent:

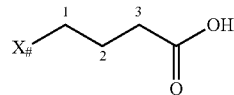

wherein the carboxy group is attached to the third carbon atom of the propyl group. The terms "1-methylpropyl-", "2,2-dimethylpropyl-" or "cyclopropylmethyl-" group represent the following groups:

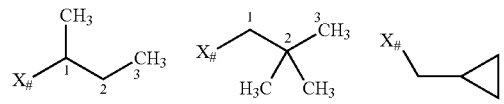

A X with a subscript number or "#", a dashed or a dotted line may be used in sub-formulas to indicate the bond which is connected to the core molecule as defined.

Many of the followings terms may be used repeatedly in the definition of a formula or group and in each case have one of the meanings given above, independently of one another.

The term "substituted" as used herein, means that any one or more hydrogens on the designated atom is replaced with a selection from the indicated group, provided that the designated atom's normal valence is not exceeded, and that the substitution results in a stable compound.

The expressions "prevention", "prophylaxis", "prophylactic treatment" or "preventive treatment" used herein should be understood synonymous and in the sense that the risk to develop a condition mentioned hereinbefore is reduced, especially in a patient having elevated risk for said conditions or a corresponding anamnesis, e.g. elevated risk of developing metabolic disorder such as diabetes or obesity or another disorder mentioned herein. Thus the expression "prevention of a disease" as used herein means the management and care of an individual at risk of developing the disease prior to the clinical onset of the disease. The purpose of prevention is to combat the development of the disease, condition or disorder, and includes the administration of the active compounds to prevent or delay the onset of the symptoms or complications and to prevent or delay the development of related diseases, conditions or disorders. Success of said preventive treatment is reflected statistically by reduced incidence of said condition within a patient population at risk for this condition in comparison to an equivalent patient population without preventive treatment.

The expression "treatment" or "therapy" means therapeutic treatment of patients having already developed one or more of said conditions in manifest, acute or chronic form, including symptomatic treatment in order to relieve symptoms of the specific indication or causal treatment in order to reverse or partially reverse the condition or to delay the progression of the indication as far as this may be possible, depending on the condition and the severity thereof. Thus the expression "treatment of a disease" as used herein means the management and care of a patient having developed the disease, condition or disorder. The purpose of treatment is to combat the disease, condition or disorder. Treatment includes the administration of the active compounds to eliminate or control the disease, condition or disorder as well as to alleviate the symptoms or complications associated with the disease, condition or disorder.

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

When in the claimed ring system A (e.g. SA) the two residues $R^{1a}$ and $R^{1b}$ are "together a $C_{2-4}$-alkylene forming a carbocyclic heterering; rings similar to example SB are meant in this case $R^{1a}$ and $R^{1b}$ are in ortho position to each other.

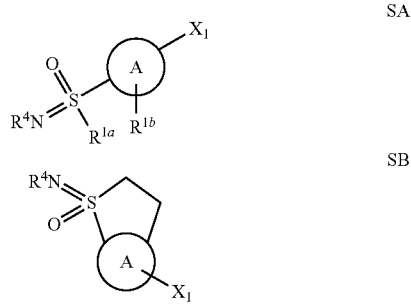

The term halogen generally denotes fluorine, chlorine, bromine and iodine.

As used herein the term "prodrug" refers to (i) an inactive form of a drug that exerts its effects after metabolic processes within the body converting it to a usable or active form, or (ii) a substance that gives rise to a pharmacologically active metabolite, although not itself active (i.e. an inactive precursor).

The terms "prodrug" or "prodrug derivative" mean a covalently-bonded derivative, carrier or precursor of the parent compound or active drug substance which undergoes at least some biotransformation prior to exhibiting its pharmacological effect(s). Such prodrugs either have metabolically cleavable or otherwise convertible groups and are rapidly transformed in vivo to yield the parent compound, for example, by hydrolysis in blood or by activation via oxidation as in case of thioether groups. Most common prodrugs include esters and amide analogs of the parent compounds. The prodrug is formulated with the objectives of improved chemical stability, improved patient acceptance and compliance, improved bioavailability, prolonged duration of action, improved organ selectivity, improved formulation (e.g., increased hydrosolubility), and/or decreased side effects (e.g., toxicity). In general, prodrugs themselves have weak or no biological activity and are stable under ordinary conditions. Prodrugs can be readily prepared from the parent compounds using methods known in the art, such as those described in A Textbook of Drug Design and Development, Krogsgaard-Larsen and H. Bundgaard (eds.), Gordon & Breach, 1991, particularly Chapter 5: "Design and Applications of Prodrugs"; Design of Prodrugs, H. Bundgaard (ed.), Elsevier, 1985; Prodrugs: Topical and Ocular Drug Delivery, K. B. Sloan (ed.), Marcel Dekker, 1998; Methods in Enzymology, K. Widder et al. (eds.), Vol. 42, Academic Press, 1985, particularly pp. 309-396; Burger's Medicinal Chemistry and Drug Discovery, 5th Ed., M. Wolff (ed.), John Wiley & Sons, 1995, particularly Vol. 1 and pp. 172-178 and pp. 949-982; Pro-Drugs as Novel Delivery Systems, T. Higuchi and V. Stella (eds.), Am. Chem. Soc., 1975; Bioreversible Carriers in Drug Design, E. B. Roche (ed.), Elsevier, 1987, each of which is incorporated herein by reference in their entireties.

The term "pharmaceutically acceptable prodrug" as used herein means a prodrug of a compound of the invention which is, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine (2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidinyl, sodium hydroxide, triethanolamine (2,2',2"-nitrilotris(ethanol)), tromethamine, zinc hydroxide, acetic acid, 2.2-dichloro-acetic acid, adipic acid, alginic acid, ascorbic acid, L-aspartic acid, benzenesulfonic acid, benzoic acid, 2,5-dihydroxybenzoic acid, 4-acetamido-benzoic acid, (+)-camphoric acid, (+)-camphor-10-sulfonic acid, carbonic acid, cinnamic acid, citric acid, cyclamic acid, decanoic acid, dodecylsulfuric acid, ethane-1, 2-disulfonic acid, ethanesulfonic acid, 2-hydroxy-ethanesulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxo-glutaric acid, glycerophosphoric acid, glycine, glycolic acid, hexanoic acid, hippuric acid, hydrobromic acid, hydrochloric acid, isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1, 5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminium, calcium, lithium, magnesium, potassium, sodium, zinc and the like. (also see Pharmaceutical salts, Berge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts,) also comprise a part of the invention.

The term "$C_{1-n}$-alkyl", wherein n is an integer from 2 to 6, either alone or in combination with another radical denotes an acyclic, saturated, branched or linear hydrocarbon radical with 1 to 6 C atoms. For example the term $C_{1-5}$-alkyl embraces the radicals $H_3C-$, $H_3C-CH_2-$, $H_3C-CH_2-CH_2-$, $H_3C-CH(CH_3)-$, $H_3C-CH_2-CH_2-CH_2-$, $H_3C-CH_2-CH(CH_3)-$, $H_3C-CH(CH_3)-CH_2-$, $H_3C-C(CH_3)_2-$, $H_3C-CH_2-CH_2-CH_2-CH_2-$, $H_3C-CH_2-CH_2-CH(CH_3)-$, $H_3C-CH_2-CH(CH_3)-CH_2-$, $H_3C-CH(CH_3)-CH_2-CH_2-$, $H_3C-CH_2-C(CH_3)_2-$, $H_3C-C(CH_3)_2-CH_2-$, $H_3C-CH(CH_3)-CH(CH_3)-$ and $H_3C-CH_2-CH(CH_2CH_3)-$.

The term "$C_{1-6}$-alkylene" wherein n is an integer 2 to 6, either alone or in combination with another radical, denotes an acyclic, straight or branched chain divalent alkyl radical containing from 1 to 6 carbon atoms. For example the term $C_{1-4}$-alkylene includes $-CH_2-$, $-CH_2-CH_2-$, $-CH(CH_3)-$, $-CH_2-CH_2-CH_2-$, $-C(CH_3)_2-$, $-CH(CH_2CH_3)-$, $-CH(CH_3)-CH_2-$, $-CH_2-CH(CH_3)-$, $-CH_2-CH_2-CH_2-CH_2-$, $-CH_2-CH_2-CH(CH_3)-$, $-CH(CH_3)-CH_2-CH_2-$, $-CH_2-CH(CH_3)-CH_2-$, $-CH_2-C(CH_3)_2-$, $-C(CH_3)_2-CH_2-$, $-CH(CH_3)-CH(CH_3)-$, $-CH_2-CH(CH_2CH_3)-$, $-CH(CH_2CH_3)-CH_2-$, $-CH(CH_2CH_2CH_3)-$, $-CH(CH(CH_3))_2-$ and $-C(CH_3)(CH_2CH_3)-$.

The term "$C_{2-n}$-alkylene" wherein n is an integer 3 to 5, either alone or in combination with another radical, denotes an acyclic, straight or branched chain divalent alkyl radical containing from 2 to 5 carbon atoms. For example the term $C_{2-5}$-alkylene includes $-CH_2-CH_2-$, $-CH(CH_3)-$, $-CH_2-CH_2-CH_2-$, $-C(CH_3)_2-$, $-CH(CH_2CH_3)-$, $-CH(CH_3)-CH_2-$, $-CH_2-CH(CH_3)-$, $-CH_2-CH_2-CH_2-CH_2-$, $-CH_2-CH_2-CH(CH_3)-$, $-CH(CH_3)-CH_2-CH_2-$, $-CH_2-CH(CH_3)-CH_2-$, $-CH_2-C(CH_3)_2-$, $-C(CH_3)_2-CH_2-$, $-CH(CH_3)-CH(CH_3)-$, $-CH_2-CH(CH_2CH_3)-$, $-CH(CH_2CH_3)-CH_2-$, $-CH(CH_2CH_2CH_3)-$, $-CH(CH(CH_3))_2-$ and $-C(CH_3)(CH_2CH_3)-$.

By the term "halo" added to a "alkyl", "alkylene" or "cycloalkyl" group (saturated or unsaturated) is such a alkyl or cycloalkyl group meant wherein one or more hydrogen atoms are replaced by a halogen atom selected from among fluorine, chlorine or bromine, preferably fluorine and chlorine, particularly preferred is fluorine. Examples include: $H_2FC-$, $HF_2C-$, $F_3C-$.

The term "$C_{3-6}$-cycloalkyl", wherein n is an integer from 4 to 6, either alone or in combination with another radical denotes a cyclic, saturated, unbranched hydrocarbon radical with 3 to 6 C atoms. For example the term $C_{3-6}$-cycloalkyl includes cyclopropyl, cyclobutyl, cyclopentyl and cyclohexyl.

The term "aryl" as used herein, either alone or in combination with another radical, denotes a carbocyclic aromatic monocyclic group containing 6 carbon atoms which may be further fused to a second five- or six-membered, carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

With the elements of a ring the atoms forming this ring are meant. So, a phenyl ring contains 6 elements which are all carbon atoms, a pyrrol ring contains 5 elements, wherein 4 elements are carbon atoms and the remaining element is a nitrogen atom.

The term "aromatic heteroring" means a unsaturated monocyclic-ring system containing one, two, three or four heteroatoms selected from N, $(O^-)N^+$, O or $(O)_rS$, wherein r=0, 1 or 2, consisting of four, five or six ring atoms. If the term is connected with a more detailed definition of the amount or kind of heteroatoms and the possible size of the aromatic heteroring, the detailed definition is restricting the above mentioned definition.

Furthermore the term is intended to include all possible isomeric forms. Thus, the term includes (if not otherwise restricted) the following exemplary structures which are not depicted as radicals as each form may be attached through a covalent bond to any atom so long as appropriate valences are maintained:

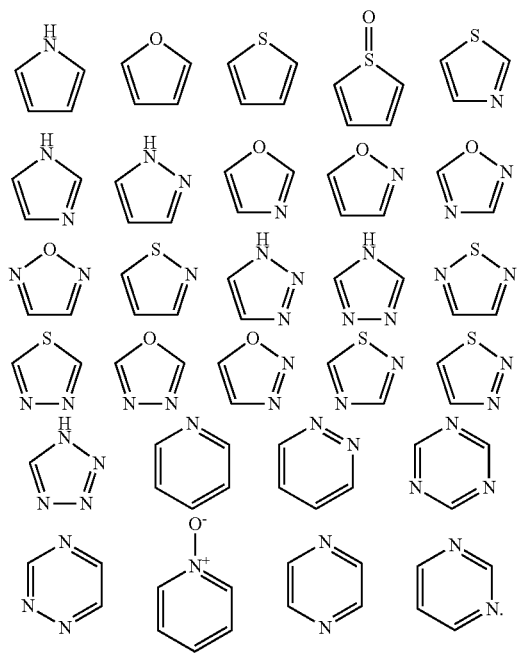

Preparation

The compounds according to the present invention and their intermediates may be obtained using methods of synthesis which are known to the one skilled in the art and described in the literature of organic synthesis. Preferably, the compounds are obtained in analogous fashion to the methods of preparation explained more fully hereinafter, in particular as described in the experimental section. In some cases, the order in carrying out the reaction steps may be varied. Variants of the reaction methods that are known to the one skilled in the art but not described in detail here may also be used. The general processes for preparing the compounds according to the invention will become apparent to the one skilled in the art studying the following schemes.

Starting materials are commercially available or may be prepared by methods that are described in the literature or herein, or may be prepared in an analogous or similar manner. Any functional groups in the starting materials or intermediates may be protected using conventional protecting groups.

These protecting groups may be cleaved again at a suitable stage within the reaction sequence using methods familiar to the one skilled in the art.

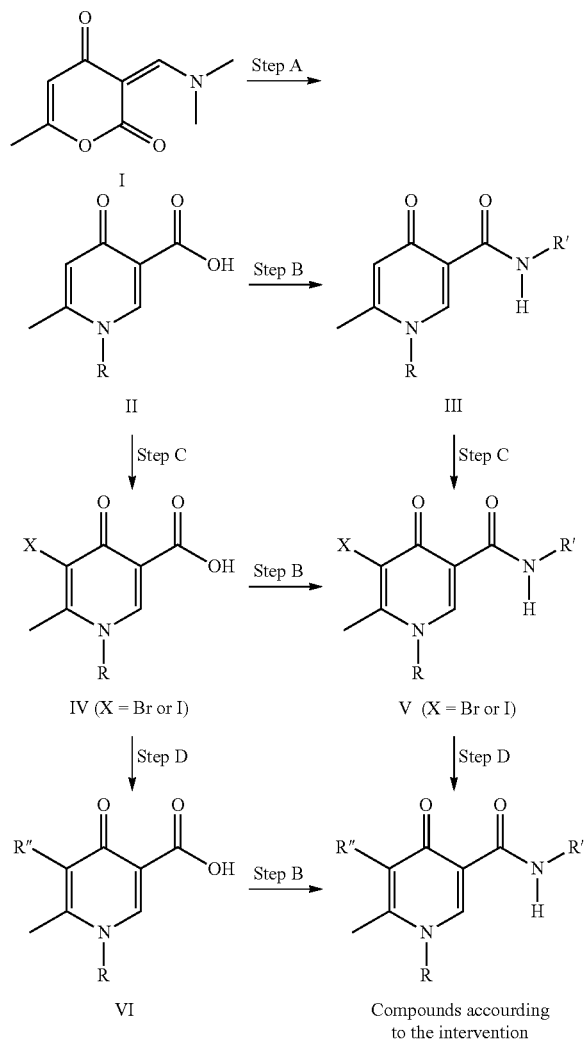

Starting material I can be prepared as described in US2003/87940.

Intermediates II can be prepared as described in WO10133973 and US2003/87940 by heating starting material I with amines R—NH$_2$ in the presence of a strong base, for example sodium tert-butoxide or sodium ethoxide, in an organic solvent, for example ethanol. The reaction usually takes place within 2 to 72 hours. Preferred reaction temperatures are between 50° C. and 150° C.

The amide coupling (Step B, intermediates II→intermediates III, intermediates IV→intermediates V, intermediates VI→compounds of the invention) can be achieved by reacting carboxylic acid intermediates II, IV or VI with amines R'—NH$_2$ in the presence of an amide coupling reagent, for example O-(Benzotriazol-1-yl)-N,N,N',N'-tetramethyluronium hexafluorophosphate (HBTU),O-(Benzotriazol-1-yl)-N,N,N',N'-tetramethyluronium tetrafluoroborate (TBTU) or propane phosphonic acid anhydride, and in the presence of a base, for example triethylamine, diisopropylethylamine (DIPEA, Hünig's base) or N-methyl-morpholine, in an organic solvent, for example N,N-dimethylformamide (DMF), N-methyl-2-pyrrolidone (NMP) or dimethylacetamide (DMA) or mixtures thereof. The reaction usually takes place within 1 to 72 hours. Preferred reaction temperatures are between 0° C. and 50° C., most preferred room temperature. Alternatively, the carboxylic acid intermediates can be activated first as described in US2003/87940, for example with 1,1'-carbonyldiimidazole (CDI) in DMF, followed by reaction with the amine R'—NH$_2$.

The bromination (Step C, X=Br, intermediates II→intermediates IV, intermediates III→intermediates V) can be achieved by reacting intermediates II or III with bromination agents, for example bromine or N-bromosuccinimide, in an organic solvent, for example acetic acid, dichloromethane, methanol, acetonitrile, tetrahydrofuran or mixtures thereof. The iodination (Step C, X=I, intermediates II→intermediates IV, intermediates III→intermediates V) can be achieved by reacting intermediates II or III with iodination agents, for example iodine, iodinechloride (I—Cl) or N-iodosuccinimide, in an organic solvent, for example acetic acid, methanol, ethanol, dichloromethane, acetonitrile, N,N-dimethylformamide, tetrahydrofuran or mixtures thereof. The halogenation reaction usually takes place within 1 to 72 hours. Preferred reaction temperatures are between 0° C. and 50° C., most preferred room temperature.

The Suzuki coupling (Step D, intermediates IV→intermediates VI, intermediates V→compounds according to the invention) can be achieved by reacting intermediates IV or V with aryl or heteroaryl boronic acids R"—B(OH)$_2$ or the corresponding boronic esters in the presence of a palladium catalyst, for example tetrakis(triphenylphosphine)palladium(0) or [1,1'-bis(diphenylphosphino)ferrocene]dichloropalladium(II), and in the presence of a base, for example potassium carbonate, barium dihydroxide or cesium carbonate, in an organic solvent, for example toluene, benzene, ethanol, ethylene glycol dimethyl ether, acetonitrile, dioxane or mixtures thereof, optionally in the presence of water. The reaction usually takes place within 1 to 72 hours. Preferred reaction temperatures are between 50° C. and 150° C.

Compounds according to the present invention can also be prepared according to the following scheme starting from 4-hydroxy-6-methyl-nicotinic acid. Halogenation (Step C) as described above, followed by Suzuki coupling (Step D) as described above, followed by amide coupling (Step B) as described above, yields intermediates VII. The alkylation of the pyridone nitrogen (Step E) can be achieved by reacting intermediate VII with alkylating agents, for example alkyl bromides, alkyl iodides, alkyl tosylates, alkyl mesylates or dialkyl sulfates, in the presence of a base, for example sodium carbonate, potassium carbonate, potassium hydroxide, sodium hydroxide or cesium carbonate, in an organic solvent, N,N-dimethylformamide (DMF), N-methyl-2-pyrrolidone (NMP) or dimethylacetamide (DMA). The reaction usually takes place within 1 to 72 hours. Preferred reaction temperatures are between 50° C. and 150° C.

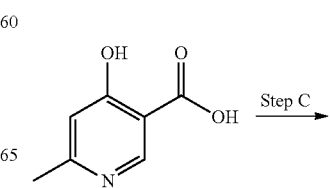

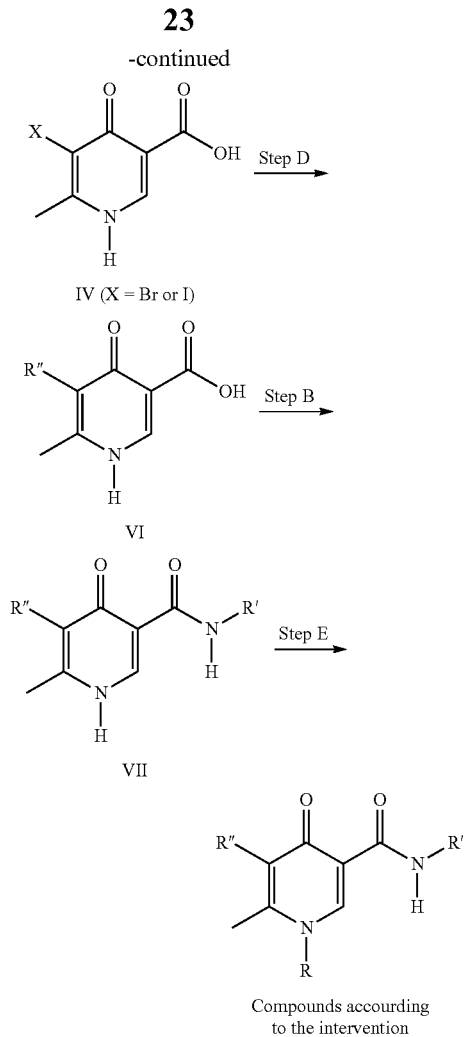

IV (X = Br or I)

VI

VII

Compounds accourding to the intervention

The intermediates for compounds according to the present invention with 2-alkyl substituents can be prepared according to Venkatramani et al., J. Het. Chem. 30, 723-738 (1993).

The synthesis of sulfinimides (sulfilimines) and sulfonimides (sulfoximines) has been extensively described in Reggelin et al., Synthesis, 1-64 (2000) and Bolm et al., Chem. Lett. 33, 482-487 (2004). The general processes for the preparation of N-cyano-sulfinimides (N-cyano-sulfoximines) are illustrated in the following scheme. As indicated, the order of imination and oxidation can usually be interchanged, and the syntheses can likewise start from sulfoxides instead of sulfides.

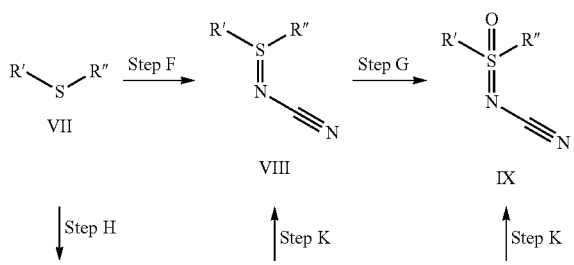

Intermediates VIII can be prepared as described in Bolm et al., Org. Lett. 9, 3809-3811 (2007) via direct imination of a thioether (intermediates VII) with cyanamide (Step F, intermediates VII→intermediates VIII) by reaction with an halogenating agent, for example N-bromo- or N-chlorosuccinimide, tert-butyl hypochlorite or iodine in the presence of cyanamide and a base, for example potassium or sodium tert-butoxide, in an organic solvent, for example methanol, tetrahydrofuran (THF) or acetonitrile. The reaction usually takes place within 1 to 72 hours. Preferred reaction temperatures are between 0° C. and 50° C., most preferred is room temperature. Alternatively, the imination (Step F, intermediates VII→intermediates VIII) can be achieved as described in Bolm et al., Org. Lett. 9, 2951-2954 (2007), by using phenyliodo diacetate [PhI(OAc)$_2$] and cyanamide in an organic solvent, for example acetonitrile or tetrahydrofuran (THF). The reaction usually takes place within 1 to 72 hours. Preferred reaction temperatures are between 0° C. and room temperature.

The oxidation (Step G, intermediates VIII→intermediates IX, intermediates XI→intermediates XII) can be achieved using a peroxycarboxylic acid as oxidizing agent, for example meta-chloroperoxybenzoic acid (mCPBA), optionally in the presence of a base, for example potassium carbonate, in an organic solvent, for example ethanol, methanol, dichloromethane or chloroform. The reaction usually takes place within 1 to 72 hours. Preferred reaction temperatures are between 0° C. and room temperature. Alternatively, other common oxidizing agents may be used to achieve this transformation, for example hydrogen peroxide, tert-butyl hydroperoxide, sodium hypochlorite, sodium iodate, sodium periodate, potassium permanganate, ruthenium tetroxide, potassium peroxymonosulfate (Oxone) or dimethyldioxirane.

Intermediates X can be obtained by imination of intermediates VII (Step H, intermediates VII→intermediates X) as described in Bolm. et al., Org. Lett. 6, 1305-1307 (2004), by reacting a thioether (intermediates VII) with trifluoroacetamide, phenyliodo diacetate [PhI(OAc)$_2$], rhodium acetate dimer [Rh$_2$(OAc)$_4$] and MgO in an organic solvent, for example dichloromethane. The reaction usually takes place within 1 to 72 hours. Preferred reaction temperatures are between 0° C. and room temperature.

The cleavage of the trifluoroacetamide (Step K, intermediates X→intermediates XI) can be achieved as described in Bolm. et al., Org. Lett. 6, 1305-1307 (2004), using a base, for example potassium carbonate, in an organic solvent, for example methanol. The reaction usually takes place within 1 to 72 hours. Preferred reaction temperatures are between 0° C. and 50° C., most preferred room temperature.

Alternatively, intermediates XI can be prepared by the imination of intermediates VII using other electrophilic nitrogen sources, for example tert-butyl 3-(4-cyano-phenyl)-oxaziridine-2-carboxylate (followed by cleavage of the Boc-protecting group), O-mesityl sulfonyl hydroxylamine (MSH), or hydrazoic azid.

The cyanation of sulfinimides or sulfonimides (Step K, intermediates XI→intermediates VIII, intermediates XII→intermediates IX) can be achieved as described in Bolm et al., Org. Lett. 9, 2951-2954 (2007), by reacting the starting material with cyanogen bromide, optionally 4-dimethylaminopyridine (DMAP) and optionally a base, for example triethylamine, in an organic solvent, for example dichloromethane. The reaction usually takes place within 1 to 72 hours. Preferred reaction temperatures are between 0° C. and 50° C., most preferred room temperature.

The synthesis of sulfonimidamides has been described in Johnson et al., J. Org. Chem. 44, 2055-2061 (1975), Bolm et al., J. Org. Chem. 75, 3301-3310 (2010) and in WO09156336. The general synthetic scheme for the preparation of sulfonimidamides from sulfinamides is depicted in the following scheme.

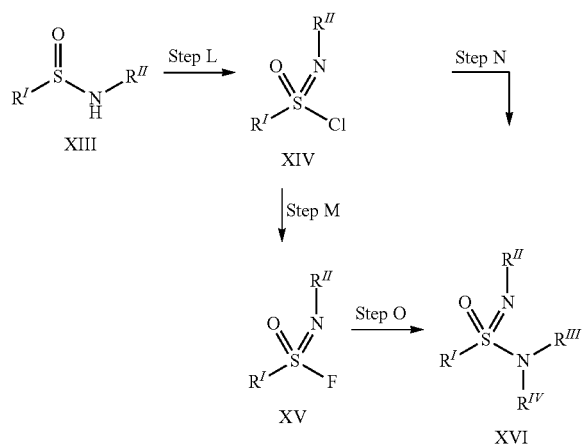

Sulfinamides (starting material XIII) can be prepared as described in Johnson et al., J. Org. Chem. 44, 2055-2061 (1975) by reacting sulfinyl chlorides with a primary or secondary amine, optionally in the presence of an additional base, for example pyridine or a tertiary amine, in an organic solvent, for example dichloromethane, tetrahydrofuran, diethylether, acetonitrile, toluene, N,N-dimethylformamide, ethanol or ethyl acetate. The reaction usually takes place within 1-72 hours. Preferred reaction temperatures are between 0° C. and room temperature.

Sulfonimidoyl chlorides (intermediates XIV) can be prepared as described in Johnson et al., J. Org. Chem. 44, 2055-2061 (1975), by reacting sulfinamides (starting material XIII) with a chlorinating agent, for example chlorine, N-chlorosuccinimide (NCS), N-chloro-benzotriazole or tert-butyl hypochlorite in an organic solvent, for example dichloromethane, diethylether, benzene, toluene, carbon tetrachloride, acetonitrile or tetrahydrofuran (Step L). The reaction usually takes place within less than 1 hour. Preferred reaction temperatures are between −78° C. and room temperature, mostly preferred between 0° C. and room temperature.

Sulfonimidoyl fluorides (intermediates XV) can be prepared as described in Johnson et al., J. Org. Chem. 48, 1-3 (1983) and Gnamm et al., Bioorg. Med. Chem. Lett. 12, 3800-3806 (2012), by reacting sulfonimidoyl chlorides (intermediates XIV) with a fluoride salt, for example potassium fluoride, sodium fluoride or tetrabutylammonium fluoride, optionally in the presence of a crown ether, for example 18-crown-6, in an organic solvent, for example acetonitrile or tetrahydrofuran (Step M). The reaction takes place within 1 to 24 hours. Preferred reaction temperatures are between 0° C. and room temperature, mostly preferred room temperature.

Sulfonimidamides (intermediates XVI) can be prepared as described in Johnson et al., J. Org. Chem. 44, 2055-2061 (1975), Bolm et al., J. Org. Chem. 75, 3301-3310 (2010), and WO09156336 by reacting sulfonimidoyl chlorides (intermediates XIV) with a primary or secondary, aliphatic or aromatic amine, optionally in the presence of an additional base, for example pyridine or a tertiary amine, in an organic solvent, for example acetonitrile, tetrahydrofuran, N,N-dimethylformamide or benzene (Step N). The reaction takes place within 1 to 72 hours. Preferred reaction temperatures are between 0° C. and room temperature.

Alternatively, sulfonimidamides (intermediates XVI) can be prepared as described in Gnamm et al., Bioorg. Med. Chem. Lett. 22, 3800-3806 (2012) by reacting sulfonimidoyl fluorides (intermediates XV) with a primary or secondary, aliphatic or aromatic amine, optionally in the presence of an additional base, for example pyridine or a tertiary amine, for example 1,8-diazabicyclo[5.4.0]undec-7-ene (DBU), in an organic solvent, for example acetonitrile, tetrahydrofuran, N,N-dimethylformamide or benzene (Step O). The reaction takes place within 1 to 72 hours. Preferred reaction temperatures are between 0° C. and the boiling point of the solvent, mostly preferred between room temperature and 110° C.

Preliminary Remarks:

$^1$H-NMR have been obtained for the examples of the invention. The HPLC data given are measured under the following conditions (r.t.=retention time):

| Method Name: | V001_007 | | | |
|---|---|---|---|---|
| Column: | XBridge C18, 4.6 × 30 mm, 3.5 μm | | | |
| Column Supplier: | Waters | | | |
| Gradient/Solvent Time [min] | % Sol [H2O, 0.1% TFA] | % Sol [Methanol] | Flow [ml/min] | Temp [° C.] |
| 0.0 | 95 | 5 | 4 | 60 |
| 1.6 | 0 | 100 | 4 | 60 |
| 1.85 | 0 | 100 | 4 | 60 |
| 1.9 | 95 | 5 | 4 | 60 |

| Method Name: | V003_003 | | | |
|---|---|---|---|---|
| Column: | XBridge C18, 4.6 × 30 mm, 3.5 μm | | | |
| Column Supplier: | Waters | | | |
| Gradient/Solvent Time [min] | % Sol [H2O, 0.1% NH$_3$] | % Sol [Methanol] | Flow [ml/min] | Temp [° C.] |
| 0.0 | 95 | 5 | 4 | 60 |
| 0.2 | 95 | 5 | 4 | 60 |
| 1.5 | 0 | 100.0 | 4 | 60 |
| 1.75 | 0 | 100 | 4 | 60 |

| Method Name: | X001_004 | | | |
|---|---|---|---|---|
| Column: | XBridge C18, 2.1 × 20 mm, 2.5 μm | | | |
| Column Supplier: | Waters | | | |
| Gradient/Solvent Time [min] | % Sol [H2O, 0.10% TFA] | % Sol [Methanol] | Flow [ml/min] | Temp [° C.] |
| 0.0 | 95 | 5 | 1.4 | 60 |
| 0.05 | 95 | 5 | 1.4 | 60 |
| 1.00 | 0 | 100 | 1.4 | 60 |
| 1.1 | 0 | 100 | 1.4 | 60 |

Method Name: X012_S01
Column: Xbridge BEH C18, 2.1 × 30 mm, 1.7 μm
Column Supplier: Waters

| Gradient/ Solvent Time [min] | % Sol [H2O, 0.1% TFA] | % Sol [Acetonitrile] | Flow [ml/min] | Temp [° C.] |
|---|---|---|---|---|
| 0.0 | 99 | 1 | 1.6 | 60 |
| 0.02 | 99 | 1 | 1.6 | 60 |
| 1.00 | 0 | 100 | 1.6 | 60 |
| 1.10 | 0 | 100 | 1.6 | 60 |

Method Name: Z002_005
Column: Sunfire C18, 3 × 30 mm, 2.5 μm
Column Supplier: Waters

| Gradient/Solvent Time [min] | % Sol [H2O, 0.1% TFA] | % Sol [Methanol] | Flow [ml/min] | Temp [° C.] |
|---|---|---|---|---|
| 0.0 | 95 | 5 | 1.8 | 60 |
| 0.25 | 95 | 5 | 1.8 | 60 |
| 1.70 | 0 | 100 | 1.8 | 60 |
| 1.75 | 0 | 100 | 2.5 | 60 |
| 1.90 | 0 | 100 | 2.5 | 60 |

Method Name: Z002_007
Column: Sunfire C18, 3 × 30 mm, 2.5 μm
Column Supplier: Waters

| Gradient/Solvent Time [min] | % Sol [H2O, 0.1% TFA] | % Sol [Methanol] | Flow [ml/min] | Temp [° C.] |
|---|---|---|---|---|
| 0.0 | 95 | 5 | 1.9 | 60 |
| 0.20 | 95 | 5 | 1.9 | 60 |
| 1.55 | 0 | 100 | 1.9 | 60 |
| 1.60 | 0 | 100 | 2.4 | 60 |
| 1.80 | 0 | 100 | 2.4 | 60 |

Method Name: Z002_006
Column: Sunfire C18, 3 × 30 mm, 2.5 μm
Column Supplier: Waters

| Gradient/Solvent Time [min] | % Sol [H2O, 0.1% TFA] | % Sol [Methanol] | Flow [ml/min] | Temp [° C.] |
|---|---|---|---|---|
| 0.0 | 95 | 5 | 1.9 | 60 |
| 0.20 | 95 | 5 | 1.9 | 60 |
| 1.55 | 0 | 100 | 1.9 | 60 |
| 1.60 | 0 | 100 | 2.4 | 60 |
| 1.80 | 0 | 100 | 2.4 | 60 |

Method Name: Z002_002
Column: Sunfire C18, 3 × 30 mm, 2.5 μm
Column Supplier: Waters

| Gradient/Solvent Time [min] | % Sol [H2O, 0.1% TFA] | % Sol [Methanol] | Flow [ml/min] | Temp [° C.] |
|---|---|---|---|---|
| 0.0 | 95 | 5 | 2.2 | 60 |
| 0.05 | 95 | 5 | 2.2 | 60 |
| 1.40 | 0 | 100 | 2.2 | 60 |
| 1.80 | 0 | 100 | 2.2 | 60 |

Method Name: Z003_001
Column: XBridge C18, 3 × 30 mm, 2.5 μm
Column Supplier: Waters

| Gradient/Solvent Time [min] | % Sol [H2O, 0.1% NH3] | % Sol [Methanol] | Flow [ml/min] | Temp [° C.] |
|---|---|---|---|---|
| 0.0 | 95 | 5 | 2.2 | 60 |
| 0.05 | 95 | 5 | 2.2 | 60 |
| 1.40 | 0 | 100 | 2.2 | 60 |
| 1.80 | 0 | 100 | 2.2 | 60 |

Method Name: Z011_S03
Column: XBridge C18, 3 × 30 mm, 2.5 μm
Column Supplier: Waters

| Gradient/Solvent Time [min] | % Sol [H2O, 0.1% NH3] | % Sol [Acetonitrile] | Flow [ml/min] | Temp [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

Method Name: Z012_S04
Column: XBridge C18, 3 × 30 mm, 2.5 μm
Column Supplier: Waters

| Gradient/Solvent Time [min] | % Sol [H2O, 0.1% TFA] | % Sol [Acetonitrile] | Flow [ml/min] | Temp [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

Method Name: Z017_S04
Column: Stable Bond, 3 × 30 mm, 1.8 μm
Column Supplier: Agilent

| Gradient/Solvent Time [min] | % Sol [H2O, 0.1% TFA] | % Sol [Acetonitrile] | Flow [ml/min] | Temp [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

Method Name: Z018_S04
Column: Sunfire, 3 × 30 mm, 2.5 μm
Column Supplier: Waters

| Gradient/Solvent Time [min] | % Sol [H2O, 0.1% TFA] | % Sol [Acetonitrile] | Flow [ml/min] | Temp [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

Method Name: 004_CC_CA01
Column: SunFire C18_4.6 × 30 mm, 3.5 μm
Column Supplier: Waters

| Gradient/Solvent Time [min] | % Sol [H2O 0.1% TFA] | % Sol [Acetonitrile] | Flow [ml/min] | Temp [° C.] |
|---|---|---|---|---|
| 0.0 | 98.0 | 2.0 | 2.5 | 60.0 |
| 1.5 | 0.0 | 100.0 | 2.5 | 60.0 |
| 1.8 | 0.0 | 100.0 | 2.5 | 60.0 |

Method Name: 001_CA03
Column: SunFire C18_4.6 × 30 mm, 3.5 μm
Column Supplier: Waters

| Gradient/Solvent Time [min] | % Sol [Acetonitrile 0.1% TFA] | Flow [ml/min] | Temp [° C.] |
|---|---|---|---|
| 0.0 | 2.0 | 2.5 | 60.0 |
| 1.5 | 100.0 | 2.5 | 60.0 |
| 1.8 | 100.0 | 2.5 | 60.0 |

Method Name: X011_S03
Column: Xbridge BEH C18, 2.1 × 30 mm, 1.7 μm
Column Supplier: Waters

| Gradient/Solvent Time [min] | % Sol [H2O, 0.1% NH3] | % Sol [Acetonitrile] | Flow [ml/min] | Temp [° C.] |
|---|---|---|---|---|
| 0.00 | 95 | 5 | 1.3 | 60 |
| 0.02 | 95 | 5 | 1.3 | 60 |
| 1.00 | 0 | 100 | 1.3 | 60 |
| 1.10 | 0 | 100 | 1.3 | 60 |

Method Name: X012_S02
Column: Xbridge BEH C18, 2.1 × 30 mm, 1.7 μm
Column Supplier: Waters

| Gradient/Solvent Time [min] | % Sol [H2O, 0.1% TFA] | % Sol [Acetonitrile] | Flow [ml/min] | Temp [° C.] |
|---|---|---|---|---|
| 0.0 | 99 | 1 | 1.3 | 60 |
| 0.02 | 99 | 1 | 1.3 | 60 |
| 1.00 | 0 | 100 | 1.3 | 60 |
| 1.10 | 0 | 100 | 1.3 | 60 |

Method Name: V011_S01
Column: XBridge C18, 4.6 × 30 mm, 3.5 μm
Column Supplier: Waters

| Gradient/Solvent Time [min] | % Sol [H2O, 0.1% NH3] | % Sol [Acetonitrile] | Flow [ml/min] | Temp [° C.] |
|---|---|---|---|---|
| 0.0 | 97 | 3 | 5 | 60 |
| 0.2 | 97 | 3 | 5 | 60 |
| 1.6 | 0 | 100 | 5 | 60 |
| 1.7 | 0 | 100 | 5 | 60 |

Method Name: LCMS-FA-2
Column: Aquity UPLC BEH C18, 2.1 × 100 mm, 1.7 μm
Column Supplier: Waters

| Gradient/Solvent Time [min] | % Sol [H2O, 0.1% HCO2H] | % Sol [MeCN, 0.1% HCO2H] | Flow [ml/min] | Temp [° C.] |
|---|---|---|---|---|
| 0.00 | 90 | 10 | 0.4 | 40 |
| 1.00 | 90 | 10 | 0.4 | 40 |
| 4.50 | 25 | 75 | 0.4 | 40 |
| 5.50 | 25 | 75 | 0.4 | 40 |
| 6.00 | 5 | 95 | 0.4 | 40 |
| 7.00 | 5 | 95 | 0.4 | 40 |
| 7.01 | 90 | 10 | 0.4 | 40 |

Method Name: LCMS-FA-8
Column: Aquity UPLC BEH C18, 2.1 × 50 mm, 1.7 μm
Column Supplier: Waters

| Gradient/Solvent Time [min] | % Sol [H2O, 0.1% HCO2H] | % Sol [MeCN, 0.1% HCO2H] | Flow [ml/min] | Temp [° C.] |
|---|---|---|---|---|
| 0.00 | 98 | 2 | 0.4 | 40 |
| 0.80 | 98 | 2 | 0.4 | 40 |
| 2.00 | 55 | 45 | 0.4 | 40 |
| 3.00 | 25 | 75 | 0.4 | 40 |
| 3.50 | 5 | 95 | 0.4 | 40 |
| 4.00 | 0 | 100 | 0.4 | 40 |
| 5.00 | 0 | 100 | 0.4 | 40 |
| 5.01 | 98 | 2 | 0.4 | 40 |

Method Name: 5-95AB
Column: Chromolith Flash RP-18e, 25 × 2 mm, 1.5 μm
Column Supplier: Merck Milipore

| Gradient/Solvent Time [min] | % Sol [H2O, 0.0375% TFA] | % Sol [MeCN, 0.18% TFA] | Flow [ml/min] | Temp [° C.] |
|---|---|---|---|---|
| 0.00 | 95 | 5 | 1.5 | 40 |
| 0.70 | 5 | 95 | 1.5 | 40 |
| 1.15 | 5 | 95 | 1.5 | 40 |
| 1.16 | 95 | 5 | 1.5 | 40 |
| 1.60 | 5 | 95 | 1.5 | 40 |

Method Name: 0-30AB
Column: Venusil XBP-C18, 50 × 2.1 mm, 5 μm
Column Supplier: Bonna Agela

| Gradient/Solvent Time [min] | % Sol [H2O, 0.0375% TFA] | % Sol [MeCN, 0.18% TFA] | Flow [ml/min] | Temp [° C.] |
|---|---|---|---|---|
| 0.00 | 100 | 0 | 1.0 | 50 |
| 2.60 | 70 | 30 | 1.0 | 50 |
| 2.70 | 70 | 30 | 1.0 | 50 |
| 2.71 | 100 | 0 | 1.0 | 50 |
| 3.00 | 100 | 0 | 1.0 | 50 |

Preparation 1: 5-Bromo-1-isopropyl-6-methyl-4-oxo-1,4-dihydro-pyridine-3-carboxylic acid 4-(N-cyano-S-methylsulfonimidoyl)-benzylamide

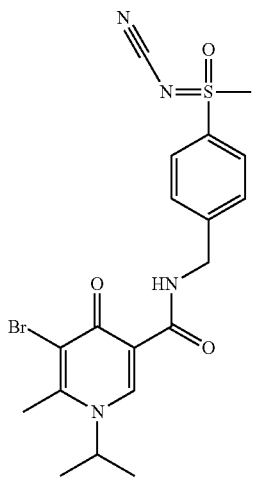

1a:
3-Dimethylaminomethylene-6-methyl-pyran-2,4-dione

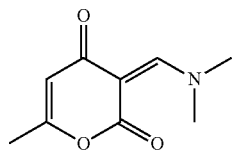

To a solution of 4-hydroxy-6-methyl-2-pyrone (11.50 g, 91.2 mmol) in toluene (30 mL) is added N,N-dimethylformamide dimethyl acetal (13.00 mL, 97.9 mmol). After stirring for 2 h at room temperature, the reaction mixture is evaporated under reduced pressure and co-evaporated with toluene several times. Yield: 18.5 g; ESI mass spectrum: [M+H]⁺=182; r.t. HPLC: 0.72 min (Z002_007).

1b: 1-Isopropyl-6-methyl-4-oxo-1,4-dihydro-pyridine-3-carboxylic acid

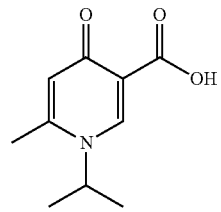

A solution of 3-dimethylaminomethylene-6-methyl-pyran-2,4-dione (preparation 1a, 10.00 g, 38.6 mmol based on 70% purity), isopropylamine (5.00 mL, 58.4 mmol) and sodium tert-butoxide (5.50 g, 57.2 mmol) in ethanol (20 mL) is heated for 18 h at 90° C. The reaction mixture is evaporated under reduced pressure, treated with water and extracted with dichloromethane. The aqueous layer is acidified with 4 N aqueous HCl and extracted with dichloromethane. The combined organic layer is washed with water, dried over Na₂SO₄ and evaporated under reduced pressure. Yield: 7.16 g; ESI mass spectrum: [M+H]⁺=196; r.t. HPLC: 0.71 min (Z002_006).

1c: 5-Bromo-1-isopropyl-6-methyl-4-oxo-1,4-dihydro-pyridine-3-carboxylic acid

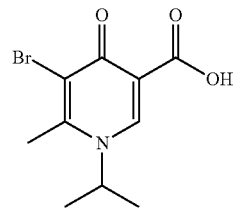

To a solution of 1-isopropyl-6-methyl-4-oxo-1,4-dihydro-pyridine-3-carboxylic acid (preparation 1b, 1.50 g, 6.92 mmol based on 90% purity) in glacial acetic acid (10 ml) is added at room temperature bromine (0.60 mL, 11.7 mmol). After stirring for 3 d at room temperature, additional bromine (1.00 mL, 19.5 mmol) is added to the reaction mixture and stirring is continued for 2 h at room temperature. The reaction mixture is diluted with water. Upon addition of dichloromethane a precipitate forms which is filtered off and dried. Yield: 2.55 g; ESI mass spectrum: [M+H]⁺=274 (bromine isotope pattern); r.t. HPLC: 0.76 min (Z002_002).

1d: 5-Bromo-1-isopropyl-6-methyl-4-oxo-1,4-dihydro-pyridine-3-carboxylic acid 4-(N-cyano-S-methylsulfonimidoyl)-benzylamide

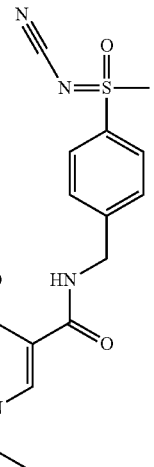

A solution of 5-bromo-1-isopropyl-6-methyl-4-oxo-1,4-dihydro-pyridine-3-carboxylic acid (preparation 1c, 270 mg, 0.99 mmol), TBTU (316 mg, 0.99 mmol) and DIPEA (513 µL, 2.97 mmol) in DMF (3.00 mL) is stirred for 10 min at room temperature. Then, a solution of (4-(N-cyano-S-methylsulfonimidoyl)phenyl)methanamine (preparation 6, 247 mg, 1.18 mmol) in DMF (1.00 mL) is added and the reaction mixture is stirred for 18 h at room temperature. The reaction mixture is purified by preparative reversed phase HPLC (Sunfire, gradient of acetonitrile in water, 0.1% TFA, 60° C.). Yield: 70 mg (15% of theory); ESI mass spectrum: [M+H]$^+$=465 (bromine isotope pattern); r.t. HPLC: 0.86 min (Z017_S04).

Preparation 2: 5-Bromo-1-ethyl-6-methyl-4-oxo-1,4-dihydro-pyridine-3-carboxylic acid 4-(N-cyano-S-methylsulfonimidoyl)-benzylamide

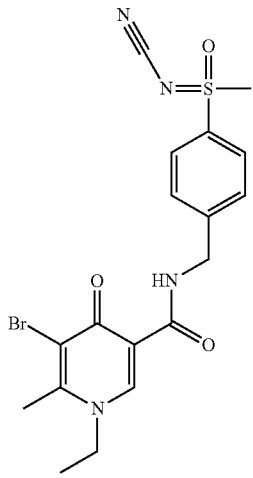 [SMILES: CCn1cc(C(=O)NCc2ccc(S(C)(=O)=NC#N)cc2)c(=O)c(Br)c1C]

2a: 1-Ethyl-6-methyl-4-oxo-1,4-dihydro-pyridine-3-carboxylic acid

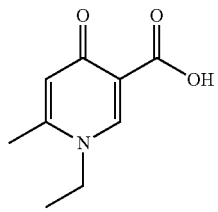

Preparation 2a is prepared following the procedure described for preparation 1b, substituting isopropylamine with ethylamine ESI mass spectrum: [M+H]$^+$=182; r.t. HPLC: 0.62 min (Z002_006).

2b: 5-Bromo-1-ethyl-6-methyl-4-oxo-1,4-dihydro-pyridine-3-carboxylic acid

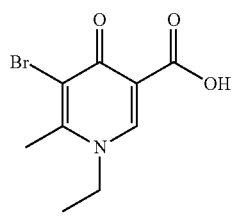

Preparation 2b is prepared following the procedure described for preparation 1c, substituting preparation 1b with preparation 2a as starting material. ESI mass spectrum: [M+H]$^+$=260 (bromine isotope pattern); r.t. HPLC: 0.89 min (Z002_007).

2c: 5-Bromo-1-ethyl-6-methyl-4-oxo-1,4-dihydro-pyridine-3-carboxylic acid 4-(N-cyano-S-methylsulfonimidoyl)-benzylamide

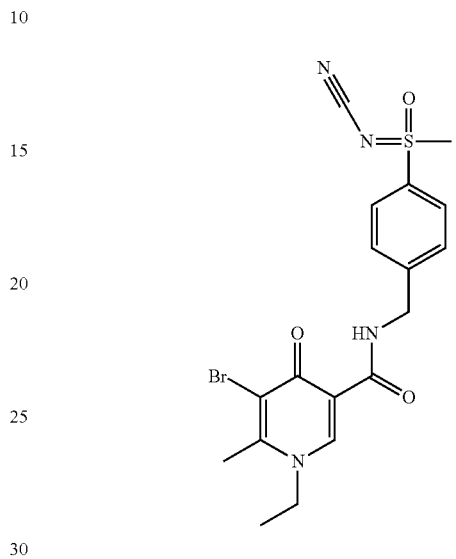

Preparation 2c is prepared following the procedure described for preparation 1d, substituting preparation 1c with preparation 2b as starting material and substituting TBTU with HBTU as coupling reagent. ESI mass spectrum: [M+H]$^+$=451 (bromine isotope pattern); r.t. HPLC: 0.81 min (Z012_S04).

Preparation 3: 5-Bromo-1-cyclobutyl-6-methyl-4-oxo-1,4-dihydro-pyridine-3-carboxylic acid 4-(N-cyano-S-methylsulfonimidoyl)-benzylamide

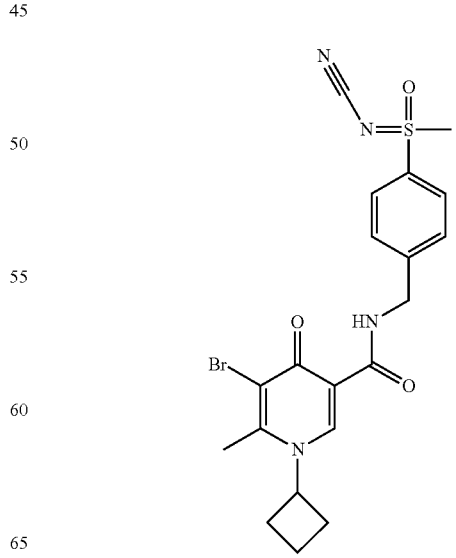

3a: 1-Cyclobutyl-6-methyl-4-oxo-1,4-dihydro-pyridine-3-carboxylic acid

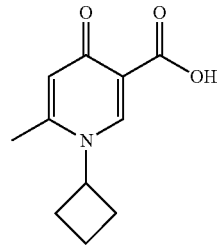

Preparation 3a is prepared following the procedure described for preparation 1b, substituting isopropylamine with cyclopropylamine. ESI mass spectrum: [M+H]⁺=208; r.t. HPLC: 0.62 min (Z002_002).

3b: 5-Bromo-1-cyclobutyl-6-methyl-4-oxo-1,4-dihydro-pyridine-3-carboxylic acid

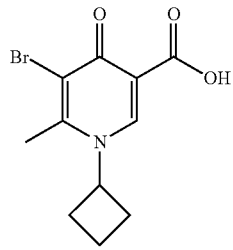 [SMILES: Cc1c(Br)c(=O)c(C(=O)O)cn1C1CCC1]

Preparation 3b is prepared following the procedure described for preparation 1c, substituting preparation 1b with preparation 3a as starting material. ESI mass spectrum: [M+H]⁺=286 (bromine isotope pattern); r.t. HPLC: 0.82 min (Z002_002).

3c: 5-Bromo-1-cyclobutyl-6-methyl-4-oxo-1,4-dihydro-pyridine-3-carboxylic acid 4-(N-cyano-S-methylsulfonimidoyl)-benzylamide

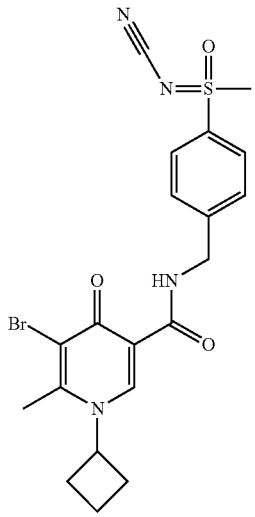 [SMILES: Cc1c(Br)c(=O)c(C(=O)NCc2ccc(S(C)(=O)=NC#N)cc2)cn1C1CCC1]

Preparation 3c is prepared following the procedure described for preparation 1d, substituting preparation 1c with preparation 3b as starting material and substituting TBTU with HBTU as coupling reagent. ESI mass spectrum: [M+H]⁺=477 (bromine isotope pattern); r.t. HPLC: 0.90 min (Z018_S04).

Preparation 4: 5-Bromo-6-methyl-1-(2-methyl-2H-pyrazol-3-yl)-4-oxo-1,4-dihydro-pyridine-3-carboxylic acid 4-(N-cyano-S-methylsulfonimidoyl)-benzylamide

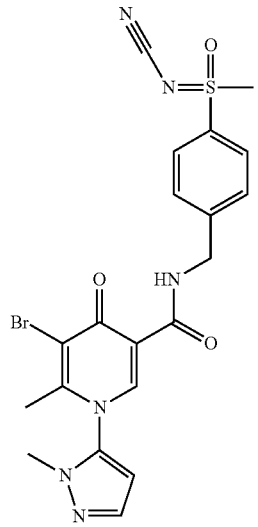

4a: 6-Methyl-1-(2-methyl-2H-pyrazol-3-yl)-4-oxo-1,4-dihydro-pyridine-3-carboxylic acid

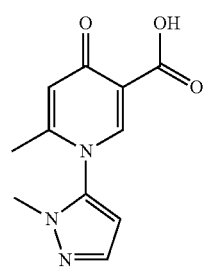 [SMILES: Cc1cc(=O)c(C(=O)O)cn1-c1ccnn1C]

Preparation 4a is prepared following the procedure described for preparation 1b, substituting isopropylamine with 1-methyl-1H-pyrazol-5-ylamine. ESI mass spectrum: [M+H]⁺=234; r.t. HPLC: 0.63 min (Z018_S04).

4b: 6-methyl-1-(2-methyl-2H-pyrazol-3-yl)-4-oxo-1,4-dihydro-pyridine-3-carboxylic acid 4-(N-cyano-S-methylsulfonimidoyl)-benzylamide

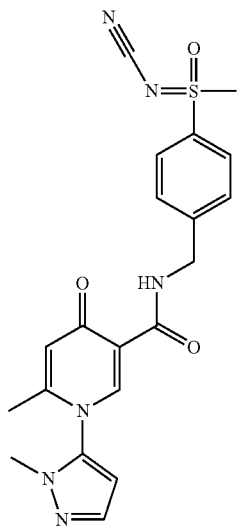

Preparation 4b is prepared following the procedure described for preparation 1d, substituting preparation 1c with preparation 4a as starting material and substituting TBTU with HBTU as coupling reagent. ESI mass spectrum: [M+H]$^+$=425; r.t. HPLC: 0.79 min (Z018_S04).

4c: 5-Bromo-6-methyl-1-(2-methyl-2H-pyrazol-3-yl)-4-oxo-1,4-dihydro-pyridine-3-carboxylic acid 4-(N-cyano-S-methylsulfonimidoyl)-benzylamide

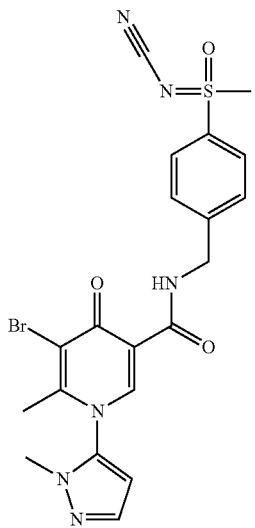 [SMILES: Cc1c(Br)c(=O)c(C(=O)NCc2ccc(S(C)(=O)=NC#N)cc2)cn1-c1ccnn1C]

To a solution of 6-methyl-1-(2-methyl-2H-pyrazol-3-yl)-4-oxo-1,4-dihydro-pyridine-3-carboxylic acid 4-(N-cyano-S-methylsulfonimidoyl)-benzylamide (preparation 4b, 150 mg, 0.118 mmol) in dichloromethane (2 mL) is added N-bromosuccinimide (21 mg, 0.35 mmol) and five drops of glacial acetic acid. After stirring for 18 h at room temperature the reaction mixture is concentrated under reduced pressure and purified by preparative reversed phase HPLC (Xbridge, gradient of acetonitrile in water, 0.1% TFA, 60° C.). Yield: 40 mg (23% of theory); ESI mass spectrum: [M+H]$^+$=503 (bromine isotope pattern); r.t. HPLC: 0.82 min (Z012_S04).

Preparation 5: 1-(4-Cyano-benzyl)-6-methyl-4-oxo-5-(3-trifluoromethyl-phenyl)-1,4-dihydro-pyridine-3-carboxylic acid

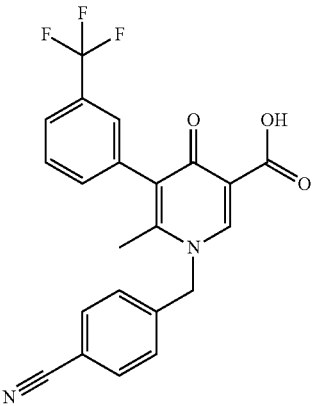

5a: 1-(4-Cyano-benzyl)-6-methyl-4-oxo-1,4-dihydro-pyridine-3-carboxylic acid

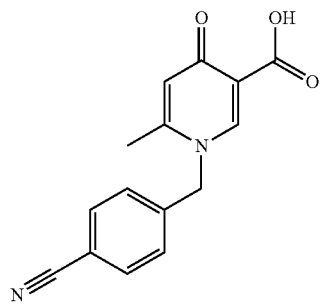 [SMILES: Cc1cc(=O)c(C(=O)O)cn1Cc1ccc(C#N)cc1]

Preparation 5a is prepared following the procedure described for preparation 1b, substituting isopropylamine with 4-cyanobenzylamine. ESI mass spectrum: [M+H]$^+$=269; r.t. HPLC: 0.86 min (Z002_005).

5b: 5-Bromo-1-(4-cyano-benzyl)-6-methyl-4-oxo-1,4-dihydro-pyridine-3-carboxylic acid

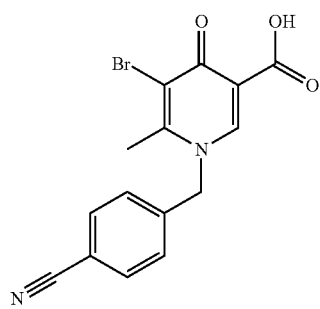 [SMILES: Cc1c(Br)c(=O)c(C(=O)O)cn1Cc1ccc(C#N)cc1]

Preparation 5b is prepared following the procedure described for preparation 1c, substituting preparation 1b with preparation 5a as starting material. ESI mass spectrum: [M+H]⁺=347 (bromine isotope pattern); r.t. HPLC: 1.07 min (Z002_005).

5c: 1-(4-Cyano-benzyl)-6-methyl-4-oxo-5-(3-trifluoromethyl-phenyl)-1,4-dihydro-pyridine-3-carboxylic acid

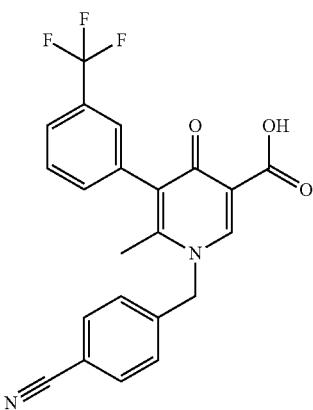 [SMILES: Cc1c(-c2cccc(C(F)(F)F)c2)c(=O)c(C(=O)O)cn1Cc1ccc(C#N)cc1]

A mixture of 5-bromo-1-(4-cyano-benzyl)-6-methyl-4-oxo-1,4-dihydro-pyridine-3-carboxylic acid (preparation 5b, 2.55 g, 7.34 mmol), 3-(trifluoromethyl)phenylboronic acid (1.65 g, 8.69 mmol), 1,1'-[bis(diphenylphosphino)ferrocene]dichloropalladium(II) (340 mg, 0.47 mmol) and Cs₂CO₃ (4.20 g, 12.9 mmol) in dioxane (20.0 mL) is heated for 72 h at 80° C. The reaction mixture is filtered over silica and the filtrate is concentrated under reduced pressure and purified by preparative reversed phase HPLC (first purification: Sunfire, gradient of methanol in water, 0.1% TFA; second purification: Xbridge, gradient of methanol in water, 0.1% NH₄OH, 60° C.). Yield: 514 mg (17% of theory); ESI mass spectrum: [M+H]⁺=413; r.t. HPLC: 1.37 min (Z002_005).

Preparation 6: (4-(N-cyano-S-methylsulfonimidoyl)phenyl)methanamine

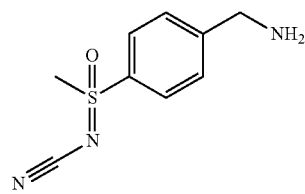

6a: 2-(4-(methylthio)benzyl)isoindoline-1,3-dione

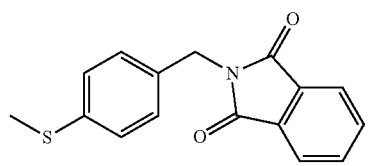

A mixture of 4-(methylthio)benzylamine (2.00 mL, 2.20 g, 14.38 mmol) and phthalic anhydride (2.39 g, 15.79 mmol) in acetic acid (40 mL, 42 g, 700 mmol) is heated at reflux for 3 h. The mixture is concentrated under reduced pressure, and the residue is partitioned between water and dichloromethane. The phases are separated, and the aqueous phase is extracted twice with dichloromethane. The combined organic layers are concentrated under reduced pressure and the residue is purified by flash chromatography on silica (gradient cyclohexane/ethyl acetate 9:1 to 7:3). Yield: 3.60 g (88% of theory); ESI mass spectrum: [M+H]⁺=284; r.t. HPLC: 0.75 min (X001_004).

6b: 2-(4-(N-cyano-S-methylsulfinimidoyl)benzyl)isoindoline-1,3-dione

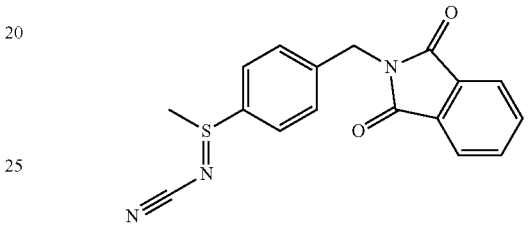

A solution of 2-(4-(methylthio)benzyl)isoindoline-1,3-dione (preparation 6a, 3.60 g, 12.71 mmol), cyanamide (694 mg, 16.5 mmol) and potassium tert-butoxide (1.71 g, 15.25 mmol) in methanol (30 mL) is treated with N-bromosuccinimide (3.39 g, 19.06 mmol). The mixture is stirred for 1 h and concentrated under reduced pressure. Saturated aqueous Na₂S₂O₃ solution is added and the mixture is extracted twice with dichloromethane. The combined organic layers are dried over Na₂SO₄ and concentrated under reduced pressure. The residue is purified by flash chromatography on silica (gradient cyclohexane/ethyl acetate 1:1 to ethyl acetate to ethyl acetate/methanol 4:1). Yield: 2.43 g (59% of theory); ESI mass spectrum: [M+H]⁺=324; r.t. HPLC: 0.52 min (X001_004).

6c: 2-(4-(N-cyano-S-methylsulfonimidoyl)benzyl)isoindoline-1,3-dione

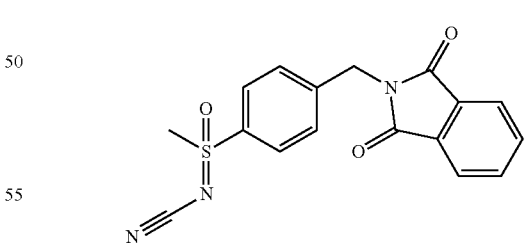

A solution of 2-(4-(N-cyano-S-methylsulfinimidoyl)benzyl)isoindoline-1,3-dione (preparation 6b, 5.75 g, 17.78 mmol) and potassium carbonate (7.37 g, 53.34 mmol) in ethanol (130 mL) is cooled at 0° C. and treated with meta-chloroperoxybenzoic acid (mCPBA, 5.98 g, 26.67 mmol). The reaction mixture is warmed to room temperature and stirred overnight before more mCPBA (2.39 g, 10.66 mmol) is added and the mixture is stirred for 4 h. Saturated aqueous Na₂S₂O₃ solution is added, and the mixture is extracted twice with dichloromethane. The combined organic layers are dried over $Na_2SO_4$ and concentrated under reduced pressure. The residue is purified by flash chromatography on silica (gradient cyclohexane/ethyl acetate 1:1 to ethyl acetate). Yield: 2.47 g (41% of theory); ESI mass spectrum: $[M+H]^+=334$; r.t. HPLC: 1.02 min (V003_003).

6d: (4-(N-cyano-S-methylsulfonimidoyl)phenyl)methanamine

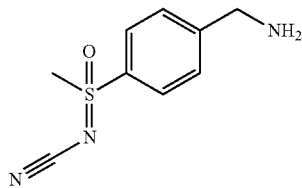

A solution of 2-(4-(N-cyano-S-methylsulfonimidoyl)benzyl)isoindoline-1,3-dione (preparation 6c, 684 mg, 2.02 mmol) and 1,2-diaminoethane (243 µL, 219 mg, 3.64 mmol) in a mixture of acetonitrile (8 mL), tetrahydrofuran (4 mL) and ethanol (4 mL) is heated at 60° C. for 5 h. All volatiles are removed under reduced pressure and the residue is suspended in dichloromethane. The mixture is filtered and the filtrate is concentrated under reduced pressure. Yield: 326 mg (77% of theory); ESI mass spectrum: $[M+H]^+=210$; r.t. HPLC: 0.223 min (V001_007).

Example 1

5-(3-Difluoromethyl-phenyl)-1-isopropyl-6-methyl-4-oxo-1,4-dihydro-pyridine-3-carboxylic acid 4-(N-cyano-S-methylsulfonimidoyl)-benzylamide

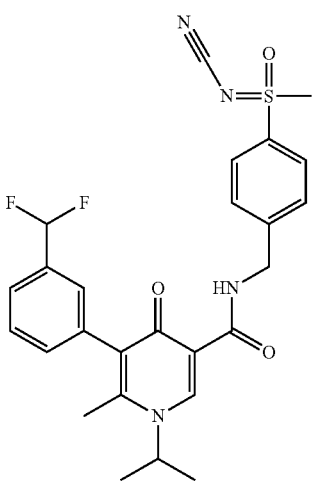 [SMILES: Cc1c(-c2cccc(C(F)F)c2)c(=O)c(C(=O)NCc2ccc(S(C)(=O)=NC#N)cc2)cn1C(C)C]

To a solution of preparation 1 (70 mg, 0.15 mmol), 3-(difluoromethyl)phenylboronic acid (36 mg, 0.21 mmol) and 1,1'-[bis(diphenylphosphino)ferrocene]dichloropalladium (II) (11 mg, 0.015 mmol) in acetonitrile (2.00 mL) is added aqueous $K_2CO_3$ solution (2 M, 0.155 mL, 0.31 mmol). After stirring for 18 h at 75° C., the reaction mixture is filtered and the filtrate is purified by preparative reversed phase HPLC (XBridge, gradient of methanol in water, 0.1% $NH_4OH$, 60° C.). Yield: 32 mg (42% of theory); ESI mass spectrum: $[M+H]^+=513$; r.t. HPLC: 0.90 min (Z003_001).

Example 1A and Example 1

Enantiomers of Example 1

63 mg of racemic example 1 are separated by chiral HPLC (Daicel IB, 250 mm×20 mm, 15% MeOH+0.2% diethylamine in supercritical $CO_2$, 40° C.).

Early eluting enantiomer (Example 1A): r.t. chiral HPLC=5.10 min (Daicel Chiralcel®OZ-H 4.6 mm×250 mm, 5 µm, 4 ml/min, 10 min, 40% MeOH+0.2% diethylamine in supercritical $CO_2$, 40° C., 100 bar back pressure); ESI mass spectrum: $[M+H]^+=513$; Yield: 23 mg Late eluting enantiomer (Example 1B): r.t. chiral HPLC=7.80 min (Daicel Chiralcel®OZ-H 4.6 mm×250 mm, 5 µm, 4 ml/min, 10 min, 40% MeOH+0.2% diethylamine in supercritical $CO_2$, 40° C., 100 bar back pressure); ESI mass spectrum: $[M+H]^+=513$; Yield: 20 mg Example 2

1-Isopropyl-6-methyl-4-oxo-5-(3-trifluoromethyl-phenyl)-1,4-dihydro-pyridine-3-carboxylic acid 4-(N-cyano-S-methylsulfonimidoyl)-benzylamide

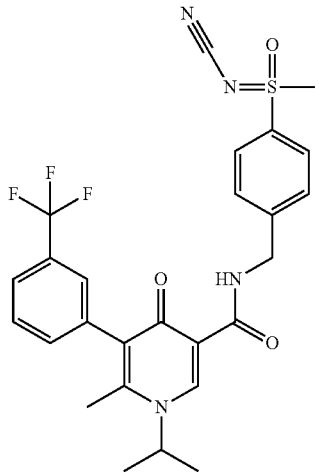 [SMILES: Cc1c(-c2cccc(C(F)(F)F)c2)c(=O)c(C(=O)NCc2ccc(S(C)(=O)=NC#N)cc2)cn1C(C)C]

Example 2 is prepared following the procedure described for example 1, substituting 3-(difluoromethyl)phenylboronic acid with 3-(trifluoromethyl)phenylboronic acid. ESI mass spectrum: $[M+H]^+=531$; r.t. HPLC: 0.99 min (Z003_001).

Example 2A and Example 2B

Enantiomers of Example 2

100 mg of racemic example 2 are separated by chiral HPLC (Daicel OZ-H, 250 mm×20 mm, 40% MeOH+0.2% diethylamine in supercritical $CO_2$, 40° C.).

Early eluting enantiomer (Example 2A): r.t. chiral HPLC=3.62 min (Daicel Chiralcel®OZ-H 4.6 mm×250 mm, 5 µm, 4 ml/min, 10 min, 40% MeOH+0.2% diethylamine in supercritical $CO_2$, 40° C., 100 bar back pressure); ESI mass spectrum: $[M+H]^+=531$; Yield: 41 mg Late eluting enantiomer (Example 2B): r.t. chiral HPLC=5.23 min (Daicel Chiralcel®OZ-H 4.6 mm×250 mm, 5 µm, 4 ml/min, 10 min, 40% MeOH+0.2% diethylamine in supercritical $CO_2$, 40° C., 100 bar back pressure); ESI mass spectrum: $[M+H]^+=531$; Yield: 43 mg.

Example 3

1-Isopropyl-2-methyl-4-oxo-2'-trifluoromethyl-1,4-dihydro-[3,4']-bipyridinyl-5-carboxylic acid 4-(N-cyano-S-methylsulfonimidoyl)-benzylamide

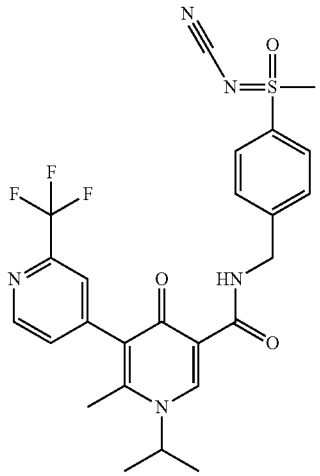 [SMILES: Cc1c(-c2ccnc(C(F)(F)F)c2)c(=O)c(C(=O)NCc2ccc(S(C)(=O)=NC#N)cc2)cn1C(C)C]

Example 3 is prepared following the procedure described for example 1, substituting 3-(difluoromethyl)phenylboronic acid with 2-(trifluoromethyl)pyridine-4-boronic acid. ESI mass spectrum: [M+H]$^+$=532; r.t. HPLC: 0.86 min (Z003_001).

Example 3A and Example 3B

Enantiomers of Example 3

50 mg of racemic example 3 are separated by chiral HPLC (Daicel IB, 250 mm×20 mm, 15% MeOH+0.2% diethylamine in supercritical $CO_2$, 40° C.).

Early eluting enantiomer (Example 3A): r.t. chiral HPLC=2.81 min (Daicel Chiralcel®OZ-H 4.6 mm×250 mm, 5 μm, 4 ml/min, 10 min, 40% MeOH+0.2% diethylamine in supercritical $CO_2$, 40° C., 100 bar back pressure); ESI mass spectrum: [M+H]$^+$=532; Yield: 23 mg.

Late eluting enantiomer (Example 3B): r.t. chiral HPLC=4.25 min (Daicel Chiralcel®OZ-H 4.6 mm×250 mm, 5 μm, 4 ml/min, 10 min, 40% MeOH+0.2% diethylamine in supercritical $CO_2$, 40° C., 100 bar back pressure); ESI mass spectrum: [M+H]$^+$=532; Yield: 20 mg.

Example 4

1-Ethyl-6-methyl-4-oxo-5-(3-trifluoromethyl-phenyl)-1,4-dihydro-pyridine-3-carboxylic acid 4-(N-cyano-S-methylsulfonimidoyl)-benzylamide

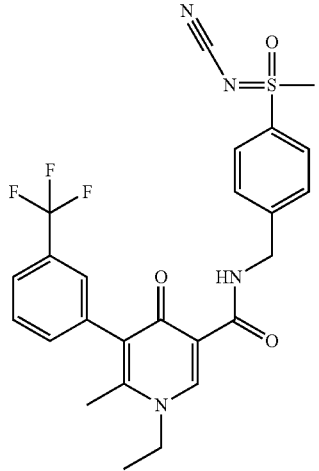 [SMILES: CCn1cc(C(=O)NCc2ccc(S(C)(=O)=NC#N)cc2)c(=O)c(-c2cccc(C(F)(F)F)c2)c1C]

Example 4 is prepared following the procedure described for example 1, substituting 3-(difluoromethyl)phenylboronic acid with 2-(trifluoromethyl)pyridine-4-boronic acid and substituting preparation 1 with preparation 2 as starting material. ESI mass spectrum: [M+H]$^+$=517; r.t. HPLC: 0.85 min (Z011_S03).

Example 4A and Example 4B

Enantiomers of Example 4

30 mg of racemic example 4 are separated by chiral HPLC (Daicel OZH, 250 mm×20 mm, 40% MeOH+0.2% diethylamine in supercritical $CO_2$, 40° C.).

Early eluting enantiomer (Example 4A): r.t. chiral HPLC=5.08 min (Daicel Chiralpak®IB, 4.6 mm×250 mm, 5 μm, 4 ml/min, 10 min, 20% MeOH+0.2% diethylamine in supercritical $CO_2$, 40° C., 150 bar back pressure); ESI mass spectrum: [M+H]$^+$=517; Yield: 11 mg.

Late eluting enantiomer (Example 4B): r.t. chiral HPLC=5.47 min (Daicel Chiralpak®IB, 4.6 mm×250 mm, 5 μm, 4 ml/min, 10 min, 20% MeOH+0.2% diethylamine in supercritical $CO_2$, 40° C., 150 bar back pressure); ESI mass spectrum: [M+H]$^+$=517; Yield: 9 mg.

Example 5

5-(3-Difluoromethyl-phenyl)-1-ethyl-6-methyl-4-oxo-1,4-dihydro-pyridine-3-carboxylic acid 4-(N-cyano-S-methylsulfonimidoyl)-benzylamide

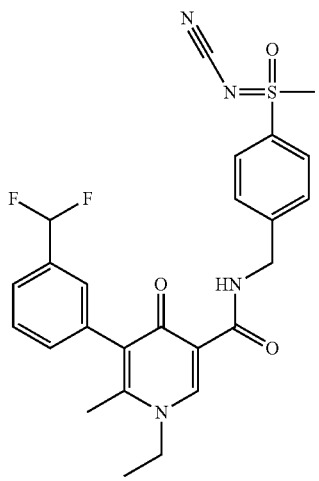 [SMILES: CCn1cc(C(=O)NCc2ccc(S(C)(=O)=NC#N)cc2)c(=O)c(-c2cccc(C(F)F)c2)c1C]

Example 5 is prepared following the procedure described for example 1, substituting preparation 1 with preparation 2 as starting material. ESI mass spectrum: [M+H]$^+$=499; r.t. HPLC: 0.79 min (Z011_S03).

Example 6

5-(3-Difluoromethyl-phenyl)-1-cyclobutyl-6-methyl-4-oxo-1,4-dihydro-pyridine-3-carboxylic acid 4-(N-cyano-S-methylsulfonimidoyl)-benzylamide

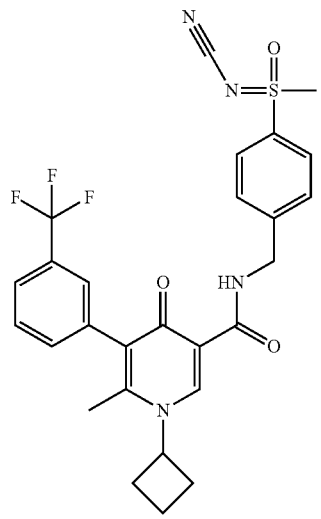 [SMILES: Cc1c(-c2cccc(C(F)(F)F)c2)c(=O)c(C(=O)NCc2ccc(S(C)(=O)=NC#N)cc2)cn1C1CCC1]

Example 6 is prepared following the procedure described for example 1, substituting preparation 1 with preparation 3 as starting material. ESI mass spectrum: [M+H]$^+$=525; r.t. HPLC: 0.84 min (Z011_S03).

Example 7

5-(3-Difluoromethyl-phenyl)-6-methyl-1-(2-methyl-2H-pyrazol-3-yl)-4-oxo-1,4-dihydro-pyridine-3-carboxylic acid 4-(N-cyano-S-methylsulfonimidoyl)-benzylamide

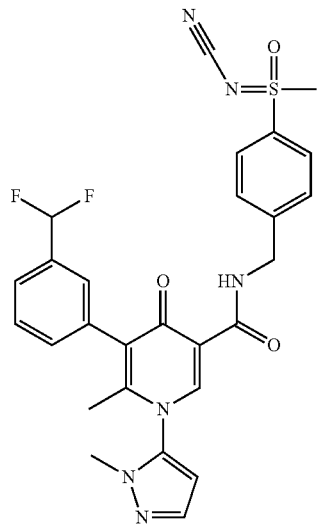 [SMILES: Cc1c(-c2cccc(C(F)F)c2)c(=O)c(C(=O)NCc2ccc(S(C)(=O)=NC#N)cc2)cn1-c1ccnn1C]

Example 7 is prepared following the procedure described for example 1, substituting preparation 1 with preparation 4 as starting material. ESI mass spectrum: [M+H]$^+$=551; r.t. HPLC: 0.96 min (Z018_S04).

Example 8

6-Methyl-1-(2-methyl-2H-pyrazol-3-yl)-4-oxo-5-(3-trifluoromethyl-phenyl)-1,4-dihydro-pyridine-3-carboxylic acid 4-(N-cyano-S-methylsulfonimidoyl)-benzylamide

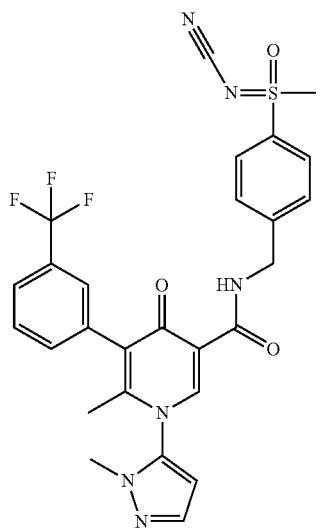 [SMILES: Cc1c(-c2cccc(C(F)(F)F)c2)c(=O)c(C(=O)NCc2ccc(S(C)(=O)=NC#N)cc2)cn1-c1ccnn1C]

Example 8 is prepared following the procedure described for example 1, substituting 3-(difluoromethyl)phenylboronic acid with 3-(trifluoromethyl)phenylboronic acid and substituting preparation 1 with preparation 4 as starting material. ESI mass spectrum: [M+H]$^+$=569; r.t. HPLC: 1.00 min (Z018_S04).

Example 9

1-(4-Cyano-benzyl)-6-methyl-4-oxo-5-(3-trifluoromethyl-phenyl)-1,4-dihydro-pyridine-3-carboxylic acid 4-(N-cyano-S-methylsulfonimidoyl)-benzylamide

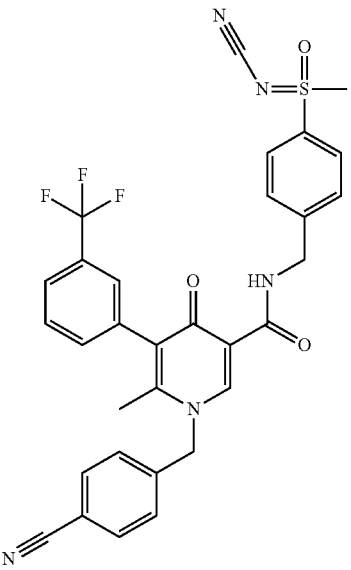 [SMILES: Cc1c(-c2cccc(C(F)(F)F)c2)c(=O)c(C(=O)NCc2ccc(S(C)(=O)=NC#N)cc2)cn1Cc1ccc(C#N)cc1]

Example 9 is prepared following the procedure described for preparation 1d, substituting preparation 1c with preparation 5 as starting material. ESI mass spectrum: [M+H]$^+$=604; r.t. HPLC: 0.63 min (X012_S01).

Example 9A and Example 9B

Enantiomers of Example 9

58 mg of racemic example 9 are separated by chiral HPLC (Daicel ASH, 250 mm×20 mm, 20% MeOH+0.2% diethylamine in supercritical $CO_2$, 40° C.).

Early eluting enantiomer (Example 9A): r.t. chiral HPLC=5.76 min (Daicel Chiralpak®ASH, 250 mm×4.6 mm, 5 μm, 4 ml/min, 10 min, 20% MeOH+0.2% diethylamine in supercritical $CO_2$, 40° C., 150 bar back pressure); ESI mass spectrum: $[M+H]^+$=604; Yield: 8 mg Late eluting enantiomer (Example 9B): r.t. chiral HPLC=6.86 min (Daicel Chiralpak®ASH, 250 mm×4.6 mm, 5 μm, 4 ml/min, 10 min, 20% MeOH+0.2% diethylamine in supercritical $CO_2$, 40° C., 150 bar back pressure); ESI mass spectrum: $[M+H]^+$=604; Yield: 7 mg The following intermediates are prepared as described for preparation 1b, substituting isopropylamine with the appropriate amine.

| Preparation | Structure | MS $[M + H]^+$ | r.t. HPLC/ Method |
|---|---|---|---|
| 7.1 | 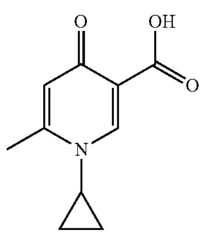 | 194 | 0.52 min Z002_002 |
| 7.2 | 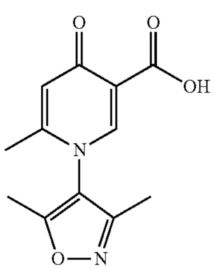 [SMILES: Cc1noc(C)c1-n1cc(C(=O)O)c(=O)cc1C] | 249 | 0.68 min Z018_S04 |
| 7.3 | 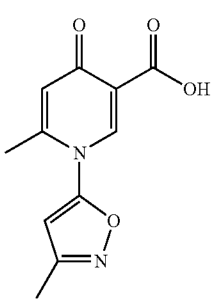 [SMILES: Cc1cc(-n2cc(C(=O)O)c(=O)cc2C)on1] | 235 | 0.70 min Z018_S04 |
| 7.4 | 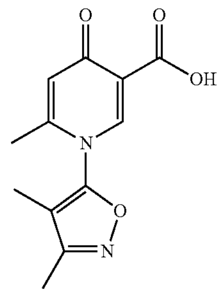 [SMILES: Cc1noc(-n2cc(C(=O)O)c(=O)cc2C)c1C] | 249 | 0.76 min Z018_S04 |
| 7.5 | 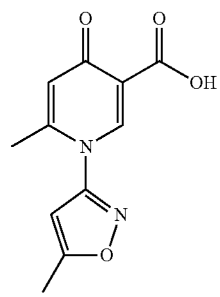 [SMILES: Cc1cc(-n2cc(C(=O)O)c(=O)cc2C)no1] | 235 | 0.74 min Z018_S04 |
| 7.6 | 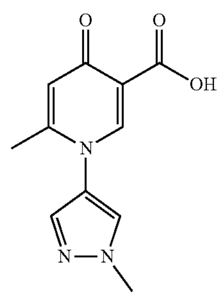 [SMILES: Cc1cc(=O)c(C(=O)O)cn1-c1cnn(C)c1] | 234 | 0.60 min Z018_S04 |
| 7.7 | 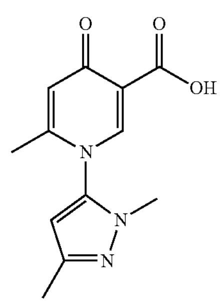 [SMILES: Cc1cc(-n2cc(C(=O)O)c(=O)cc2C)n(C)n1] | 248 | 0.71 min Z018_S04 |
| 7.8 | 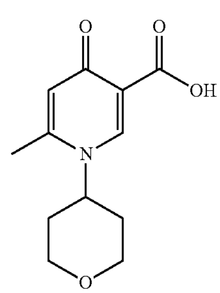 [SMILES: Cc1cc(=O)c(C(=O)O)cn1C1CCOCC1] | 238 | 0.58 min Z018_S04 |

| Preparation | Structure | MS [M + H]+ | r.t. HPLC/ Method |
|---|---|---|---|
| 7.9 | 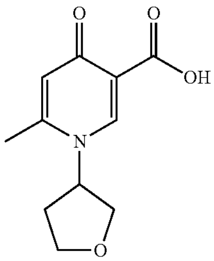 [SMILES: Cc1cc(=O)c(C(=O)O)cn1C1CCOC1] | 224 | 0.54 min Z018_S04 |
| 7.10 | 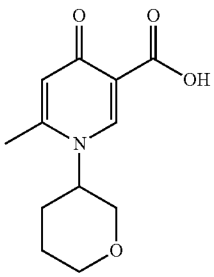 [SMILES: Cc1cc(=O)c(C(=O)O)cn1C1CCCOC1] | 238 | 0.64 min Z018_S04 |
| 7.11 | 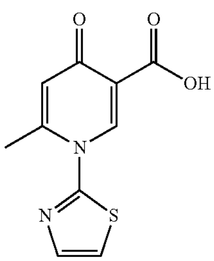 [SMILES: Cc1cc(=O)c(C(=O)O)cn1-c1nccs1] | 237 | 0.65 min Z018_S04 |
| 7.12 | 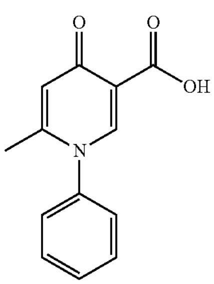 [SMILES: Cc1cc(=O)c(C(=O)O)cn1-c1ccccc1] | 230 | 0.75 min Z018_S04 |
| 7.13 | 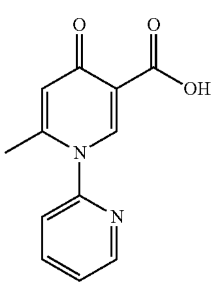 | 231 | 0.65 min Z018_S04 |
| 7.14 | 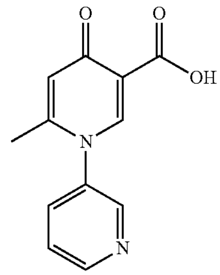 [SMILES: Cc1cc(=O)c(C(=O)O)cn1-c1cccnc1] | 231 | 0.54 min Z018_S04 |
| 7.15 | 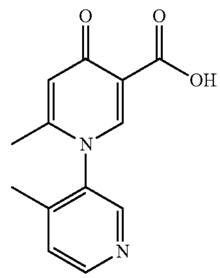 [SMILES: Cc1ccncc1-n1cc(C(=O)O)c(=O)cc1C] | 245 | 0.59 min Z018_S04 |
| 7.16 | 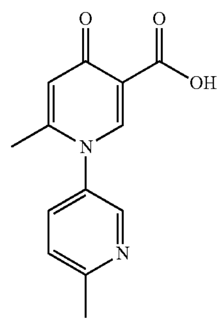 [SMILES: Cc1ccc(-n2cc(C(=O)O)c(=O)cc2C)cn1] | 245 | 0.60 min Z018_S04 |
| 7.17 | 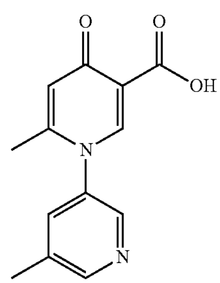 [SMILES: Cc1cncc(-n2cc(C(=O)O)c(=O)cc2C)c1] | 245 | 0.63 min Z018_S04 |
| 7.18 | 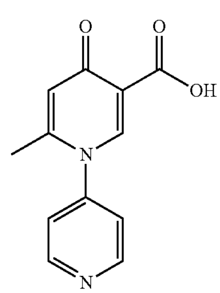 [SMILES: Cc1cc(=O)c(C(=O)O)cn1-c1ccncc1] | 231 | 0.48 min Z018_S04 |

-continued

| Preparation | Structure | MS [M + H]+ | r.t. HPLC/ Method |
|---|---|---|---|
| 7.19 | (6-methyl-1-(pyrimidin-5-yl)-4-oxo-1,4-dihydropyridine-3-carboxylic acid) | 232 | 0.35 min Z018_S04 |

The following bromo intermediates are prepared as described for preparation 1c, employing the appropriate desbromo intermediates as starting material.

| Preparation | Starting material | Structure | MS [M + H]+ | r.t. HPLC/ Method |
|---|---|---|---|---|
| 8.1 | Preparation 7.1 | (5-bromo-1-cyclopropyl-6-methyl-4-oxo-1,4-dihydropyridine-3-carboxylic acid) | 272 (Br pattern) | 0.76 min Z018_S04 |
| 8.2 | Preparation 7.2 | (5-bromo-1-(3,5-dimethylisoxazol-4-yl)-6-methyl-4-oxo) | 327 (Br pattern) | 0.84 min Z018_S04 |
| 8.3 | Preparation 7.3 | (5-bromo-6-methyl-1-(3-methylisoxazol-5-yl)-4-oxo) | 313 (Br pattern) | 0.83 min Z018_S04 |
| 8.4 | Preparation 7.4 | (5-bromo-1-(3,4-dimethylisoxazol-5-yl)-6-methyl) | 327 (Br pattern) | 0.87 min Z018_S04 |
| 8.5 | Preparation 7.5 | (5-bromo-6-methyl-1-(5-methylisoxazol-3-yl)-4-oxo) | 313 (Br pattern) | 0.85 min Z018_S04 |
| 8.6 | Preparation 7.6 | (5-bromo-6-methyl-1-(1-methyl-1H-pyrazol-4-yl)-4-oxo) | 312 (Br pattern) | 0.81 min Z018_S04 |
| 8.7 | Preparation 7.7 | (5-bromo-1-(1,3-dimethyl-1H-pyrazol-5-yl)-6-methyl) | 326 (Br pattern) | 0.83 min Z018_S04 |
| 8.8 | Preparation 7.8 | (5-bromo-6-methyl-4-oxo-1-(tetrahydro-2H-pyran-4-yl)) | 316 (Br pattern) | 0.72 min Z017_S04 |
| 8.9 | Preparation 7.9 | (5-bromo-6-methyl-4-oxo-1-(tetrahydrofuran-3-yl)) | 302 (Br pattern) | 0.68 min Z017_S04 |

-continued

| Preparation | Starting material | Structure | MS [M + H]+ | r.t. HPLC/Method |
|---|---|---|---|---|
| 8.10 | Preparation 7.10 | 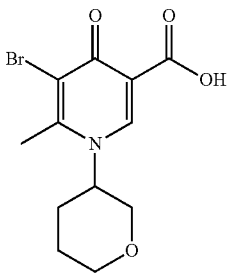 [SMILES: Cc1c(Br)c(=O)c(C(=O)O)cn1C1CCCOC1] | 316 (Br pattern) | 0.78 min Z018_S04 |
| 8.11 | Preparation 7.11 | 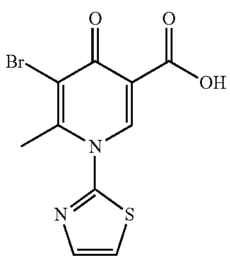 [SMILES: Cc1c(Br)c(=O)c(C(=O)O)cn1-c1nccs1] | 315 (Br pattern) | 0.80 min Z018_S04 |
| 8.12 | Preparation 7.12 | 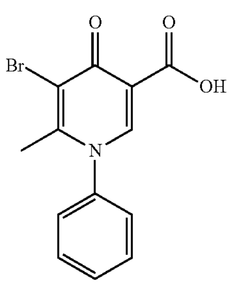 [SMILES: Cc1c(Br)c(=O)c(C(=O)O)cn1-c1ccccc1] | 308 (Br pattern) | 0.87 min Z018_S04 |
| 8.13 | Preparation 7.13 | 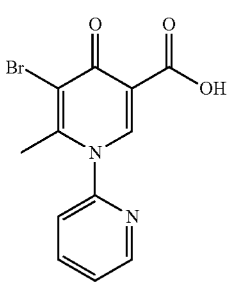 [SMILES: Cc1c(Br)c(=O)c(C(=O)O)cn1-c1ccccn1] | 309 (Br pattern) | 0.80 min Z018_S04 |
| 8.14 | Preparation 7.14 | 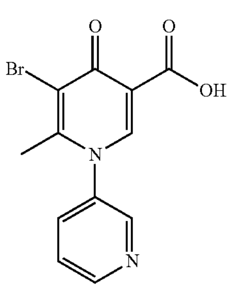 [SMILES: Cc1c(Br)c(=O)c(C(=O)O)cn1-c1cccnc1] | 309 (Br pattern) | 0.71 min Z018_S04 |
| 8.15 | Preparation 7.15 | 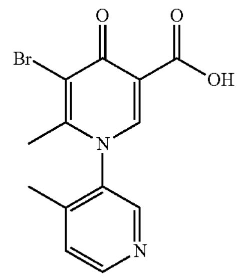 [SMILES: Cc1ccncc1-n1cc(C(=O)O)c(=O)c(Br)c1C] | 323 (Br pattern) | 0.75 min Z018_S04 |
| 8.16 | Preparation 7.16 | 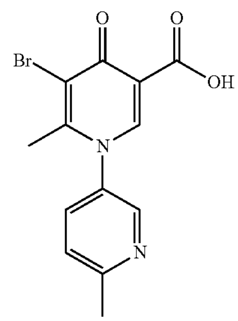 [SMILES: Cc1ccc(-n2cc(C(=O)O)c(=O)c(Br)c2C)cn1] | 323 (Br pattern) | 0.74 min Z018_S04 |
| 8.17 | Preparation 7.17 | 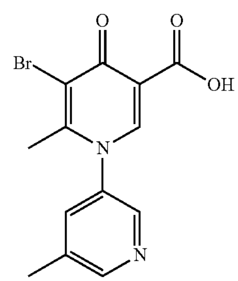 [SMILES: Cc1cncc(-n2cc(C(=O)O)c(=O)c(Br)c2C)c1] | 323 (Br pattern) | 0.78 min Z018_S04 |
| 8.18 | Preparation 7.18 | 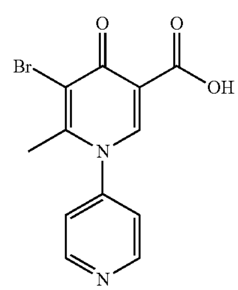 | 309 (Br pattern) | 0.68 min Z018_S04 |
| 8.19 | Preparation 7.19 | 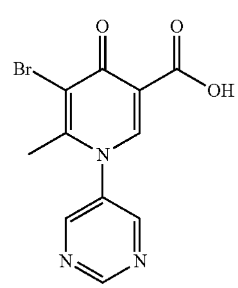 [SMILES: Cc1c(Br)c(=O)c(C(=O)O)cn1-c1cncnc1] | 310 (Br pattern) | 0.65 min Z018_S04 |

Preparation 8.20: 5-Bromo-6-methyl-1-(2-methyl-2H-pyrazol-3-yl)-4-oxo-1,4-dihydro-pyridine-3-carboxylic acid methyl ester

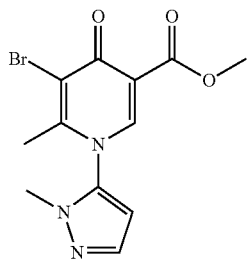

8.20a 6-Methyl-1-(2-methyl-2H-pyrazol-3-yl)-4-oxo-1,4-dihydro-pyridine-3-carboxylic acid methyl ester

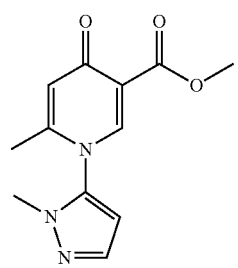

To a solution of preparation 4a (1.8 g, 90% purity, 6.95 mmol) in methanol (5 mL) is added slowly thionyl chloride (1.64 g, 13.8 mmol) at 0° C. The reaction mixture is stirred at 70° C. for 1.5 h, concentrated under reduced pressure and purified by reversed-phase HPLC (Gilson: Sunfire, 30° C., gradient of acetonitrile in water+0.1% formic acid). Yield: 199 mg (12% of theory). ESI mass spectrum: [M+H]$^+$=248; r.t. HPLC: 0.56 min (Z018_S04).

8.20b 5-Bromo-6-methyl-1-(2-methyl-2H-pyrazol-3-yl)-4-oxo-1,4-dihydro-pyridine-3-carboxylic acid methyl ester

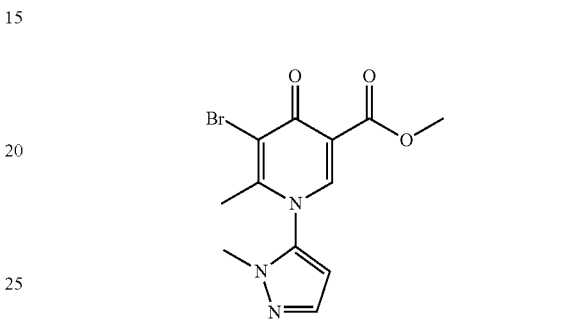

The title compound is prepared as described for preparation 4c, substituting preparation 4b with preparation 8.20a as starting material. ESI mass spectrum: [M+H]$^+$=326 (bromine pattern); r.t. HPLC: 0.69 min (Z012_S04).

The following intermediates are prepared as described for Example 2, substituting preparation 1 with the appropriate bromo intermediate as starting material.

| Preparation | Starting Material | Structure | MS [M + H]$^+$ | r.t. HPLC Method |
|---|---|---|---|---|
| 9.1 | Prep. 2b | 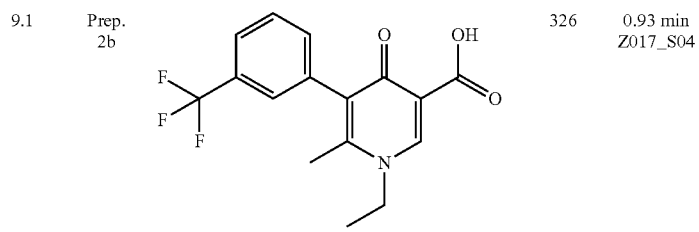 | 326 | 0.93 min Z017_S04 |
| 9.2 | Prep. 1c | 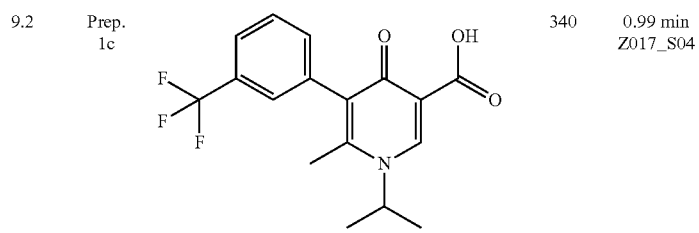 | 340 | 0.99 min Z017_S04 |

-continued
| Preparation | Starting Material | Structure | MS [M + H]+ | r.t. HPLC Method |
|---|---|---|---|---|
| 9.3 | Prep. 8.20 | 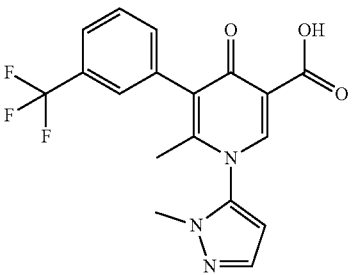 [SMILES: Cc1c(-c2cccc(C(F)(F)F)c2)c(=O)c(C(=O)O)cn1-c1ccnn1C] | 378 | 0.98 min Z018_S04 |
| 9.4 | Prep. 8.1 | 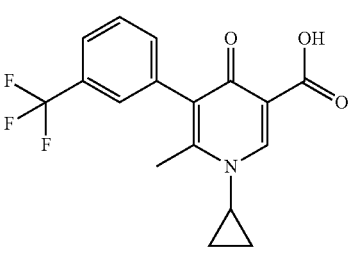 [SMILES: Cc1c(-c2cccc(C(F)(F)F)c2)c(=O)c(C(=O)O)cn1C1CC1] | 338 | 0.98 min Z018_S04 |
| 9.5 | Prep. 8.2 | 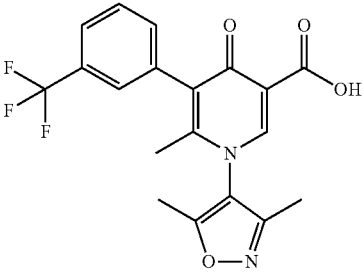 [SMILES: Cc1noc(C)c1-n1cc(C(=O)O)c(=O)c(-c2cccc(C(F)(F)F)c2)c1C] | 393 | 1.05 min Z018_S04 |
| 9.6 | Prep. 8.12 | 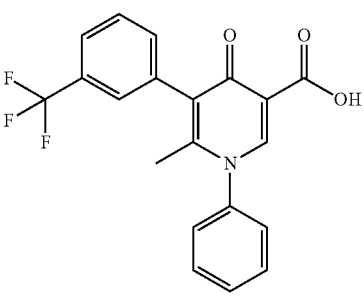 [SMILES: Cc1c(-c2cccc(C(F)(F)F)c2)c(=O)c(C(=O)O)cn1-c1ccccc1] | 374 | 1.06 min Z018_S04 |
| 9.7 | Prep. 8.13 | 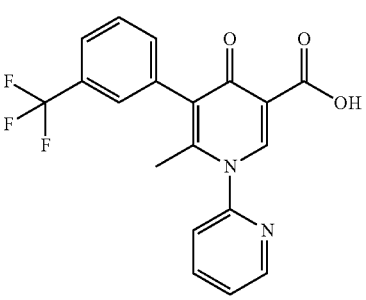 | 375 | 1.00 min Z018_S04 |

-continued

| Preparation | Starting Material | Structure | MS [M + H]+ | r.t. HPLC Method |
|---|---|---|---|---|
| 9.8 | Prep. 8.14 | (structure: 5-(3-trifluoromethylphenyl)-6-methyl-4-oxo-1-(pyridin-3-yl)-1,4-dihydropyridine-3-carboxylic acid) | 375 | 0.96 min Z018_S04 |
| 9.9 | Prep. 8.18 | (structure: 5-(3-trifluoromethylphenyl)-6-methyl-4-oxo-1-(pyridin-4-yl)-1,4-dihydropyridine-3-carboxylic acid) | 375 | 0.93 min Z018_S04 |
| 9.10 | Prep. 8.19 | (structure: 5-(3-trifluoromethylphenyl)-6-methyl-4-oxo-1-(pyrimidin-5-yl)-1,4-dihydropyridine-3-carboxylic acid) | 376 | 0.93 min Z018_804 |

The following intermediates are prepared as described for Example 1, substituting preparation 1 with the appropriate bromo intermediate as starting material.

| Preparation | Starting Material | Structure | MS [M + H]+ | r.t. HPLC Method |
|---|---|---|---|---|
| 9.11 | Prep. 2b | (structure: 5-(3-difluoromethylphenyl)-1-ethyl-6-methyl-4-oxo-1,4-dihydropyridine-3-carboxylic acid) | 308 | 0.89 min Z018_S04 |

-continued

| Preparation | Starting Material | Structure | MS [M + H]+ | r.t. HPLC Method |
|---|---|---|---|---|
| 9.12 | Prep. 1c | 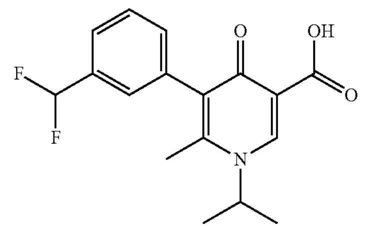 [SMILES: Cc1c(-c2cccc(C(F)F)c2)c(=O)c(C(=O)O)cn1C(C)C] | 322 | 0.90 min Z018_S04 |
| 9.13 | Prep. 8.20 | 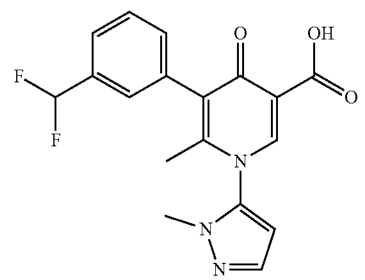 [SMILES: Cc1c(-c2cccc(C(F)F)c2)c(=O)c(C(=O)O)cn1-c1ccnn1C] | 360 | 0.50 min Z011_S03 |
| 9.14 | Prep. 8.12 | 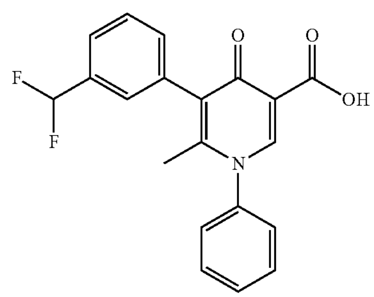 [SMILES: Cc1c(-c2cccc(C(F)F)c2)c(=O)c(C(=O)O)cn1-c1ccccc1] | 356 | 1.00 min Z018_S04 |
| 9.15 | Prep. 8.14 | 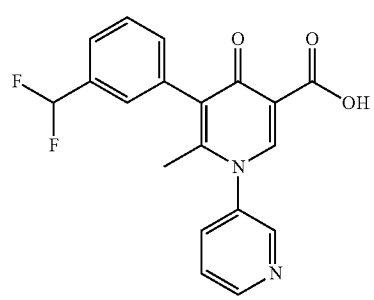 | 357 | 0.88 min Z018_S04 |
| 9.16 | Prep. 8.18 | 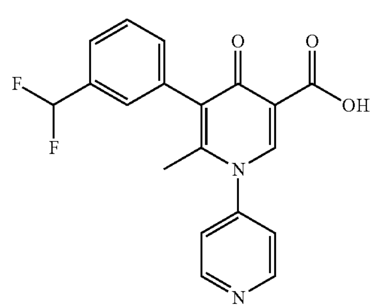 [SMILES: Cc1c(-c2cccc(C(F)F)c2)c(=O)c(C(=O)O)cn1-c1ccncc1] | 357 | 0.86 min Z018_S04 |

The following intermediates are prepared as described for Example 1, substituting preparation 1 with preparation 1c and employing the appropriate boronic acid or ester in the Suzuki reaction.

| Preparation | Boronic Acid or Ester | Structure | MS [M + H]+ | r.t. HPLC Method |
|---|---|---|---|---|
| 9.17 | 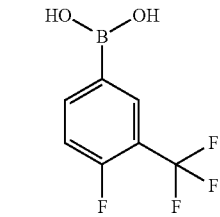 | 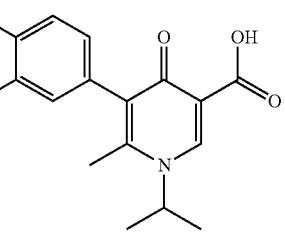 | 358 | 1.01 min Z018_S04 |
| 9.18 | 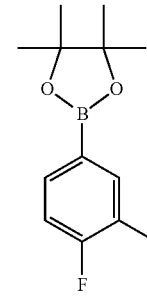 | 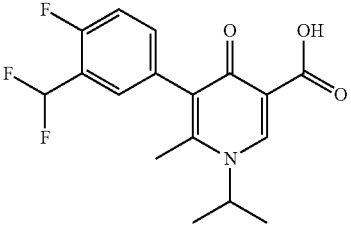 [SMILES: Cc1c(-c2ccc(F)c(C(F)F)c2)c(=O)c(C(=O)O)cn1C(C)C] | 340 | 0.93 min Z018_S04 |

The following intermediates are prepared as described for Example 3, substituting preparation 1 with the appropriate bromo intermediate as starting material.

| Preparation | Starting Material | Structure | MS [M + H]+ | r.t. HPLC Method |
|---|---|---|---|---|
| 9.19 | Prep. 8.12 | 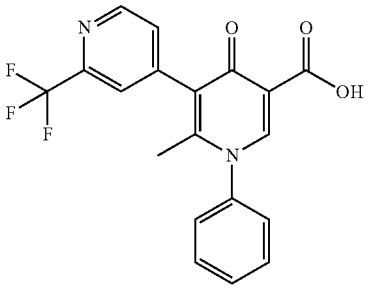 [SMILES: Cc1c(-c2ccnc(C(F)(F)F)c2)c(=O)c(C(=O)O)cn1-c1ccccc1] | 375 | 0.98 min Z018_S04 |
| 9.20 | Prep. 8.13 | 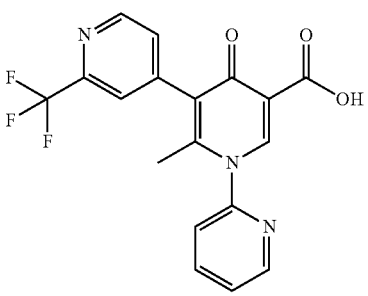 [SMILES: Cc1c(-c2ccnc(C(F)(F)F)c2)c(=O)c(C(=O)O)cn1-c1ccccn1] | 376 | 0.90 min Z018_S04 |

-continued

| Preparation | Starting Material | Structure | MS [M + H]+ | r.t. HPLC Method |
|---|---|---|---|---|
| 9.21 | Prep. 8.14 | 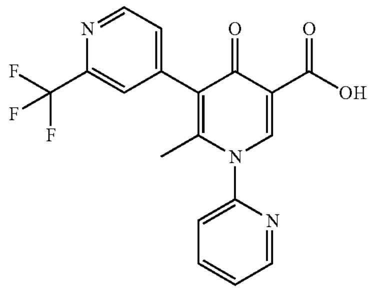 [SMILES: Cc1c(-c2ccnc(C(F)(F)F)c2)c(=O)c(C(=O)O)cn1-c1ccccn1] | 376 | 0.85 min Z018_S04 |
| 9.22 | Prep. 8.18 | 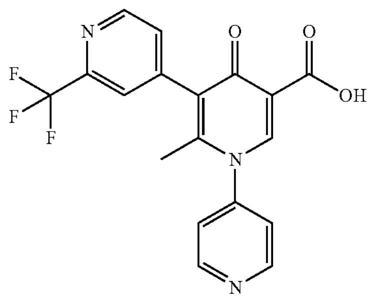 [SMILES: Cc1c(-c2ccnc(C(F)(F)F)c2)c(=O)c(C(=O)O)cn1-c1ccncc1] | 376 | 0.83 min Z018_S04 |

The following intermediates are prepared as described for preparation 1d, substituting preparation 1c with the appropriate starting material acid and substituting racemic preparation 6 with enantiomerically pure preparation 12B. The asterisk in the structures indicates that the compound is prepared from the enantiomer preparation 12B.

| Preparation | Starting Material Acid | Structure | MS [M + H]+ | r.t. HPLC Method |
|---|---|---|---|---|
| 10.1 | Prep. 8.3 | 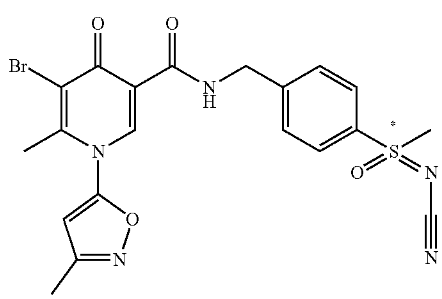 [SMILES: Cc1cc(-n2cc(C(=O)NCc3ccc(S(C)(=O)=NC#N)cc3)c(=O)c(Br)c2C)on1] | 504 (Br pattern) | 0.75 min Z011_S03 |
| 10.2 | Prep. 8.4 | 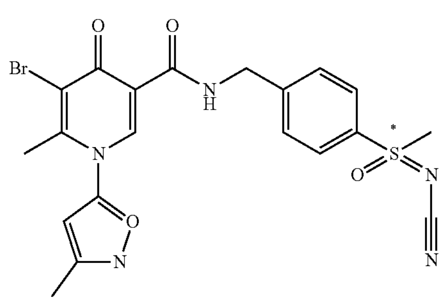 | 518 (Br pattern) | 0.77 min Z011_S03 |

| Preparation | Starting Material Acid | Structure | MS [M + H]+ | r.t. HPLC Method |
|---|---|---|---|---|
| 10.3 | Prep. 8.5 | 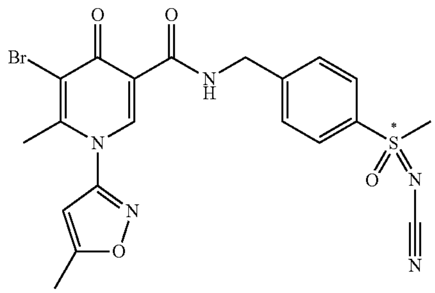 | 504 (Br pattern) | 0.76 min Z011_S03 |
| 10.4 | Prep. 8.6 | 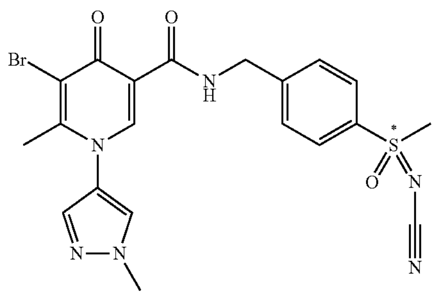 | 503 (Br pattern) | 0.75 min Z011_S03 |
| 10.5 | Prep. 8.7 | 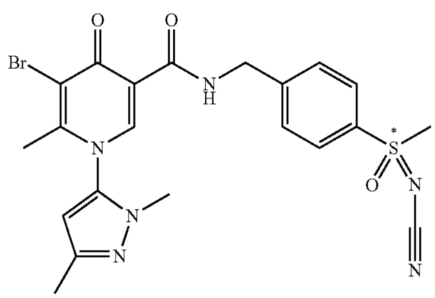 | 517 (Br pattern) | 0.74 min Z011_S03 |
| 10.6 | Prep. 8.8 | 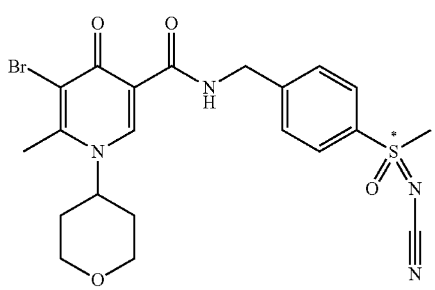 | 507 (Br pattern) | 0.68 min Z011_S03 |
| 10.7 | Prep. 8.9 | 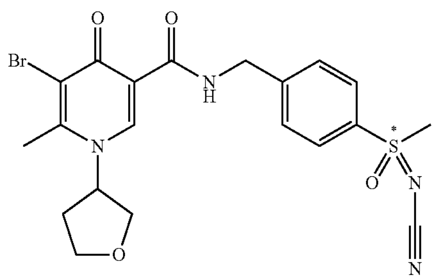 | 493 (Br pattern) | 0.67 min Z011_S03 |

-continued
| Prep-aration | Starting Material Acid | Structure | MS [M + H]+ | r.t. HPLC Method |
|---|---|---|---|---|
| 10.8 | Prep. 8.10 | 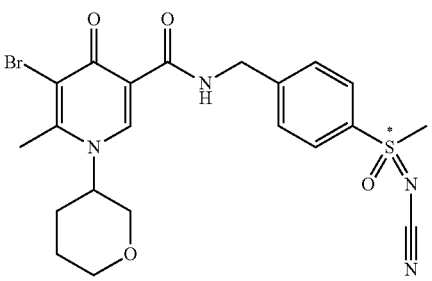 | 507 (Br pattern) | 0.70 min Z011_S03 |
| 10.9 | Prep. 8.11 | 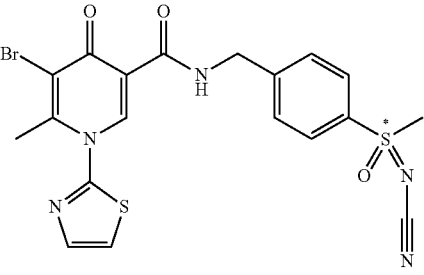 | 506 (Br pattern) | 0.73 min Z011_S03 |
| 10.10 | Prep. 8.15 | 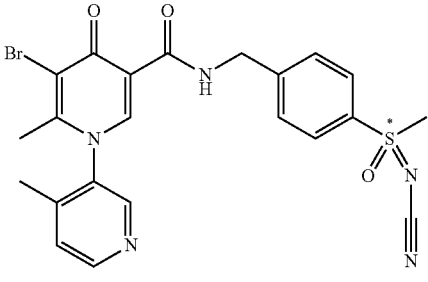 | 514 (Br pattern) | 0.70 min Z011_S03 |
| 10.11 | Prep. 8.16 | 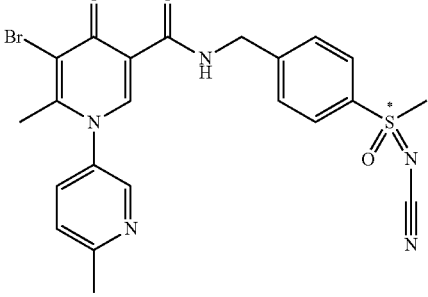 | 514 (Br pattern) | 0.71 min Z011_S03 |
| 10.12 | Prep 8.17 | 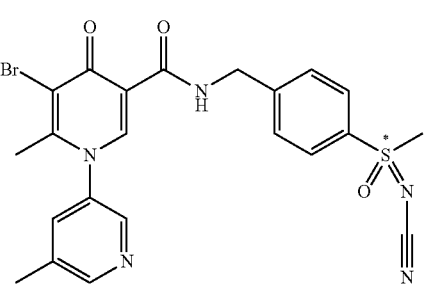 | 514 (Br pattern) | 0.72 min Z011_S03 |

Preparation 11A and Preparation 11B: Enantiomers of Preparation 6c

Racemic preparation 6c (2.0 g) is separated by chiral HPLC (Daicel Chiralcel OZ-H, 250 mm×30 mm, 32% MeOH in supercritical $CO_2$).

Early eluting enantiomer (preparation 11A): r.t. chiral HPLC=10.19 min (Daicel Chiralpak® IA 4.6 mm×250 mm×5 μm, 1 mL/min, 20 min, 70% hexane+15% isopropanol+15% dichloromethane+0.1% TFA, 20° C.); ESI mass spectrum: $[M+H]^+=334$; Yield: 600 mg.

Late eluting enantiomer (preparation 11B): r.t. chiral HPLC=10.70 min (Daicel Chiralpak® IA 4.6 mm×250 mm×5 μm, 1 mL/min, 20 min, 70% hexane+15% isopropanol+15% dichloromethane+0.1% TFA, 20° C.); ESI mass spectrum: $[M+H]^+=334$; Yield: 700 mg.

Preparation 12A: Early Eluting Enantiomer of Preparation 6d

The early eluting enantiomer of racemic preparation 6d is prepared following the procedure described for preparation 6d, substituting racemic 2-(4-(N-cyano-S-methyl-sulfonimidoyl)benzyl)isoindoline-1,3-dione with preparation 11A.

r.t. chiral HPLC=2.92 min (Daicel Chiralpak® IC 4.6 mm×250 mm 5 μm, 4 ml/min, 10 min, 30% MeOH+0.2% diethylamine in supercritical $CO_2$, 40° C., 100 bar back pressure); ESI mass spectrum: $[M+H]^+=210$.

Preparation 12B: Late Eluting Enantiomer of Preparation 6d

The late eluting enantiomer of racemic preparation 6d is prepared following the procedure described for preparation 6d, substituting racemic 2-(4-(N-cyano-S-methylsulfonimidoyl)-benzyl)isoindoline-1,3-dione with preparation 11B.

r.t. chiral HPLC=3.59 min (Daicel Chiralpak® IC 4.6 mm×250 mm 5 μm, 4 ml/min, 10 min, 30% MeOH+0.2% diethylamine in supercritical $CO_2$, 40° C., 100 bar back pressure); ESI mass spectrum: $[M+H]^+=210$.

Preparation 13: (4-(N-Cyano-S-ethylsulfonimidoyl) phenyl)methanamine

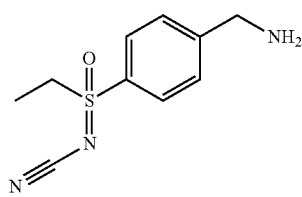

13a: 2-(4-(N-cyano-S-ethylsulfinimidoyl)benzyl) isoindoline-1,3-dione

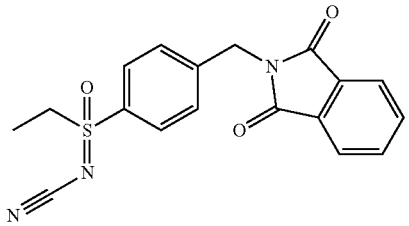 [SMILES: CCS(=O)(=NC#N)c1ccc(CN2C(=O)c3ccccc3C2=O)cc1]

Phthalic anhydride (4.42 g, 30 mmol) is added to a solution of 4-(ethylthio)benzylamine (5.00 g, 30 mmol) in acetic acid. The mixture is heated at reflux for 5 h and cooled at room temperature. Water ist added, and the precipitate is filtered and dried.

The residue is dissolved in methanol (50 mL), and the mixture is treated with potassium tert-butoxide (2.26 g, 20 mmol) and cyanamide (920 mg, 22 mmol). N-Bromosuccinimide (4.49 g, 25 mmol) is added, and the mixture is stirred at room temperature for 2 h. The mixture is concentrated under reduced pressure and treated with saturated aqueous $Na_2S_2O_3$ solution. The mixture is extracted four times with dichloromethane, and the combined organic layers are dried over $Na_2SO_4$ and concentrated under reduced pressure. The residue is purified by flash chromatography on silica (dichloromethane/methanol 95:5). Yield: 3.0 g (30% of theory); ESI mass spectrum: $[M+H]^+=338$; r.t. HPLC: 3.14 min (LCMS-FA-8).

13b: 2-(4-(N-cyano-S-ethylsulfonimidoyl)benzyl) isoindoline-1,3-dione

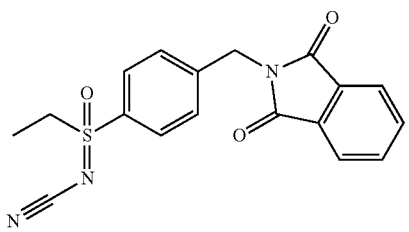 [SMILES: CCS(=O)(=NC#N)c1ccc(CN2C(=O)c3ccccc3C2=O)cc1]

The title compound is prepared in analogy to preparation 6c, substituting 2-(4-(N-cyano-S-methylsulfinimidoyl)benzyl)isoindoline-1,3-dione with 2-(4-(N-cyano-S-ethylsulfinimidoyl)benzyl)isoindoline-1,3-dione (preparation 13a). ESI mass spectrum: $[M+H]^+=354$; r.t. HPLC: 3.33 min (LCMS-FA-8).

13c: (4-(N-Cyano-S-ethylsulfonimidoyl)phenyl) methanamine

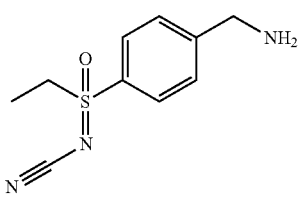

The title compound is prepared in analogy to preparation 6d, substituting 2-(4-(N-cyano-S-methylsulfonimidoyl)benzyl)isoindoline-1,3-dione with 2-(4-(N-cyano-S-ethylsulfonimidoyl)benzyl)isoindoline-1,3-dione (preparation 13b). ESI mass spectrum: [M+H]$^+$=224; r.t. HPLC: 0.52 min (Z011_S03).

Preparation 14: (4-(N-Cyano-S-isopropylsulfonimidoyl)phenyl)methanamine

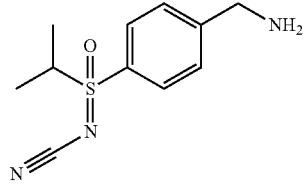

14a: 2-(4-(N-cyano-S-isopropylsulfinimidoyl)benzyl)isoindoline-1,3-dione

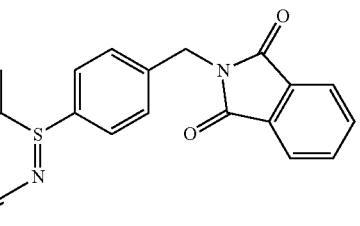

The title compound is prepared in analogy to preparation 13a, substituting 4-(ethylthio)-benzylamine with 4-(isopropylthio)benzylamine ESI mass spectrum: [M+H]$^+$=352; r.t. HPLC: 0.50 min (X012_S01).

14b: 2-(4-(N-cyano-S-isopropylsulfonimidoyl)benzyl)isoindoline-1,3-dione

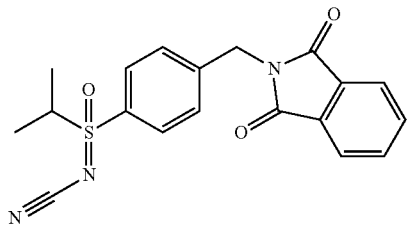 [SMILES: CC(C)S(=O)(=NC#N)c1ccc(CN2C(=O)c3ccccc3C2=O)cc1]

The title compound is prepared in analogy to preparation 6c, substituting 2-(4-(N-cyano-S-methylsulfinimidoyl)benzyl)isoindoline-1,3-dione with 2-(4-(N-cyano-S-isopropylsulfinimidoyl)benzyl)isoindoline-1,3-dione (preparation 14a). ESI mass spectrum: [M+H]$^+$=368; r.t. HPLC: 3.42 min (LCMS-FA-8).

14c: (4-(N-Cyano-S-isopropylsulfonimidoyl)phenyl)methanamine

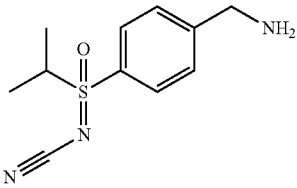

The title compound is prepared in analogy to preparation 6d, substituting 2-(4-(N-cyano-S-methylsulfonimidoyl)benzyl)isoindoline-1,3-dione with 2-(4-(N-cyano-S-isopropylsulfonimidoyl)benzyl)isoindoline-1,3-dione (preparation 14b). ESI mass spectrum: [M+H]$^+$=238; r.t. HPLC: 0.59 min (Z011_S03).

Preparation 15: 3-Fluoro-4-(N-cyano-S-methylsulfonimidoyl)benzylamine

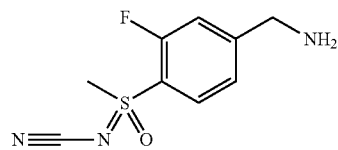

15a: 2-(3-Fluoro-4-methylsulfanyl-benzyl)-isoindole-1,3-dione

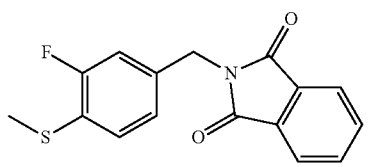 [SMILES: CSc1ccc(CN2C(=O)c3ccccc3C2=O)cc1F]

A mixture of 3-fluoro-4-methylsulfanyl-benzonitrile (6.00 g, 34.1 mmol), Raney-Nickel (100 mg) and concentrated aqueous ammonia (30 mL) in methanol (300 mL) is treated with hydrogen (3.4 bar) at room temperature for 3 h. The mixture is filtered through a pad of silica gel, and the filtrate is concentrated under reduced pressure.

The residue is dissolved in toluene (250 mL), treated with phthalic anhydride (4.0 g, 26.3 mmol) and triethylamine (0.98 g, 9.50 mmol), and the mixture is heated at reflux over night. All volatiles are removed, and the residue is recrystallized from ethanol. Yield: 4.8 g (46% of theory). ESI mass spectrum: [M+H]⁺=302; r.t. HPLC: 0.67 min (X012_S01).

15b: 2-(3-Fluoro-4-(N-cyano-S-methylsulfinimidoyl)-benzyl)-isoindole-1,3-dione

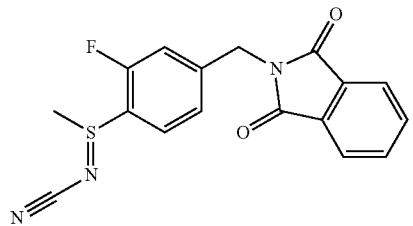 [SMILES: C/S(=N\C#N)c1ccc(CN2C(=O)c3ccccc3C2=O)cc1F]

Cyanamide (350 mg, 8.20 mmol) and potassium tert-butoxide (860 mg, 7.60 mmol) are added to a solution of 2-(3-fluoro-4-methylsulfanyl-benzyl)-isoindole-1,3-dione (preparation 15a, 2.00 g, 6.31 mmol) in methanol (50 mL). N-Bromosuccinimide (1.70 g, 9.50 mmol) is added and the mixture is stirred at room temperature over night. All volatiles are removed under reduced pressure, and the residue is treated with dichloromethane (20 mL). The mixture is washed with saturated aqueous sodium chloride solution, dried over Na₂SO₄ and concentrated under reduced pressure. The residue is directly used in the next step without further purification. Yield: 1.61 g (60% of theory); ESI mass spectrum: [M+H]⁺=342; r.t. HPLC: 0.76 min (5-95AB).

15c: 2-(3-Fluoro-4-(N-cyano-S-methylsulfonimidoyl)-benzyl)-isoindole-1,3-dione

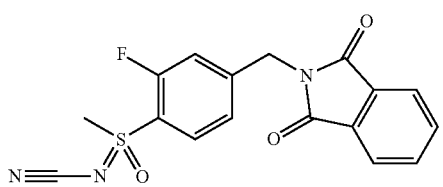 [SMILES: CS(=O)(=NC#N)c1ccc(CN2C(=O)c3ccccc3C2=O)cc1F]

2-(3-Fluoro-4-(N-cyano-S-methylsulfinimidoyl)-benzyl)-isoindole-1,3-dione (preparation 15b, 1.60 g, 4.22 mmol) and acetic acid (0.25 g, 4.22 mmol) are added to a solution of potassium permanganate (670 mg, 4.22 mmol) in a mixture of water (8 mL) and acetonitrile (9.6 ml). The mixture is stirred over night, and saturated aqueous Na₂S₂O₃ solution is added. The mixture is extracted with ethyl acetate and the organic layer is dried over Na₂SO₄. The residue is directly used in the next step without further purification. Yield: 1.34 g (80% of theory); ESI mass spectrum: [M+H]⁺=358; r.t. HPLC: 0.73 min (5-95AB).

15d: 3-Fluoro-4-(N-cyano-S-methylsulfonimidoyl) benzylamine

Hydrazine (85% in water, 2.0 g, 53 mmol) is added to a solution of 2-(3-fluoro-4-(N-cyano-S-methylsulfonimidoyl)-benzyl)-isoindole-1,3-dione (preparation 15c, 3.5 g, 8.8 mmol) in a 1:1 mixture of dichloromethane and methanol (140 mL). The mixture is stirred over night and concentrated under reduced pressure. The residue is purified by preparative reversed phase HPLC (Luna C18(2), gradient of acetonitrile in water, 0.01 M NH₃). Yield: 1.2 g (58% of theory); ESI mass spectrum: [M+H]⁺=228; r.t. HPLC: 0.26 min (X011_S03).

Preparation 16: (5-(N-Cyano-S-methylsulfonimidoyl)pyridin-2-yl)methanamine

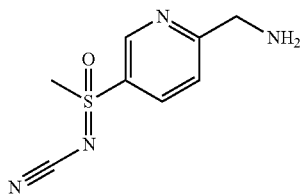

16a: 5-(Methylthio)pyridin-2-yl)methylamine

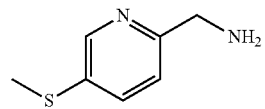

A solution of 5-methylsulfanyl-pyridine-2-carbonitrile (preparation described in WO05026124, 4.28 g, 28.5 mmol) in THF is cooled at −78° C. in a dry ice/ethanol bath. Lithium aluminium hydride (2.4 M in THF, 12 mL, 28.8 mmol) is added dropwise. After 10 min water (1 mL) and THF (3 mL) are added. After 5 min, aqueous sodium hydroxide solution (4 M, 1 mL) and water (3 mL) is added. After 10 min the mixture is concentrated under reduced pressure, and the residue is dissolved in a mixture of water, methanol and acetic acid and purified by preparative reversed phase HPLC (Sunfire, gradient of acetonitrile in water, 0.1% formic acid). Yield: 1.36 g (31% of theory); ESI mass spectrum: [M+H]⁺=155; r.t. HPLC: 0.44 min (Z018_S04).

16b: 2-(5-Methylsulfanyl-pyridin-2-ylmethyl)-isoindole-1,3-dione

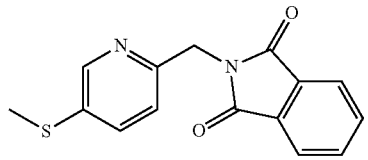 [SMILES: CSc1ccc(CN2C(=O)c3ccccc3C2=O)nc1]

The title compound is prepared in analogy to preparation 6a, substituting 4-(methylthio)-benzylamine with (5-methylsulfanyl-pyridin-2-yl)-methylamine (preparation 16a). ESI mass spectrum: [M+H]⁺=285; r.t. HPLC: 0.51 min (X012_S01).

16c: 2-(5-(N-Cyano-S-methylsulfinimidoyl)pyridin-2-yl)-isoindole-1,3-dione

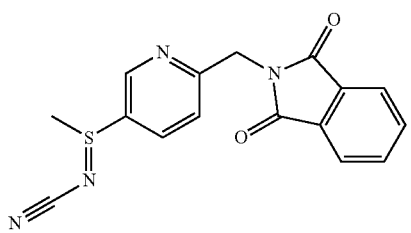 [SMILES: C/S(=N\C#N)c1ccc(CN2C(=O)c3ccccc3C2=O)nc1]

The title compound is prepared in analogy to preparation 6b, substituting 2-(4-(methylthio)benzyl)isoindoline-1,3-dione with 2-(5-methylsulfanyl-pyridin-2-ylmethyl)-isoindole-1,3-dione (preparation 16b). ESI mass spectrum: [M+H]⁺=325; r.t. HPLC: 0.63 min (Z018_S04).

16d: 2-(5-(N-Cyano-S-methylsulfonimidoyl)pyridin-2-yl)-isoindole-1,3-dione

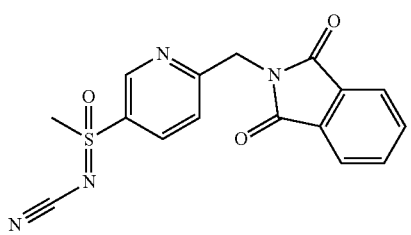 [SMILES: CS(=O)(=NC#N)c1ccc(CN2C(=O)c3ccccc3C2=O)nc1]

The title compound is prepared in analogy to preparation 6c, substituting 2-(4-(N-cyano-S-methylsulfinimidoyl)benzyl)isoindoline-1,3-dione with 2-(5-(N-cyano-S-methylsulfinimidoyl)pyridin-2-yl)-isoindole-1,3-dione (preparation 16c). ESI mass spectrum: [M+H]⁺=341; r.t. HPLC: 0.88 min (Z018_S04).

16e: (5-(N-Cyano-S-methylsulfonimidoyl)pyridin-2-yl)methanamine

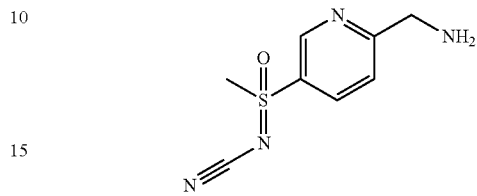

The title compound is prepared in analogy to preparation 6d, substituting 2-(4-(N-cyano-S-methylsulfonimidoyl)benzyl)isoindoline-1,3-dione with 2-(5-(N-cyano-S-methylsulfonimidoyl)pyridin-2-yl)-isoindole-1,3-dione (preparation 16d). ESI mass spectrum: [M+H]⁺=211; r.t. HPLC: 0.23 min (Z011_S03).

Preparation 17:
(4-(S-Methyl-N-(methylsulfonyl))phenyl)methanamine

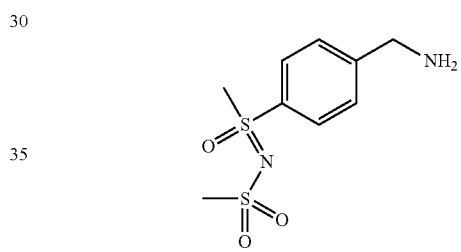

17a: 2-(4-(N-Trifluoracetyl-S-methylsulfonimidoyl)benzyl)isoindoline-1,3-dione

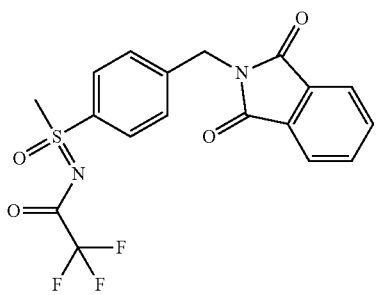 [SMILES: CS(=O)(=NC(=O)C(F)(F)F)c1ccc(CN2C(=O)c3ccccc3C2=O)cc1]

A solution of 2-(4-(N-cyano-S-methylsulfonimidoyl)benzyl)isoindoline-1,3-dione (preparation 6c, 2.00 g, 6.00 mmol) in dichloromethane (20 mL) is cooled at 0° C., and trifluoroacetic anhydride (2.48 mL, 3.72 g, 17.7 mmol) is added. The mixture is allowed to warm to room temperature, stirred for 2 h and poured into water. The aqueous layer is extracted three times with dichloromethane, and the combined organic layers are dried over Na₂SO₄ and concentrated under reduced pressure. The residue is purified by flash chromatography on silica (ethyl acetate/dichloromethane 9:1). Yield: 2.10 g (86% of theory); ESI mass spectrum: [M+H]$^+$=411, r.t. HPLC: 4.50 min (LCMS-FA-2).

17b: 2-(4-(S-Methylsulfonimidoyl)benzyl)isoindoline-1,3-dione

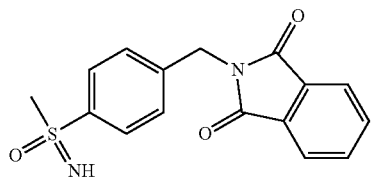 [SMILES: CS(=N)(=O)c1ccc(CN2C(=O)c3ccccc3C2=O)cc1]

Potassium carbonate (3.37 g, 24.4 mmol) is added to a solution of 2-(4-(N-trifluoracetyl-S-methylsulfonimidoyl)benzyl)isoindoline-1,3-dione (preparation 17a, 2.00 g, 4.88 mmol) in methanol (20 mL). The mixture is stirred at room temperature for 16 h and filtered. The filtrate is concentrated under reduced pressure, and the residue is purified by flash chromatography on silica (methanol/dichloromethane 7:3). Yield: 0.90 g (58% of theory); ESI mass spectrum: [M+H]$^+$=315, r.t. HPLC: 1.08 min (V003_003).

17c: 2-(4-(S-Methyl-N-(methylsulfonyl)sulfonimidoyl)benzyl)isoindoline-1,3-dione

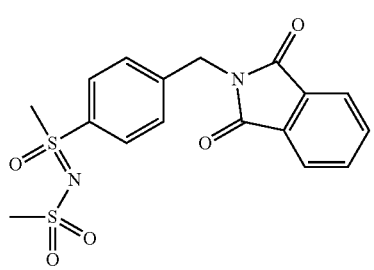 [SMILES: CS(=O)(=O)N=S(C)(=O)c1ccc(CN2C(=O)c3ccccc3C2=O)cc1]

A solution of 2-(4-(S-methylsulfonimidoyl)benzyl)isoindoline-1,3-dione (preparation 17b, 2.50 g, 7.95 mmol) and triethylamine (2.2 mL, 16 mmol) in dichloromethane (20 mL) is cooled at 0° C. and treated with methanesulfonyl chloride (620 µL, 8.0 mmol). The mixture is stirred at this temperature for 1.5 h and then washed with water. The organic layer is concentrated under reduced pressure, and the residue is suspended in a mixture of methanol and water. The precipitate is filtered, washed with water, and dried. Yield: 273 mg (8% of theory); ESI mass spectrum: [M+H]$^+$=393, r.t. HPLC: 0.44 min (X012_S01).

17d: (4-(S-Methyl-N-(methylsulfonyl))phenyl)methanamine

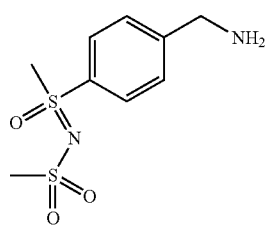 [SMILES: CS(=O)(=O)N=S(C)(=O)c1ccc(CN)cc1]

A solution of 2-(4-(S-methyl-N-(methylsulfonyl)sulfonimidoyl)benzyl)isoindoline-1,3-dione (preparation 17c, 270 mg, 0.69 mmol) and 1,2-diaminoethane (83 µL, 74 mg, 1.24 mmol) in a 2:1:1 mixture of acetonitrile, tetrahydrofuran and ethanol (3 mL) is heated at 60° C. for 4 h. The mixture is concentrated under reduced pressure, and the residue is suspended in dichloromethane. The mixture is filtered and the filtrate is concentrated under reduced pressure. Yield: 178 mg (99% of theory); ESI mass spectrum: [M+H]$^+$=263, r.t. HPLC: 0.17 min (X012_S01).

Preparation 18: 2-Fluoro-4-(N-cyano-S-methylsulfonimidoyl)benzylamine

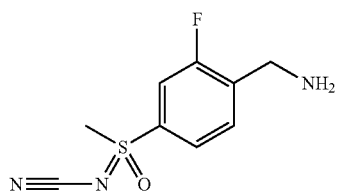

18a: 2-Fluoro-4-methylsulfanyl-benzylamine

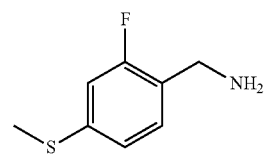

A mixture of 2-fluoro-4-methylsulfanyl-benzonitrile (8.0 g, 45.5 mmol), Raney-Nickel (20.0 g) and concentrated aqueous ammonia (300 mL) in methanol (3.0 L) is treated with hydrogen (3.4 bar) at room temperature and stirred overnight. The mixture is filtered through a pad of silica gel, and the filtrate is concentrated under reduced pressure. Yield: 6.3 g (81% of theory); ESI mass spectrum: [M+H–NH$_3$]$^+$=155; r.t. HPLC: 1.38 min (0-30AB).

18b: (2-Fluoro-4-methylsulfanyl-benzyl)-carbamic acid tert-butyl ester

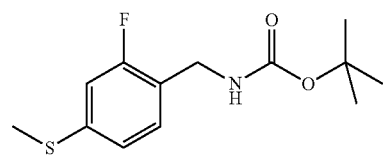 [SMILES: CSc1ccc(CNC(=O)OC(C)(C)C)c(F)c1]

Triethylamine (3.40 g, 33.3 mmol) and di-tert-butyl dicarbonate (7.4 g, 33.3 mmol) are added to a solution of 2-fluoro-4-methylsulfanyl-benzylamine (preparation 18a, 4.0 g, 22.2 mmol) in dichloromethane (100 mL). After 30 min water is added and the mixture is extracted with dichloromethane. The organic layer is washed with brine, dried over Na$_2$SO$_4$ and concentrated under reduced pressure. Yield: 5.0 g (79% of theory); ESI mass spectrum: [M+Na]$^+$=294; r.t. HPLC: 0.86 min (5-95AB).

18c: (2-Fluoro-4-(N-cyano-S-methylsulfinimidoyl)-benzyl)-carbamic acid tert-butyl ester

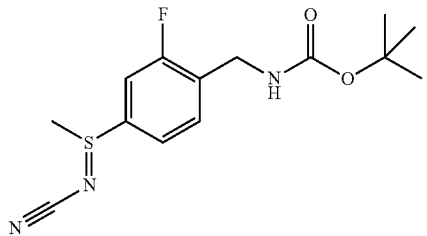 [SMILES: C/S(=N\C#N)c1ccc(CNC(=O)OC(C)(C)C)c(F)c1]

The title compound is prepared following the procedure described for preparation 15b, using (2-fluoro-4-methylsulfanyl-benzyl)-carbamic acid tert-butyl ester (preparation 18b) as starting material. ESI mass spectrum: [M+H]$^+$=312; r.t. HPLC: 0.68 min (5-95AB).

18d: (2-Fluoro-4-(N-cyano-S-methylsulfonimidoyl)-benzyl)-carbamic acid tert-butyl ester

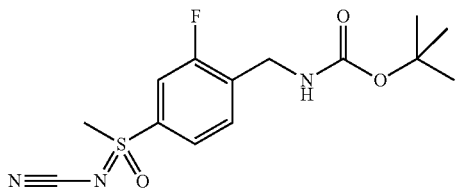 [SMILES: CC(C)(C)OC(=O)NCc1ccc(S(C)(=O)=NC#N)cc1F]

The title compound is prepared following the procedure described for preparation 15c, using (2-fluoro-4-(N-cyano-S-methylsulfinimidoyl)-benzyl)-carbamic acid tert-butyl ester (preparation 18c) as starting material. ESI mass spectrum: [M+H]$^+$=312; r.t. HPLC: 0.68 min (5-95AB).

18e: 2-Fluoro-4-(N-cyano-S-methylsulfonimidoyl)benzylamine

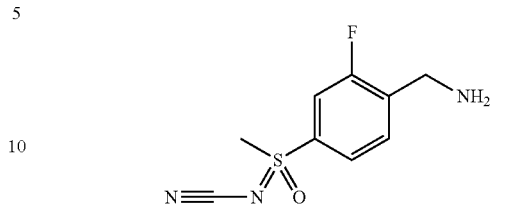

A solution of (2-fluoro-4-(N-cyano-S-methylsulfonimidoyl)-benzyl)-carbamic acid tert-butyl ester (preparation 18c, 2.20 g, 6.38 mmol) in dichloromethane (20 mL) is cooled at 0° C. and treated with a solution of hydrogen chloride in ethyl acetate (4 M, 16 mL, 64 mmol). After 2 h all volatiles are removed under reduced pressure and the residue is purifed by preparative reversed phase HPLC (Gemini, gradient of acetonitrile in water, 0.04% NH$_3$). ESI mass spectrum: [M+H]$^+$=228; r.t. HPLC: 2.16 min (0-30AB).

Preparation 19: 2-Methyl-4-(N-cyano-S-methylsulfonimidoyl)benzylamine

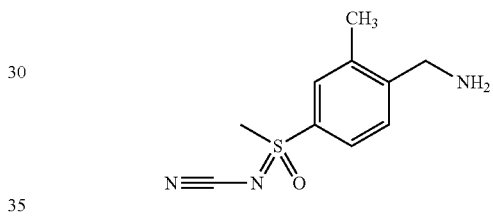

The title compound is prepared following the procedure described for preparation 15, substituting 3-fluoro-4-methylsulfanyl-benzonitrile with 2-methyl-4-methylsulfanyl-benzonitrile as starting material. ESI mass spectrum: [M+H]$^+$= 224; r.t. HPLC: 2.18 min (0-30AB).

The following examples are prepared as described for preparation 1d, substituting preparation 1c with the appropriate starting material acid and substituting preparation 6 with the appropriate starting material amine. The asterisk in the structures indicates that the compound is prepared from the enantiomer preparation 12B (prep.=preparation).

| Example | Starting Material Acid | Starting Material Amine | Structure | MS [M + H]$^+$ | r.t. HPLC Method |
|---|---|---|---|---|---|
| 10 | Prep. 9.1 | Prep.13 | 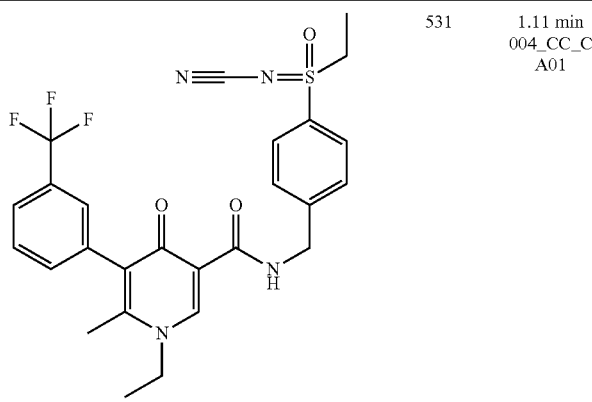 | 531 | 1.11 min 004_CC_C A01 |

-continued
| Example | Starting Material Acid | Starting Material Amine | Structure | MS [M + H]+ | r.t. HPLC Method |
|---|---|---|---|---|---|
| 11 | Prep. 9.1 | Prep. 14 | 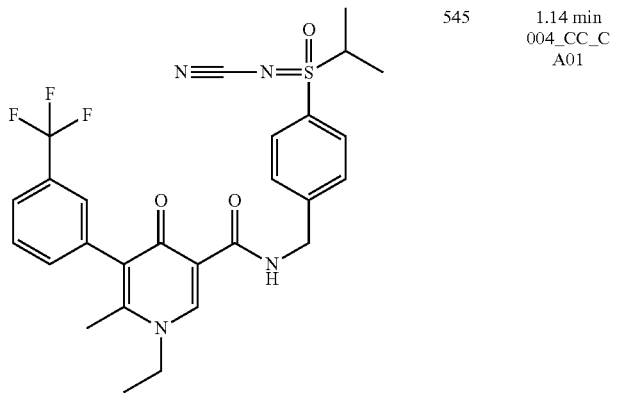 | 545 | 1.14 min 004_CC_CA01 |
| 12 | Prep. 9.2 | Prep. 13 | 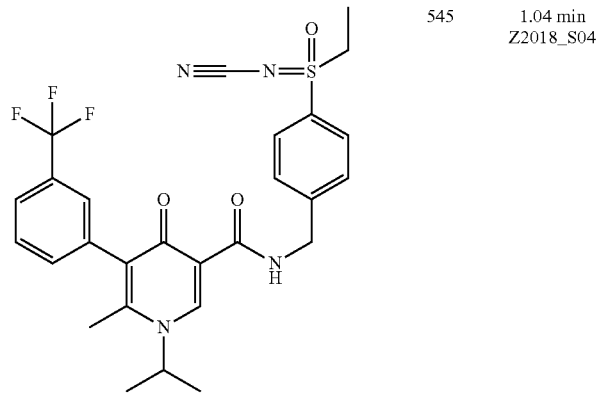 | 545 | 1.04 min Z2018_S04 |
| 13 | Prep. 9.2 | Prep. 15 | 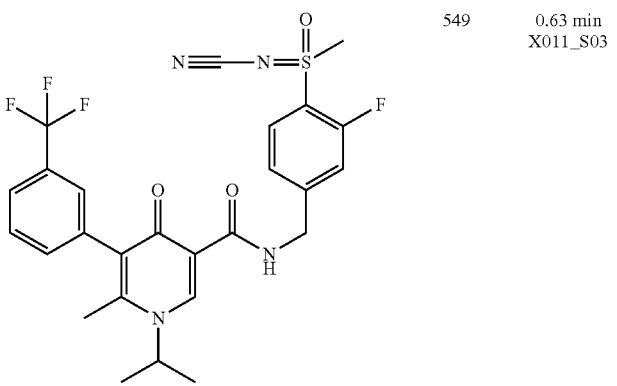 | 549 | 0.63 min X011_S03 |

| Example | Starting Material Acid | Starting Material Amine | Structure | MS [M + H]+ | r.t. HPLC Method |
|---|---|---|---|---|---|
| 14 | Prep. 9.2 | Prep. 18 | 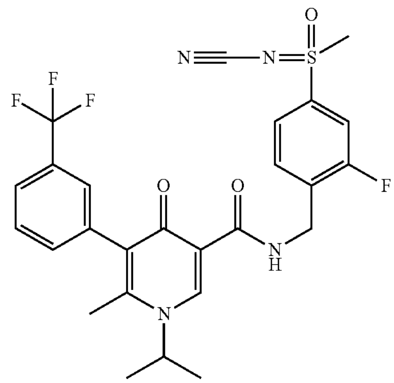 [SMILES: Cc1c(-c2cccc(C(F)(F)F)c2)c(=O)c(C(=O)NCc2ccc(S(C)(=O)=NC#N)cc2F)cn1C(C)C] | 549 | 0.62 min X011_S03 |
| 15 | Prep. 9.2 | Prep. 19 | 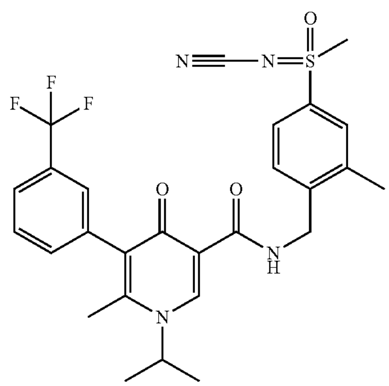 [SMILES: Cc1cc(S(C)(=O)=NC#N)ccc1CNC(=O)c1cn(C(C)C)c(C)c(-c2cccc(C(F)(F)F)c2)c1=O] | 545 | 0.62 min X011_S03 |
| 16 | Prep. 9.2 | Prep. 16 | 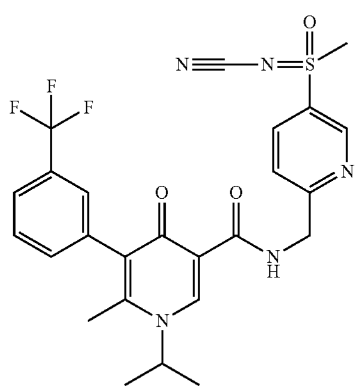 [SMILES: Cc1c(-c2cccc(C(F)(F)F)c2)c(=O)c(C(=O)NCc2ccc(S(C)(=O)=NC#N)cn2)cn1C(C)C] | 532 | 0.77 min 003_CA04 |
| 17 | Prep. 9.2 | Prep. 17 | 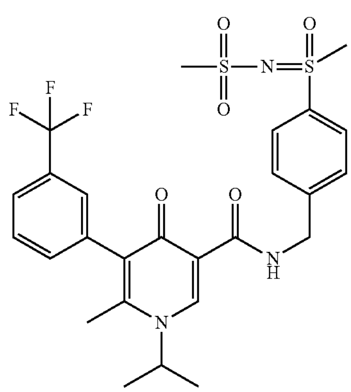 [SMILES: Cc1c(-c2cccc(C(F)(F)F)c2)c(=O)c(C(=O)NCc2ccc(S(C)(=O)=NS(C)(=O)=O)cc2)cn1C(C)C] | 584 | 1.06 min V011_S01 |

-continued
| Example | Starting Material Acid | Starting Material Amine | Structure | MS [M + H]⁺ | r.t. HPLC Method |
|---|---|---|---|---|---|
| 18 | Prep. 9.3 | Prep. 13 | 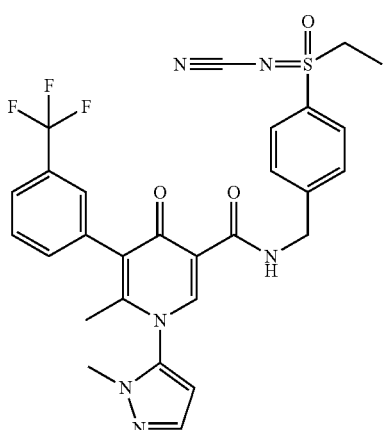 | 583 | 1.01 min Z017_S04 |
| 19 | Prep. 9.3 | Prep. 14 | 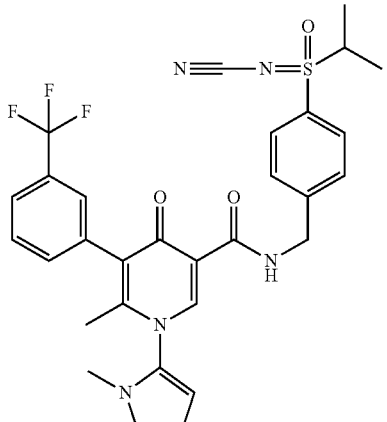 | 597 | 1.39 min 001_CA03 |
| 20 | Prep. 9.4 | Prep. 12B | 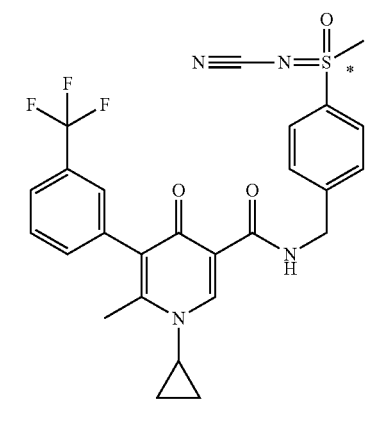 [SMILES: Cc1c(-c2cccc(C(F)(F)F)c2)c(=O)c(C(=O)NCc2ccc(S(C)(=O)=NC#N)cc2)cn1C1CC1] | 529 | 0.61 min X011_S03 |

-continued
| Example | Starting Material Acid | Starting Material Amine | Structure | MS [M + H]+ | r.t. HPLC Method |
|---|---|---|---|---|---|
| 21 | Prep. 9.4 | Prep. 13 | 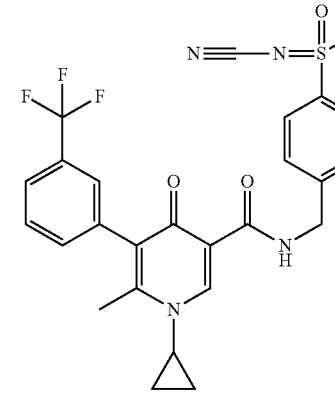 | 543 | 0.63 min X011_S03 |
| 22 | Prep. 9.4 | Prep. 14 | 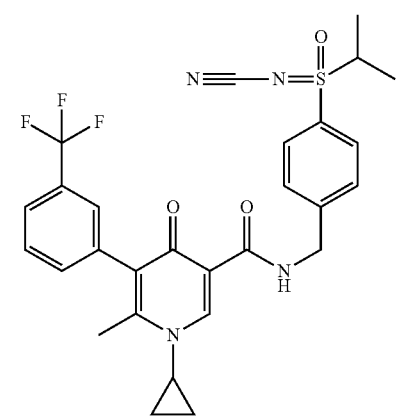 [SMILES: Cc1c(-c2cccc(C(F)(F)F)c2)c(=O)c(C(=O)NCc2ccc(S(=O)(=NC#N)C(C)C)cc2)cn1C1CC1] | 557 | 0.65 min X011_S03 |
| 23 | Prep. 9.5 | Prep. 12B | 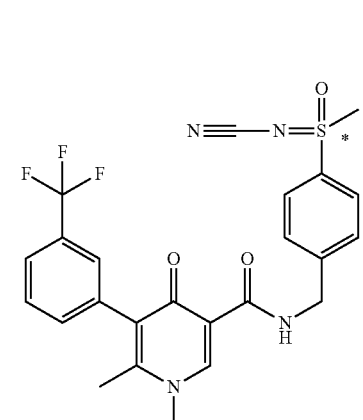 | 584 | 0.91 min Z018_S04 |

-continued

| Example | Starting Material Acid | Starting Material Amine | Structure | MS [M + H]+ | r.t. HPLC Method |
|---|---|---|---|---|---|
| 24 | Prep. 9.6 | Prep. 12B | 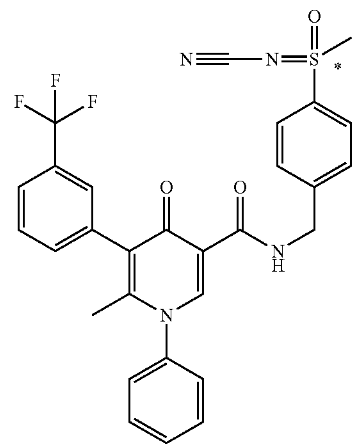 [SMILES: Cc1c(-c2cccc(C(F)(F)F)c2)c(=O)c(C(=O)NCc2ccc(S(C)(=O)=NC#N)cc2)cn1-c1ccccc1] | 565 | 0.94 min Z011_S03 |
| 25 | Prep. 9.7 | Prep. 12B | 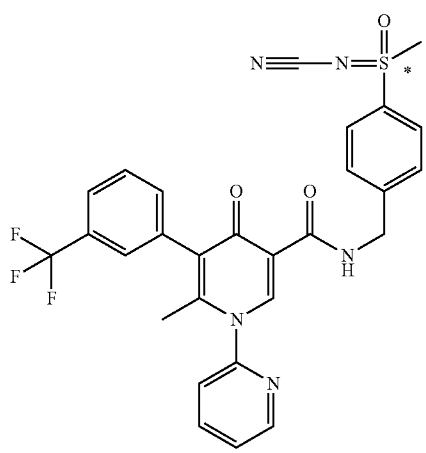 [SMILES: Cc1c(-c2cccc(C(F)(F)F)c2)c(=O)c(C(=O)NCc2ccc(S(C)(=O)=NC#N)cc2)cn1-c1ccccn1] | 566 | 0.94 min Z011_S03 |
| 26 | Prep. 9.8 | Prep. 12B | 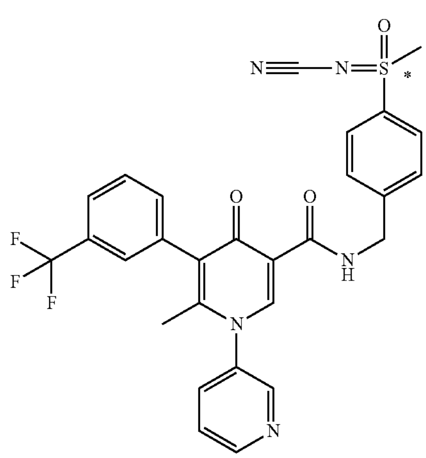 [SMILES: Cc1c(-c2cccc(C(F)(F)F)c2)c(=O)c(C(=O)NCc2ccc(S(C)(=O)=NC#N)cc2)cn1-c1cccnc1] | 566 | 0.84 min Z011_S03 |

-continued

| Example | Starting Material Acid | Starting Material Amine | Structure | MS [M + H]+ | r.t. HPLC Method |
|---|---|---|---|---|---|
| 27 | Prep. 9.9 | Prep. 12B | 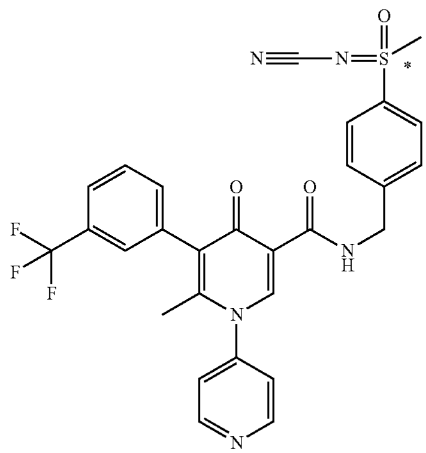 [SMILES: Cc1c(-c2cccc(C(F)(F)F)c2)c(=O)c(C(=O)NCc2ccc(S(C)(=O)=NC#N)cc2)cn1-c1ccncc1] | 566 | 0.83 min Z011_S03 |
| 28 | Prep. 9.10 | Prep. 12B | 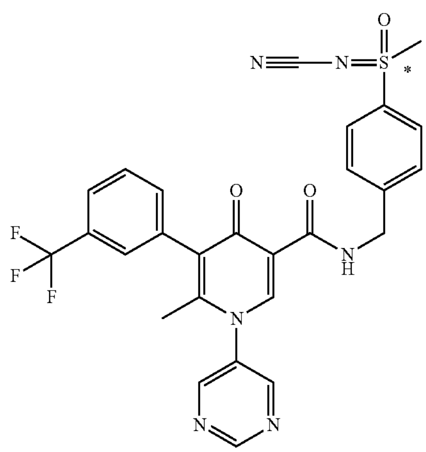 [SMILES: Cc1c(-c2cccc(C(F)(F)F)c2)c(=O)c(C(=O)NCc2ccc(S(C)(=O)=NC#N)cc2)cn1-c1cncnc1] | 567 | 0.81 min Z011_S03 |
| 29 | Prep. 9.11 | Prep. 13 | 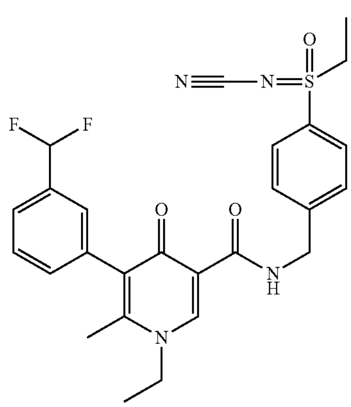 [SMILES: CCn1cc(C(=O)NCc2ccc(S(=O)(CC)=NC#N)cc2)c(=O)c(-c2cccc(C(F)F)c2)c1C] | 513 | 1.03 min 004_CC_CA01 |

-continued

| Example | Starting Material Acid | Starting Material Amine | Structure | MS [M + H]+ | r.t. HPLC Method |
|---|---|---|---|---|---|
| 30 | Prep. 9.11 | Prep. 14 | 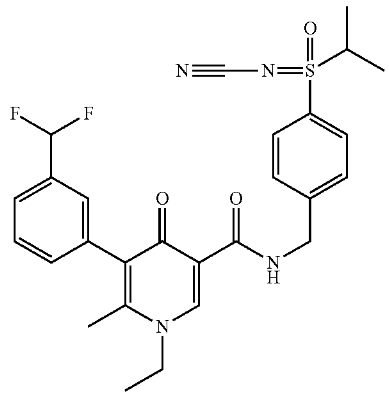 [SMILES: CCn1cc(C(=O)NCc2ccc(S(=O)(=NC#N)C(C)C)cc2)c(=O)c(-c2cccc(C(F)F)c2)c1C] | 527 | 1.07 min 004_CC_CA01 |
| 31 | Prep. 9.12 | Prep. 13 | 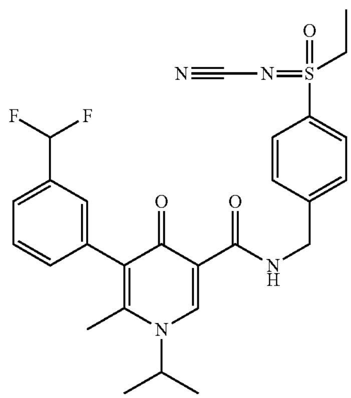 [SMILES: CCS(=O)(=NC#N)c1ccc(CNC(=O)c2cn(C(C)C)c(C)c(-c3cccc(C(F)F)c3)c2=O)cc1] | 527 | 1.00 min Z018_S04 |
| 32 | Prep. 9.12 | Prep. 15 | 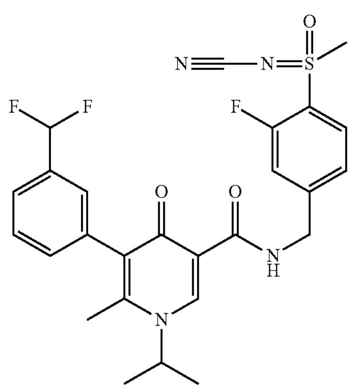 [SMILES: Cc1c(-c2cccc(C(F)F)c2)c(=O)c(C(=O)NCc2ccc(S(C)(=O)=NC#N)c(F)c2)cn1C(C)C] | 531 | 0.57 min X011_S03 |
| 33 | Prep. 9.12 | Prep. 18 | 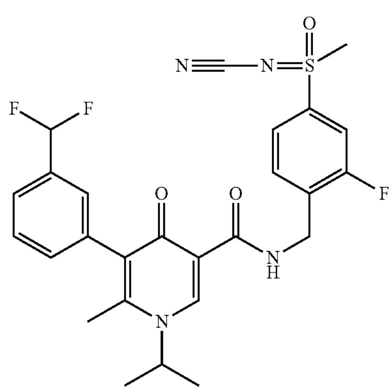 [SMILES: Cc1c(-c2cccc(C(F)F)c2)c(=O)c(C(=O)NCc2ccc(S(C)(=O)=NC#N)cc2F)cn1C(C)C] | 531 | 0.56 min X011_S03 |

-continued
| Example | Starting Material Acid | Starting Material Amine | Structure | MS [M + H]⁺ | r.t. HPLC Method |
|---|---|---|---|---|---|
| 34 | Prep. 9.12 | Prep. 19 | 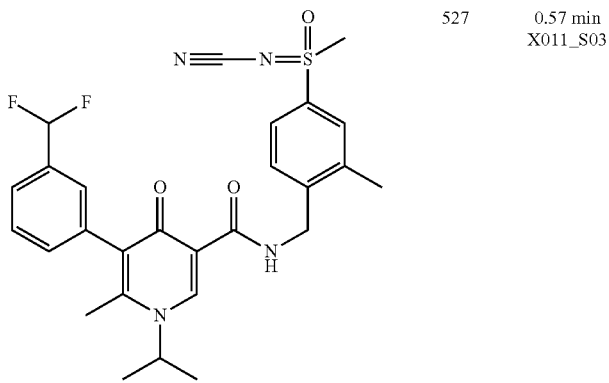 | 527 | 0.57 min X011_S03 |
| 35 | Prep. 9.12 | Prep. 17 | 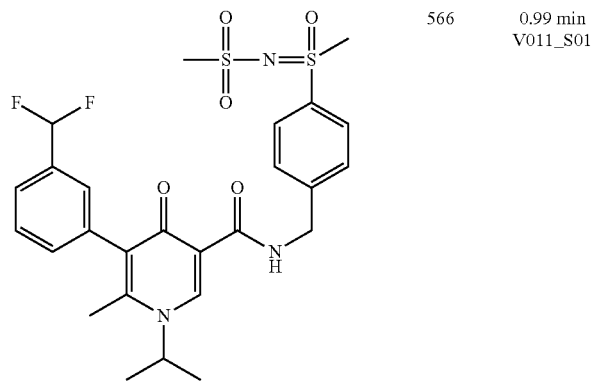 | 566 | 0.99 min V011_S01 |
| 36 | Prep. 9.13 | Prep. 13 | 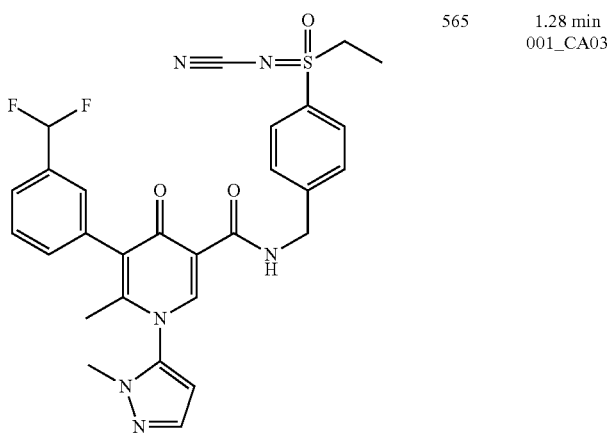 | 565 | 1.28 min 001_CA03 |

-continued

| Example | Starting Material Acid | Starting Material Amine | Structure | MS [M + H]⁺ | r.t. HPLC Method |
|---|---|---|---|---|---|
| 37 | Prep. 9.13 | Prep. 14 | 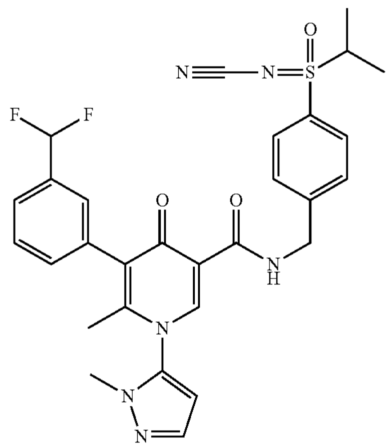 [SMILES: Cc1c(-c2cccc(C(F)F)c2)c(=O)c(C(=O)NCc2ccc(S(=O)(=NC#N)C(C)C)cc2)cn1-c1ccnn1C] | 579 | 1.31 min 001_CA03 |
| 38 | Prep. 9.14 | Prep. 12B | 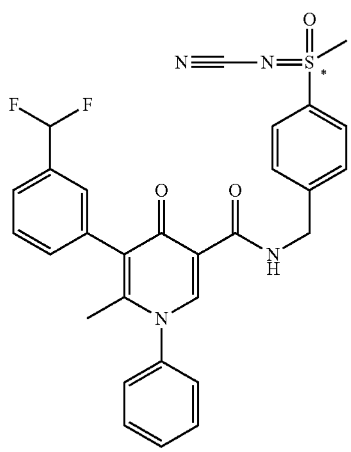 [SMILES: Cc1c(-c2cccc(C(F)F)c2)c(=O)c(C(=O)NCc2ccc(S(C)(=O)=NC#N)cc2)cn1-c1ccccc1] | 547 | 0.88 min Z011_S03 |
| 39 | Prep. 9.15 | Prep. 12B | 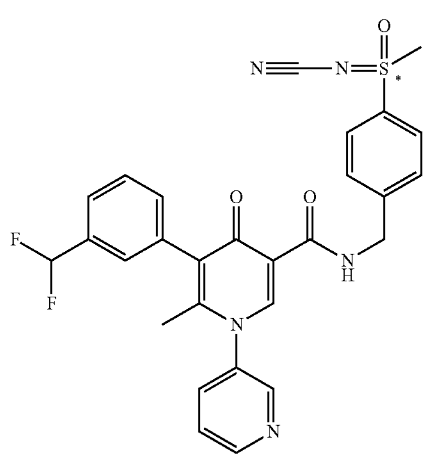 [SMILES: Cc1c(-c2cccc(C(F)F)c2)c(=O)c(C(=O)NCc2ccc(S(C)(=O)=NC#N)cc2)cn1-c1cccnc1] | 548 | 0.78 min Z011_S03 |

-continued
| Example | Starting Material Acid | Starting Material Amine | Structure | MS [M + H]+ | r.t. HPLC Method |
|---|---|---|---|---|---|
| 40 | Prep. 9.16 | Prep. 12B | 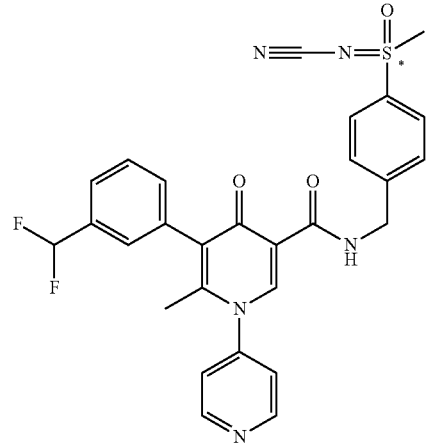 [SMILES: Cc1c(-c2cccc(C(F)F)c2)c(=O)c(C(=O)NCc2ccc(S(C)(=O)=NC#N)cc2)cn1-c1ccncc1] | 548 | 0.75 min Z011_S03 |
| 41 | Prep. 9.17 | Prep. 12B | 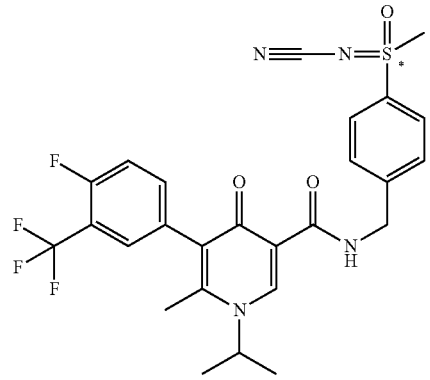 [SMILES: Cc1c(-c2ccc(F)c(C(F)(F)F)c2)c(=O)c(C(=O)NCc2ccc(S(C)(=O)=NC#N)cc2)cn1C(C)C] | 549 | 0.88 min Z011_S03 |
| 42 | Prep. 9.18 | Prep. 12B | 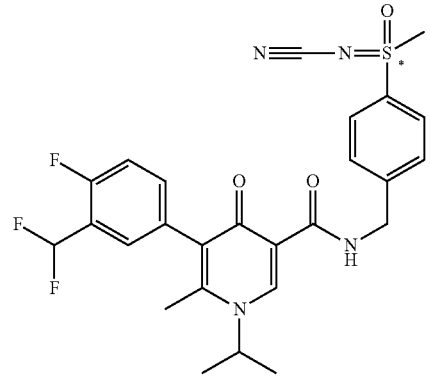 [SMILES: Cc1c(-c2ccc(F)c(C(F)F)c2)c(=O)c(C(=O)NCc2ccc(S(C)(=O)=NC#N)cc2)cn1C(C)C] | 531 | 0.83 min Z011_S03 |

-continued

| Example | Starting Material Acid | Starting Material Amine | Structure | MS [M + H]+ | r.t. HPLC Method |
|---|---|---|---|---|---|
| 43 | Prep. 9.19 | Prep. 12B | 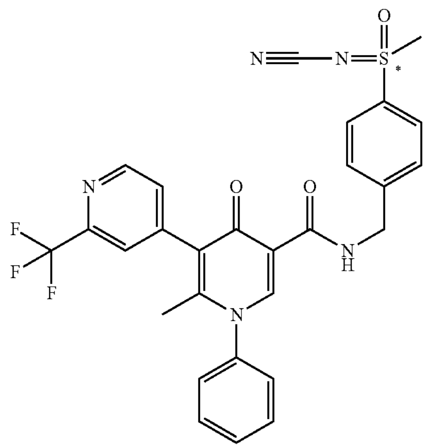 [SMILES: Cc1c(-c2ccnc(C(F)(F)F)c2)c(=O)c(C(=O)NCc2ccc(S(C)(=O)=NC#N)cc2)cn1-c1ccccc1] | 566 | 0.85 min Z011_S03 |
| 44 | Prep. 9.20 | Prep. 12B | 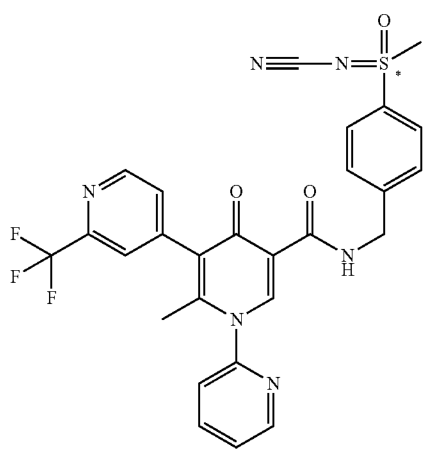 [SMILES: Cc1c(-c2ccnc(C(F)(F)F)c2)c(=O)c(C(=O)NCc2ccc(S(C)(=O)=NC#N)cc2)cn1-c1ccccn1] | 567 | 0.79 min Z011_S03 |
| 45 | Prep. 9.21 | Prep. 12B | 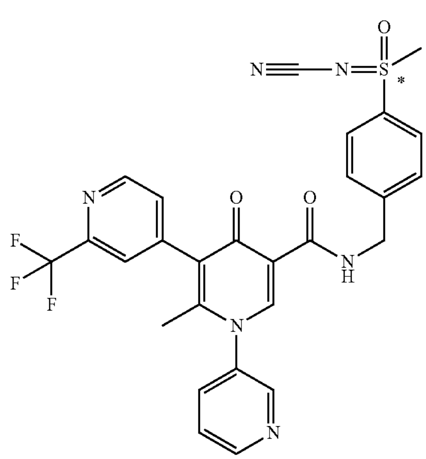 [SMILES: Cc1c(-c2ccnc(C(F)(F)F)c2)c(=O)c(C(=O)NCc2ccc(S(C)(=O)=NC#N)cc2)cn1-c1cccnc1] | 567 | 0.75 min Z011_S03 |

-continued

| Example | Starting Material Acid | Starting Material Amine | Structure | MS [M + H]+ | r.t. HPLC Method |
|---|---|---|---|---|---|
| 46 | Prep. 9.22 | Prep. 12B | 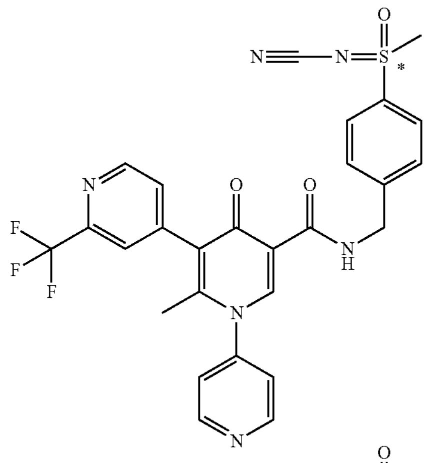 | 567 | 0.75 min Z011_S03 |
| 47 | Prep. 9.2 | Prep. 12B | 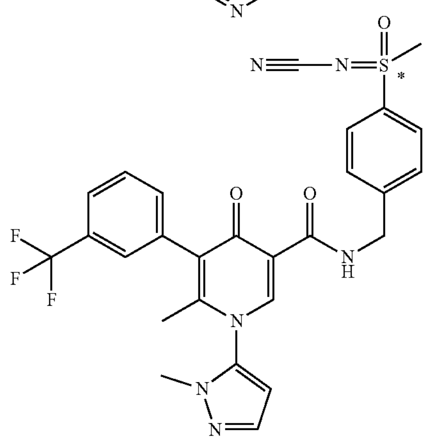 | 569 | 0.86 min Z011_S03 |

The following examples are prepared as described for Example 2, substituting preparation 1 with the appropriate bromo starting material (prep.=preparation).

| Example | Bromo Starting Material | Structure | MS [M + H]+ | r.t. HPLC Method |
|---|---|---|---|---|
| 48 | Prep. 10.1 | 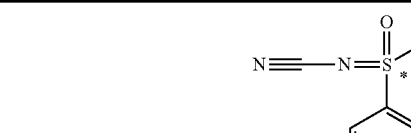 | 570 | 1.03 min Z017_S04 |

-continued
| Example | Bromo Starting Material | Structure | MS [M + H]+ | r.t. HPLC Method |
|---|---|---|---|---|
| 49 | Prep. 10.2 | 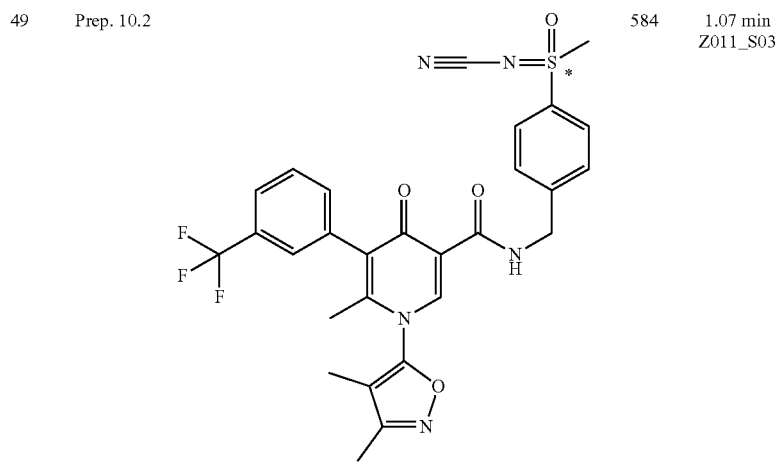 | 584 | 1.07 min Z011_S03 |
| 50 | Prep. 10.3 | 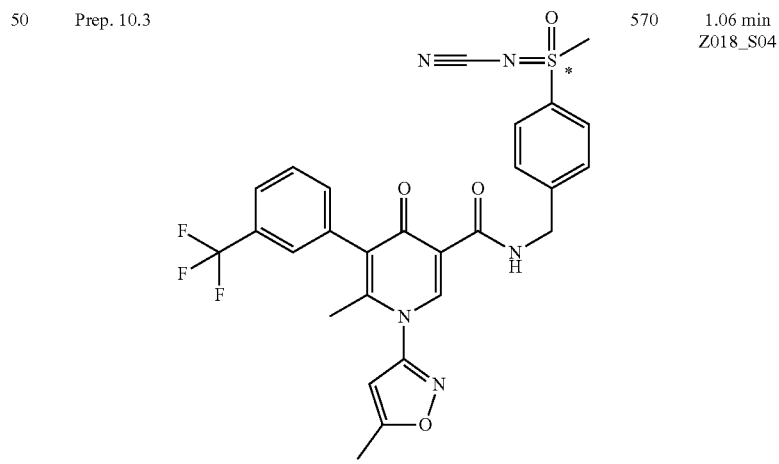 | 570 | 1.06 min Z018_S04 |
| 51 | Prep. 10.4 | 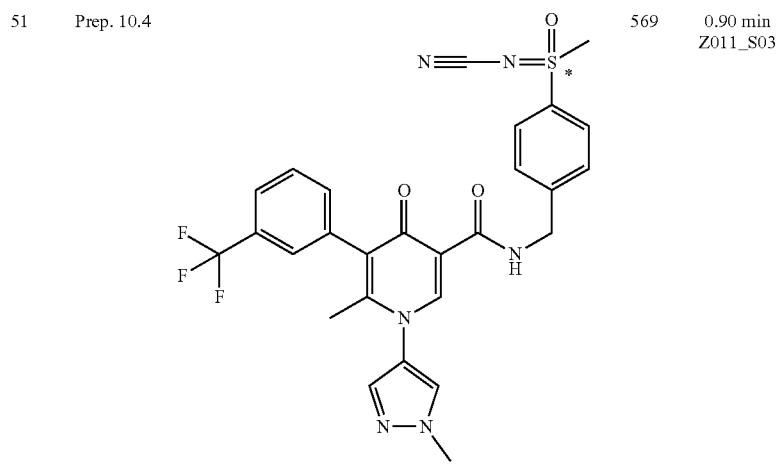 | 569 | 0.90 min Z011_S03 |

-continued
| Example | Bromo Starting Material | Structure | MS [M + H]+ | r.t. HPLC Method |
|---|---|---|---|---|
| 52 | Prep. 10.5 | 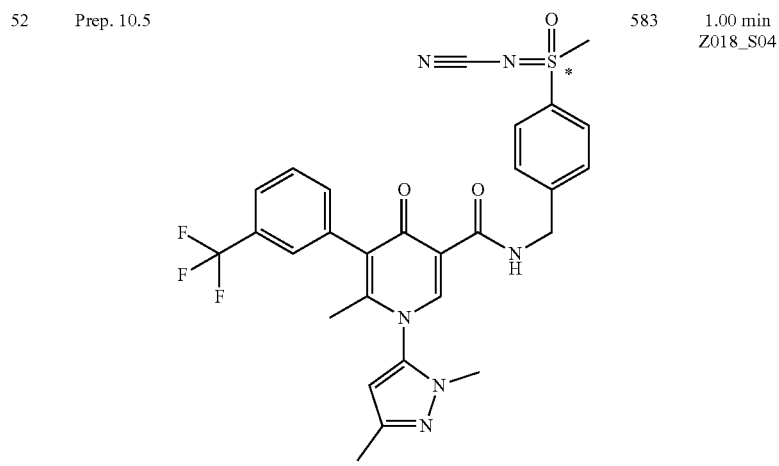 | 583 | 1.00 min Z018_S04 |
| 53 | Prep. 10.6 | 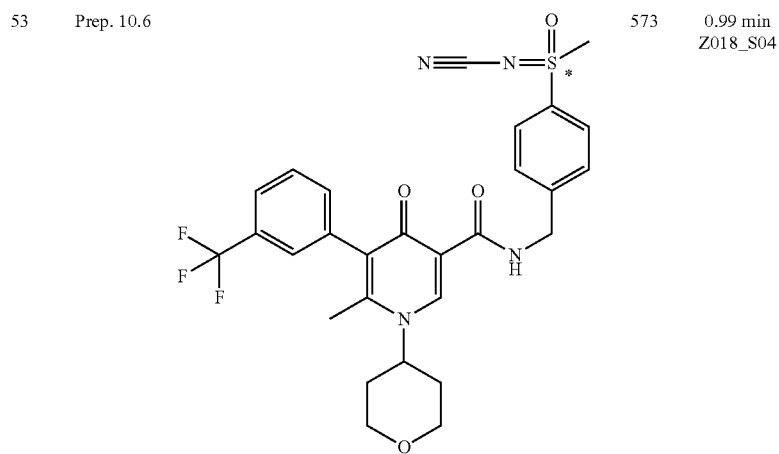 | 573 | 0.99 min Z018_S04 |
| 54 | Prep. 10.7 | 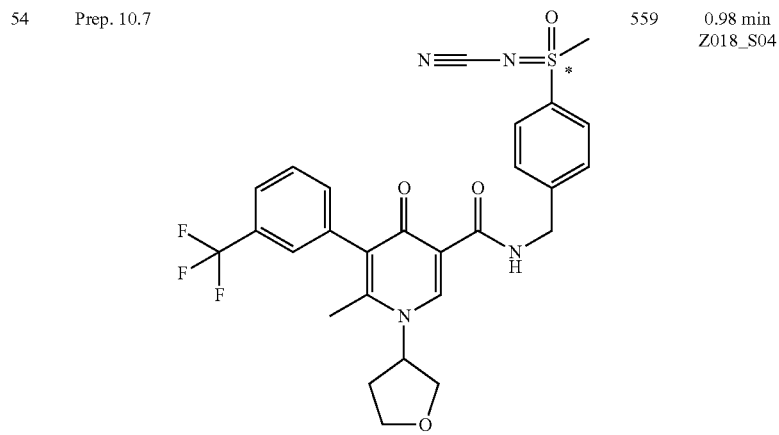 | 559 | 0.98 min Z018_S04 |

-continued
| Example | Bromo Starting Material | Structure | MS [M + H]+ | r.t. HPLC Method |
|---|---|---|---|---|
| 55 | Prep. 10.8 | 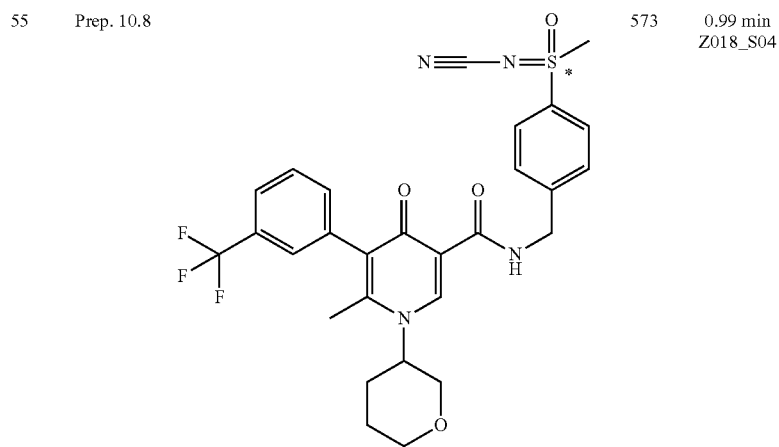 | 573 | 0.99 min Z018_S04 |
| 56 | Prep. 10.9 | 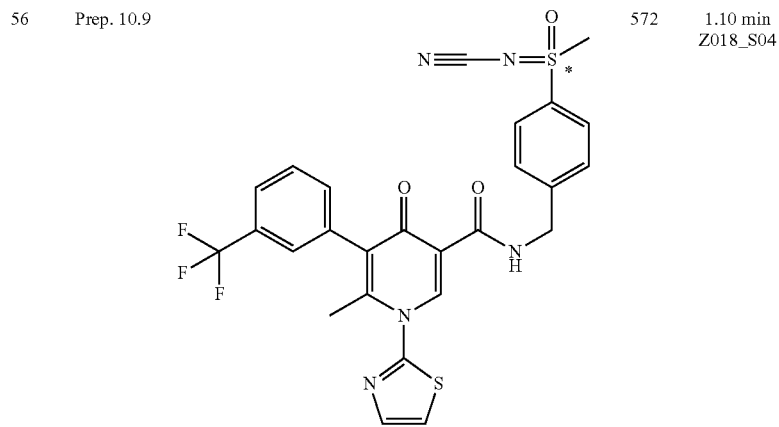 | 572 | 1.10 min Z018_S04 |
| 57 | Prep. 10.10 | 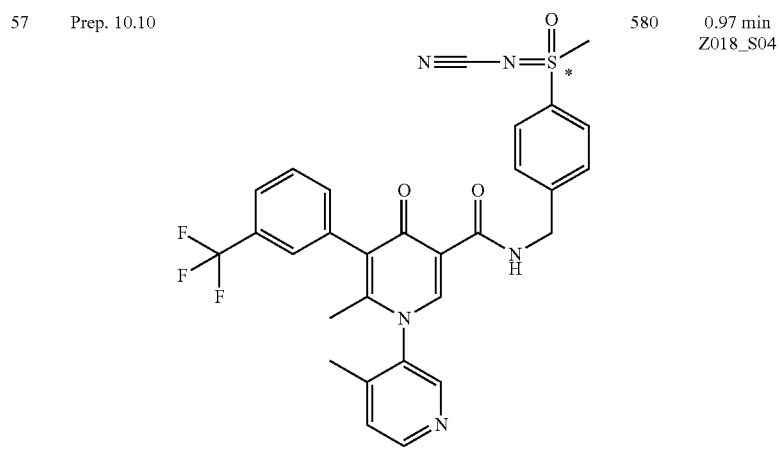 | 580 | 0.97 min Z018_S04 |

-continued

| Example | Bromo Starting Material | Structure | MS [M + H]+ | r.t. HPLC Method |
|---|---|---|---|---|
| 58 | Prep. 10.11 | 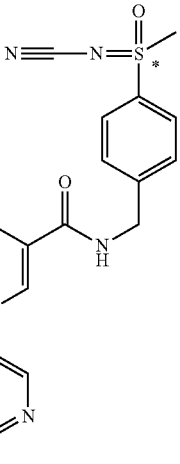 | 580 | 0.98 min Z018_S04 |
| 59 | Prep. 10.12 | 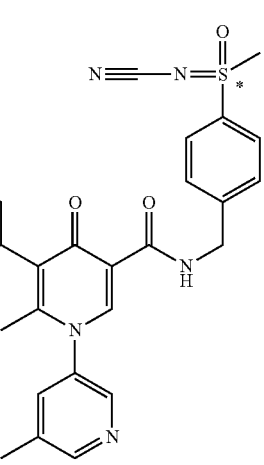 | 580 | 1.00 min Z018_S04 |

Several racemic examples are separated into the respective enantiomers by preparative chiral HPLC as described for the separation of racemic Example 1 into the enantiomers Example 1A and Example 1B, employing HPLC conditions as indicated in the following table.

| Racemic Example | Preparative Chiral HPLC Conditions | Enantiomeric Example | Analytical Chiral HPLC Method | r.t. | MS [M + H]+ |
|---|---|---|---|---|---|
| 10 | Daicel OJ-H 10% MeOH + 0.2% DEA | 10A 10B | Daicel Chiralpak ® OJ-H, 250 mm × 4.6 mm, 4 ml/min, 10 min, 15% MeOH + 0.2% diethylamine in supercritical CO$_2$, 40° C. | 2.33 min 2.53 min | 531 531 |
| 21 | Daicel OJ-H 10% MeOH + 0.2% DEA | 21A 21B | Daicel Chiralpak ® OJ-H, 250 mm × 4.6 mm, 4 ml/min, 10 min, 15% MeOH + 0.2% diethylamine in supercritical CO$_2$, 40° C. | 2.24 min 2.41 min | 543 543 |
| 22 | Daicel AS-H 20% MeOH + 0.2% DEA | 22A 22B | Daicel Chiralpak ® AS-H, 250 mm × 4.6 mm, 4 ml/min, 10 min, 15% MeOH + 0.2% diethylamine in supercritical CO$_2$, 40° C. | 2.05 min 2.35 min | 557 557 |

| Racemic Example | Preparative Chiral HPLC Conditions | Enantiomeric Example | Analytical Chiral HPLC Method | r.t. | MS [M + H]+ |
|---|---|---|---|---|---|
| 29 | Daicel OJ-H 10% MeOH + 0.2% DEA | 29A 29B | Daicel Chiralpak ® OJ-H, 250 mm × 4.6 mm, 4 ml/min, 10 min, 15% MeOH + 0.2% diethylamine in supercritical $CO_2$, 40° C. | 3.48 min 3.91 min | 513 513 |
| 30 | Daicel OZ-H 35% MeOH + 0.2% DEA | 30A 30B | Daicel Chiralpak ® OZ-H, 250 mm × 4.6 mm, 4 ml/min, 10 min, 40% MeOH + 0.2% diethylamine in supercritical $CO_2$, 40° C. | 6.50 min 7.55 min | 527 527 |
| 31 | Daicel OJ-H 10% MeOH + 0.2% DEA | 31A 31B | Daicel Chiralpak ® OJ-H, 250 mm × 4.6 mm, 4 ml/min, 10 min, 15% MeOH + 0.2% diethylamine in supercritical $CO_2$, 40° C. | 2.44 min 2.71 min | 527 527 |
| 5.5 | Daicel OJ-H 10% MeOH + 0.2% DEA | 5.5A 5.5B | Daicel Chiralpak ® OJ-H, 250 mm × 4.6 mm, 4 ml/min, 10 min, 20% MeOH + 0.2% diethylamine in supercritical $CO_2$, 40° C. | 2.36 min 2.65 min | 499 499 |

Example 60

5-(3-Trifluoromethyl-phenyl)-1-isopropyl-6-methyl-4-oxo-1,4-dihydro-pyridine-3-carboxylic acid 4-(N,N,N'-trimethylsulfamimidoyl)-benzylamide

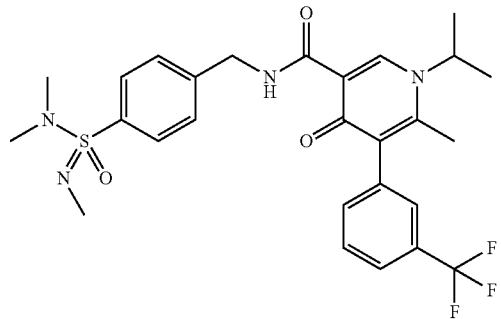 [SMILES: CN=S(=O)(c1ccc(CNC(=O)c2cn(C(C)C)c(C)c(-c3cccc(C(F)(F)F)c3)c2=O)cc1)N(C)C]

60a: Thioacetic acid 4-(1,3-dioxo-1,3-dihydro-isoindol-2-ylmethyl)-phenyl ester

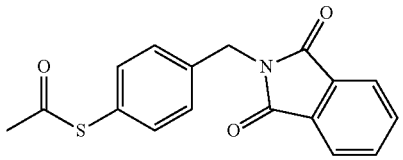 [SMILES: CC(=O)Sc1ccc(CN2C(=O)c3ccccc3C2=O)cc1]

A solution of 2-benzyl-isoindole-1,3-dione (prepared as described in WO07093452, 22.0 g, 92.7 mmol) in dichloromethane (150 mL) is cooled in an ice bath at 0° C. Chlorosulfonic acid (12.3 mL, 185 mmol) is added dropwise and the mixture is allowed to warm to room temperature. After 1.5 h the mixture is cooled at 0° C., and thionyl chloride (10.1 mL, 139 mmol) is added. The mixture is heated at reflux for 3.5 h, and chlorosulfonic acid (3.1 mL, 46 mmol) and thionyl chloride (2.0 mL, 28 mmol) is added. The mixture is stirred at room temperature over night and poured into ice water. The aqueous phase is extracted twice with dichloromethane, and the combined organic phases are concentrated under reduced pressure.

The residue is dissolved in toluene (250 mL), and the mixture is cooled at 0° C. A solution of triphenylphosphine (70.9 g, 270 mmol) in toluene (250 mL) is added dropwise, and the mixture is warmed at room temperature. After 2.5 h water is added and the phases are separated.

The organic layer is concentrated under reduced pressure and the residue is dissolved in DMF (200 mL). Acetic anhydride (29 mL) is added and the mixture is stirred at room temperature for 2 h. The mixture is concentrated under reduced pressure and purified by flash chromatography on silica (gradient cyclohexane to cyclohexane/ethyl acetate 8:2). Yield: 14 g (15% of theory). ESI mass spectrum: [M+H]+=312; r.t. HPLC: 1.36 min (V001_007).

60b: 4-(1,3-Dioxo-1,3-dihydro-isoindol-2-ylmethyl)-benzenesulfinic acid methylamide

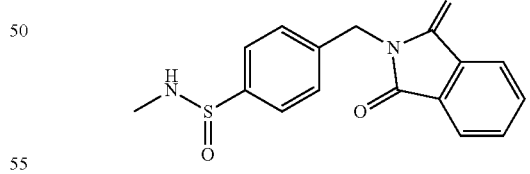

A solution of acetic anhydride (4.34 mL, 45.9 mmol) in dichloromethane (50 mL) is added dropwise to a precooled solution of thioacetic acid 4-(1,3-dioxo-1,3-dihydro-isoindol-2-ylmethyl)-phenyl ester (preparation 60a, 13.0 g, 41.8 mmol) in dichloromethane (500 mL) at −20° C. A solution of sulfuryl chloride (7.4 mL, 91.9 mmol) in dichloromethane (50 mL) is added at this temperature, and the mixture is stirred for 1 h. The mixture is warmed to room temperature, and all volatiles are removed under reduced pressure.

The residue is dissolved in dichloromethane (400 mL), and the solution is cooled in an ice bath at 0° C. Methylamine (2

M in tetrahydrofuran, 84 mL, 168 mmmol) is added dropwise at 0° C., and the mixture is stirred for 2 and then warmed to room temperature. Saturated sodium chloride solution is added, and the mixture is extracted with dichloromethane. The combined organic layers are dried over Na₂SO₄ and concentrated under reduced pressure. Yield: 3.44 g (23% of theory). ESI mass spectrum: [M+H]⁺=315; r.t. HPLC: 0.89 min (X012_S01).

60c: 4-((1,3-Dioxoisoindolin-2-yl)methyl)-N,N,N'-trimethyl-benzene-sulfonimidamide

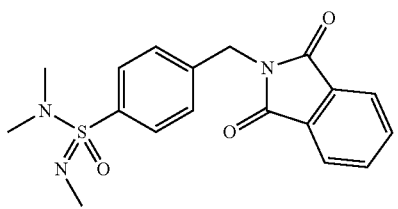 [SMILES: CN=S(=O)(c1ccc(CN2C(=O)c3ccccc3C2=O)cc1)N(C)C]

A mixture of 4-(1,3-dioxo-1,3-dihydro-isoindol-2-ylmethyl)-benzenesulfinic acid methylamide (preparation 60b, 250 mg, 0.795 mmol) in acetonitrile is cooled at 0° C. in an ice bath and treated with tert-butyl hypochlorite (100 µL, 0.88 mmol). After 15 min dimethylamine (2 M in tetrahydrofuran, 600 µL, 1.2 mmol) is added and the mixture is warmed to room temperature. Water is added, and the mixture is extracted twice with dichloromethane. The combined organic layers are dried over Na₂SO₄ and concentrated under reduced pressure. The residue is purified by flash chromatography on silica (gradient cyclohexane/ethyl acetate 7:3 to ethyl acetate). Yield: 284 mg (99% of theory). ESI mass spectrum: [M+H]⁺=358; r.t. HPLC: 0.43 min (X012_S01).

60d: 4-(Aminomethyl)-N,N,N'-trimethylbenzene-sulfonimidamide

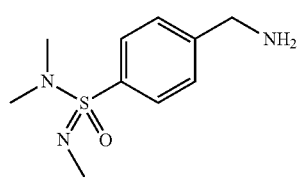

A solution of 4-((1,3-dioxoisoindolin-2-yl)methyl)-N,N,N'-trimethyl-benzene-sulfonimidamide (preparation 60c, 280 mg, 0.78 mmol) in a 2:1:1 mixture of acetonitrile, tetrahydrofuran and ethanol (8 mL) is treated with 1,2-diaminoethane (116 µL, 1.74 mmol). The mixture is heated at 60° C. for 5 h, and another portion of 1,2-diaminoethane (26 µL, 0.39 mmol) is added. After 1.5 h all volatiles are removed under reduced pressure. The residue is treated with dichloromethane, and the mixture is filtered. The filtrate is concentrated under reduced pressure. Yield: 172 mg (97% of theory). ESI mass spectrum: [M+H]⁺=228; r.t. HPLC: 0.66 min (V011_S01).

Example 60

5-(3-Trifluoromethyl-phenyl)-1-isopropyl-6-methyl-4-oxo-1,4-dihydro-pyridine-3-carboxylic acid 4-(N,N,N'-trimethylsulfamimidoyl)-benzylamide

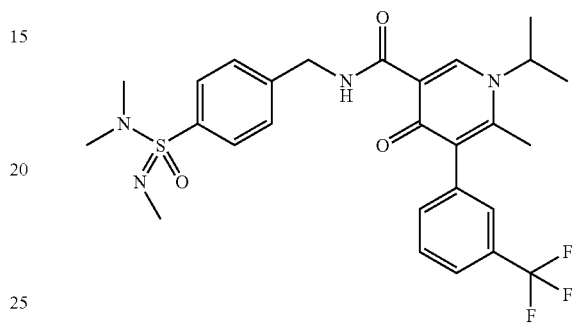

A solution of 1-isopropyl-6-methyl-4-oxo-5-(3-trifluoromethyl-phenyl)-1,4-dihydro-pyridine-3-carboxylic acid (preparation 9.2, 186 mg, 0.55 mmol) in DMF (5 mL) is treated with DIPEA (300 µL, 1.72 mmol) and stirred at room temperature for 10 min. HBTU (312 mg, 0.82 mmol) is added, and the mixture is stirred for 20 min. A solution of 4-(aminomethyl)-N,N,N'-trimethylbenzenesulfonimidamide (preparation 60d, 156 mg, 0.69 mmol) in DMF (0.5 mL) is added and the mixture is stirred for 2 h. Water is added and the mixture is extracted with dichloromethane. The organic layer is dried over Na₂SO₄ and concentrated under reduced pressure. The residue is purified by preparative reversed phase HPLC (Xbridge, gradient of acetonitrile in water, 0.1% TFA). Yield: 41 mg (11% of theory); ESI mass spectrum: [M+H]⁺=549; r.t. HPLC: 1.17 min (Z001_005).

Example 61

5-(3-Difluoromethyl-phenyl)-1-isopropyl-6-methyl-4-oxo-1,4-dihydro-pyridine-3-carboxylic acid 4-(N,N,N'-trimethylsulfamimidoyl)-benzylamide

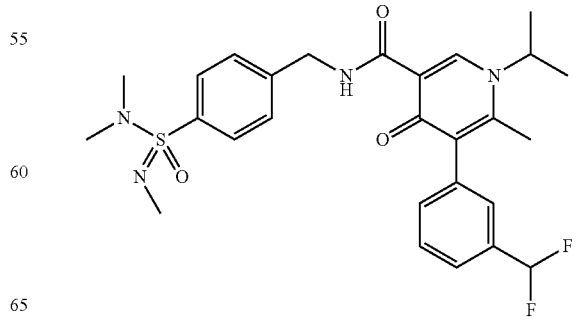

Example 61 is prepared as described for Example 60, substituting preparation 9.2 with preparation 9.12. ESI mass spectrum: [M+H]$^+$=531; r.t. HPLC: 0.86 min (Z011_S03).

Example 62

5-(3-Trifluoromethyl-phenyl)-1-isopropyl-6-methyl-4-oxo-1,4-dihydro-pyridine-3-carboxylic acid (5-(N-cyano-S-methylsulfonimidoyl)-1-oxy-pyridin-2-yl)-methylamide (Pyridine N-oxide of Example 16)

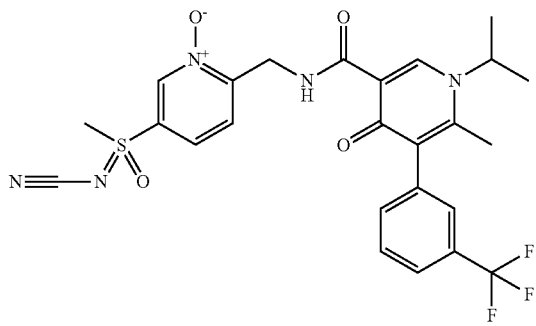 [SMILES: Cc1c(-c2cccc(C(F)(F)F)c2)c(=O)c(C(=O)NCc2ccc(S(C)(=O)=NC#N)c[n+]2[O-])cn1C(C)C]

Meta-chloroperoxybenzoic acid (77%, 8.0 mg, 36 µmol) is added to a solution of 5-(3-trifluoromethyl-phenyl)-1-isopropyl-6-methyl-4-oxo-1,4-dihydro-pyridine-3-carboxylic acid (5-(N-cyano-S-methylsulfonimidoyl)pyridin-2-yl)methylamide (example 16, 17.0 mg, 32 µmol) in dichloromethane (0.5 mL), and the mixture is stirred at room temperature for 2 h. The mixture is heated at reflux and stirred for 2 h. The mixture is cooled at room temperature and stirred over night. A second portion of m-CPBA (77%, 4.3 mg, 19 µmol) is added and the mixture is heated at reflux for 2.5 h. A third portion of m-CPBA (77%, 4.3 mg, 19 µmol) is added and the mixture is stirred at room temperature over night. Saturated aqueous sodium thiosulfate solution is added and the mixture is extracted twice with dichloromethane. The organic layer is dried and concentrated under reduced pressure. The residue is purified by preparative reversed phase HPLC (Xbridge, gradient of acetonitrile in water, 0.1% NH$_3$). Yield: 3.3 mg (19% of theory); ESI mass spectrum: [M+H]$^+$=548; r.t. HPLC: 0.54 min (X011_S03).

Example 63

1-Isopropyl-6-methyl-4-oxo-5-(3-trifluoromethyl-phenyl)-1,4-dihydro-pyridine-3-carboxylic acid 4-(S-cyclopropyl-N-cyanosulfonimidoyl)-benzylamide

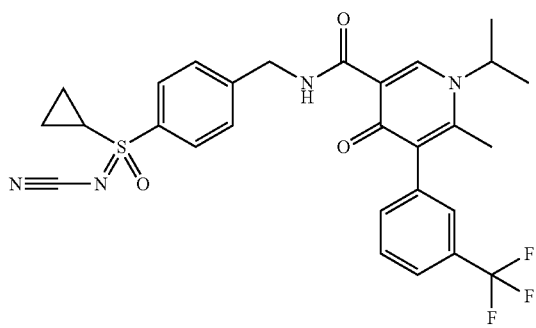 [SMILES: Cc1c(-c2cccc(C(F)(F)F)c2)c(=O)c(C(=O)NCc2ccc(S(=O)(=NC#N)C3CC3)cc2)cn1C(C)C]

63a: 4-Cyclopropylsulfanyl-benzamide

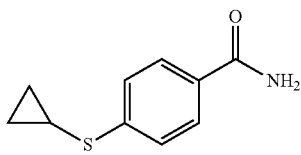 [SMILES: NC(=O)c1ccc(SC2CC2)cc1]

Thionyl chloride (340 µL, 4.7 mmol) is added to a solution of 4-cyclopropylsulfanyl-benzoic acid (prepared as described in WO07003960, 190 mg, 0.98 mmol) in dichloromethane (1.9 mL), and the mixture is heated at reflux for 30 min. All volatiles are removed under reduced pressure, and the residue is dissolved in chloroform (1.9 mL). Concentrated aqueous ammonia (28%, 770 µL, 9.8 mmol) is added and the mixture is stirred at room temperature for 1 h. Water is added and the phases are separated. The organic layer is concentrated under reduced pressure. Yield: 137 mg (72% of theory); ESI mass spectrum: [M+H]$^+$=194; r.t. HPLC: 0.45 min (X011_S03).

64b: 4-Cyclopropylsulfanyl-benzylamine

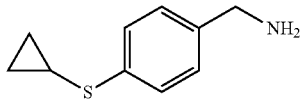 [SMILES: NCc1ccc(SC2CC2)cc1]

A solution of 4-cyclopropylsulfanyl-benzamide (preparation 63a, 137 mg, 0.71 mmol) in THF is added to lithium aluminium hydride (1 M in THF, 2.1 mL, 2.1 mmol) pre-cooled at 0° C. The mixture is stirred at 0° C. for 1 h and then heated at reflux for 1 h. The mixture is cooled to room temperature and stirred for 1.5 h. Water is added, and the mixture is extracted twice with dichloromethane. The combined organic layers are dried over Na$_2$SO$_4$ and concentrated under reduced pressure. Yield: 75 mg (60% of theory); ESI mass spectrum: [M+H]$^+$=180; r.t. HPLC: 0.51 min (X011_S03).

63c: 1-Isopropyl-6-methyl-4-oxo-5-(3-trifluoromethyl-phenyl)-1,4-dihydro-pyridine-3-carboxylic acid 4-cyclopropylsulfanyl-benzylamide

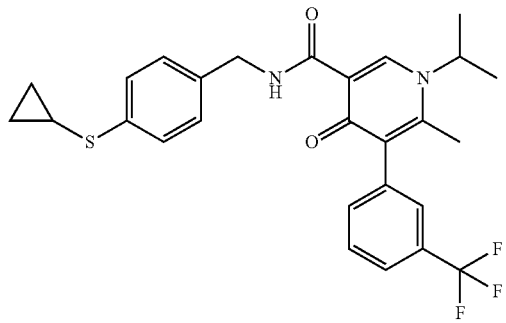 [SMILES: Cc1c(-c2cccc(C(F)(F)F)c2)c(=O)c(C(=O)NCc2ccc(SC3CC3)cc2)cn1C(C)C]

The title compound is prepared following the procedure described for example 60, substituting 4-(aminomethyl)-N,N,N'-trimethylbenzenesulfonimidamide with 4-cyclopropylsulfanyl-benzylamine (preparation 63b), and replacing HBTU with TBTU. ESI mass spectrum: [M+H]$^+$=501; r.t. HPLC: 0.77 min (X012_S01).

63d: 1-Isopropyl-6-methyl-4-oxo-5-(3-trifluoromethyl-phenyl)-1,4-dihydro-pyridine-3-carboxylic acid 4-(S-cyclopropyl-N-cyanosulfinimidoyl)-benzylamide

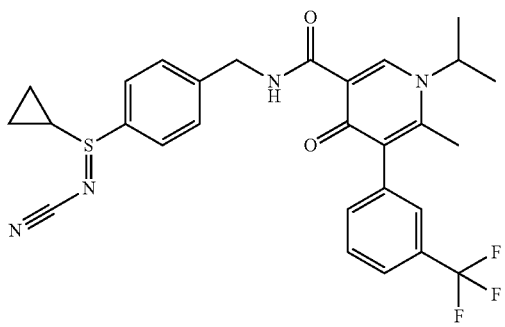 [SMILES: Cc1c(-c2cccc(C(F)(F)F)c2)c(=O)c(C(=O)NCc2ccc(/S(=N/C#N)C3CC3)cc2)cn1C(C)C]

A mixture of 1-isopropyl-6-methyl-4-oxo-5-(3-trifluoromethyl-phenyl)-1,4-dihydro-pyridine-3-carboxylic acid 4-cyclopropylsulfanyl-benzylamide (preparation 63c, 75 mg, 0.15 mmol), cyanamide (8 mg, 0.19 mmol), N-bromosuccinimide (40 mg, 0.22 mmol) and potassium tert-butoxide (20 mg, 0.18 mmol) in methanol (1 mL) is stirred at room temperature for 1 h. Saturated aqueous sodium thiosulfate solution is added, and the mixture is extracted twice with dichloromethane. The organic layer is dried over Na$_2$SO$_4$ and concentrated under reduced pressure. The residue is purified by preparative reversed phase HPLC (Xbridge, gradient of acetonitrile in water, 0.1% NH$_3$). Yield: 7 mg (8% of theory); ESI mass spectrum: [M+H]$^+$=541; r.t. HPLC: 0.64 min (X012_S02).

Example 63

1-Isopropyl-6-methyl-4-oxo-5-(3-trifluoromethyl-phenyl)-1,4-dihydro-pyridine-3-carboxylic acid 4-(S-cyclopropyl-N-cyanosulfonimidoyl)-benzylamide

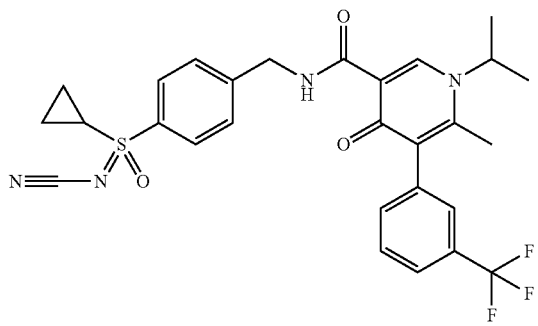 [SMILES: Cc1c(-c2cccc(C(F)(F)F)c2)c(=O)c(C(=O)NCc2ccc(S(=O)(=NC#N)C3CC3)cc2)cn1C(C)C]

A mixture of 1-isopropyl-6-methyl-4-oxo-5-(3-trifluoromethyl-phenyl)-1,4-dihydro-pyridine-3-carboxylic acid 4-(S-cyclopropyl-N-cyanosulfinimidoyl)-benzylamide (preparation 63d, 40 mg, 74 µmol), meta-chloroperoxybenzoic acid (77%, 25 mg, 0.11 mmol) and potassium carbonate (31 mg, 0.22 mmol) in ethanol is stirred at room temperature for 1 h. Another portion of meta-chloroperoxybenzoic acid (77%, 5 mg, ai 0.02 mmol) is added and stirring is continued for 1.5 h. Saturated aqueous sodium thiosulfate solution is added, and the mixture is extracted with dichloromethane. The organic layer is dried over Na$_2$SO$_4$ and concentrated under reduced pressure. The residue is purified by preparative reversed phase HPLC (Xbridge, gradient of acetonitrile in water, 0.1% TFA). Yield: 13 mg (31% of theory); ESI mass spectrum: [M+H]$^+$=557; r.t. HPLC: 0.65 min (X011_S03).

Example 64

1-Isopropyl-6-methyl-4-oxo-5-(3-trifluoromethyl-phenyl)-1,4-dihydro-pyridine-3-carboxylic acid 4-(N-(cyanomethyl)-S-methylsulfonimidoyl)-benzylamide

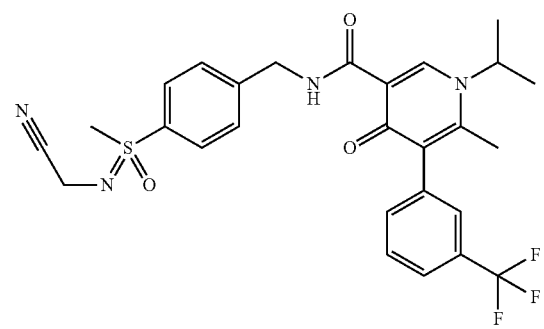 [SMILES: Cc1c(-c2cccc(C(F)(F)F)c2)c(=O)c(C(=O)NCc2ccc(S(C)(=O)=NCC#N)cc2)cn1C(C)C]

64a: 2-(4-(N-Cyanomethyl-S-methylsulfonimidoyl)benzyl)isoindoline-1,3-dione

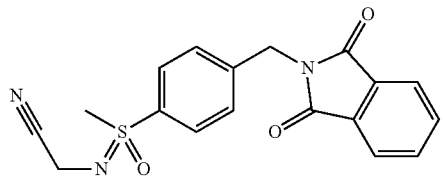 [SMILES: CS(=O)(=NCC#N)c1ccc(CN2C(=O)c3ccccc3C2=O)cc1]

A mixture of 2-(4-(S-methylsulfonimidoyl)benzyl)isoindoline-1,3-dione (preparation 17b, 500 mg, 1.59 mmol) and 1,2-dimethoxyethane (2 mL) is added to a mixture of potassium hydride (30%, 260 mg, 1.95 mmol) in 1,2-dimethoxyethane (3 mL). The mixture is stirred for 15 min at room temperature and treated with tetraethylammonium bromide (10 mg, 0.05 mmol) and bromoacetonitrile (220 µL, 3.16 mmol). The mixture is heated at 110° C. over night and cooled to room temperature. Water is added, and the mixture is extracted twice with dichloromethane. The organic layer is concentrated under reduced pressure, and the residue is purified by flash chromatography on silica (gradient cyclohexane/ ethyl acetate 1:0 to 0:1). Yield: 155 mg (27% of theory). ESI mass spectrum: [M+H]⁺=354; r.t. HPLC: 0.47 min (X011_S03).

64b:
4-(N-cyanomethyl-S-methylsulfonimidoyl)benzylamine

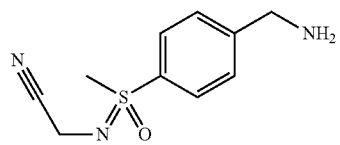

The title compounds is prepared in analogy to preparation 60d, using 2-(4-(N-cyano-methyl-S-methylsulfonimidoyl)benzyl)isoindoline-1,3-dione (preparation 64a) as starting material. ESI mass spectrum: [M+H]⁺=224; r.t. HPLC: 0.22 min (X011_S03).

Example 64

1-Isopropyl-6-methyl-4-oxo-5-(3-trifluoromethyl-phenyl)-1,4-dihydro-pyridine-3-carboxylic acid 4-(N-(cyanomethyl)-S-methylsulfonimidoyl)-benzylamide

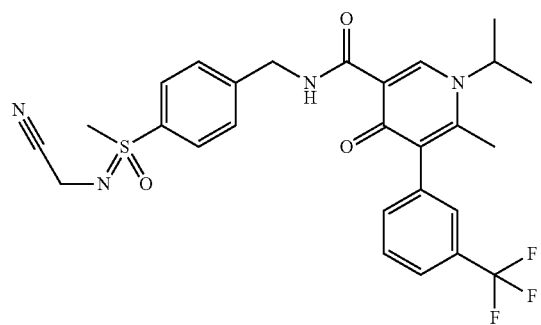 [SMILES: Cc1c(-c2cccc(C(F)(F)F)c2)c(=O)c(C(=O)NCc2ccc(S(C)(=O)=NCC#N)cc2)cn1C(C)C]

The title compound is prepared following the procedure described for example 60, substituting 4-(aminomethyl)-N,N,N'-trimethylbenzenesulfonimidamide with 4-(N-cyano-methyl-S-methylsulfonimidoyl)benzylamine (preparation 64b), and replacing HBTU with TBTU. ESI mass spectrum: [M+H]+=545; r.t. HPLC: 0.59 min (X012_S01).

Example 65

1-Isopropyl-6-methyl-4-oxo-5-(3-trifluoromethyl-phenyl)-1,4-dihydro-pyridine-3-carboxylic acid [1-(4-(N-cyano-S-methylsulfonimidoyl)-phenyl)-ethyl]-amide

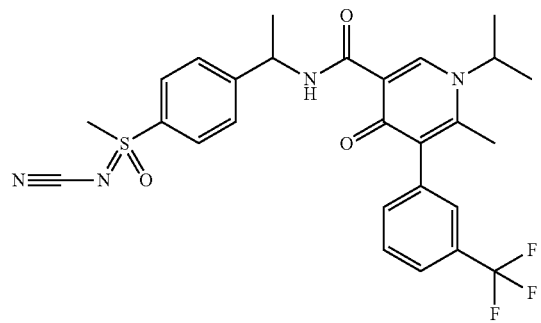 [SMILES: Cc1c(-c2cccc(C(F)(F)F)c2)c(=O)c(C(=O)NC(C)c2ccc(S(C)(=O)=NC#N)cc2)cn1C(C)C]

65a: 1-Isopropyl-6-methyl-4-oxo-5-(3-trifluoromethyl-phenyl)-1,4-dihydro-pyridine-3-carboxylic acid [1-(4-methylsulfanyl-phenyl)-ethyl]-amide

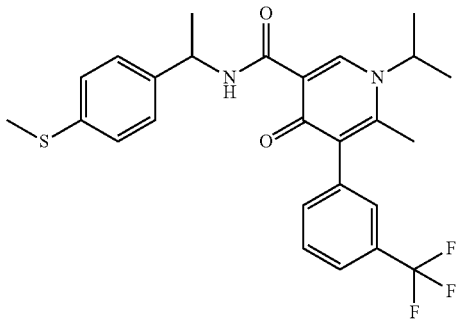 [SMILES: CSc1ccc(C(C)NC(=O)c2cn(C(C)C)c(C)c(-c3cccc(C(F)(F)F)c3)c2=O)cc1]

The title compound is prepared following the procedure described for example 60, substituting 4-(aminomethyl)-N,N,N'-trimethylbenzenesulfonimidamide with 1-(4-methylsulfanyl-phenyl)-ethylamine, and replacing HBTU with TBTU. ESI mass spectrum: [M+H]⁺=489; r.t. HPLC: 0.76 min (X011_S03).

Example 65

1-Isopropyl-6-methyl-4-oxo-5-(3-trifluoromethyl-phenyl)-1,4-dihydro-pyridine-3-carboxylic acid [1-(4-(N-cyano-S-methylsulfonimidoyl)-phenyl)-ethyl]-amide

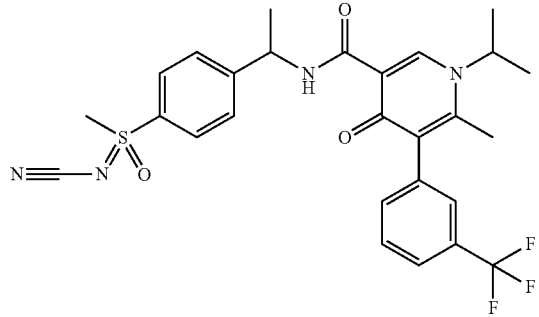 [SMILES: Cc1c(-c2cccc(C(F)(F)F)c2)c(=O)c(C(=O)NC(C)c2ccc(S(C)(=O)=NC#N)cc2)cn1C(C)C]

A mixture of 1-isopropyl-6-methyl-4-oxo-5-(3-trifluoromethyl-phenyl)-1,4-dihydro-pyridine-3-carboxylic acid [1-(4-methylsulfanyl-phenyl)-ethyl]-amide (preparation 65a, 50 mg, 0.10 mmol), cyanamide (6 mg, 0.14 mmol) and potassium tert-butoxide (14 mg, 0.13 mmol) in methanol (0.5 mL) is treated with N-bromosuccinimide (27 mg, 0.15 mmol) and stirred at room temperature for 15 min. Saturated aqueous Na₂S₂O₃ solution is added, and the mixture is extracted with dichloromethane. The organic layer is concentrated under reduced pressure, and the residue is dissolved in ethanol (0.5 mL).

Potassium carbonate (16 mg, 120 µmol) and meta-chloroperoxybenzoic acid (77%, 13 mg, 60 µmol) is added, and the mixture is stirred at room temperature for 1.5 h. Another portion of potassium carbonate (10 mg, 70 µmol) and meta-chloroperoxybenzoic acid (77%, 13 mg, 60 µmol) is added and stirring is continued for 1 h. Saturated aqueous Na₂S₂O₃ solution is added, and the mixture is extracted twice with dichloromethane. The residue is purified by flash chromatography on silica (gradient cyclohexane/ethyl acetate 8:2 to ethyl acetate). Yield: 5 mg (25% of theory); ESI mass spectrum: [M+H]$^+$=545; r.t. HPLC: 0.72 min (Y001_U01).

Example 66

1-Isopropyl-6-methyl-4-oxo-5-(3-trifluoromethyl-phenyl)-1,4-dihydro-pyridine-3-carboxylic acid 3-methyl-4-(N-cyano-S-methylsulfonimidoyl)-benzylamide

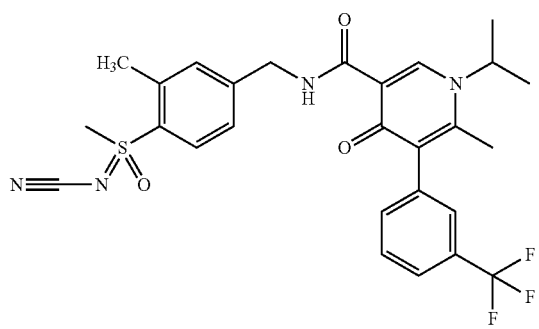 [SMILES: Cc1cc(CNC(=O)c2cn(C(C)C)c(C)c(-c3cccc(C(F)(F)F)c3)c2=O)ccc1S(C)(=O)=NC#N]

66a: 3-Methyl-4-methylsulfanyl-benzonitrile

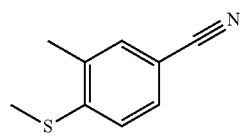

Sodium methanethiolate (1.60 g, 22.8 mmol) is added to a solution of 4-fluoro-3-methyl-benzonitrile (2.50 g, 18.5 mmol) in DMF, and the mixture is heated at 80° C. for 15 min. All volatiles are evaporated, and the residue is treated with water. The mixture is extracted with ethyl acetate twice, and the organic layer is dried over Na$_2$SO$_4$ and concentrated. Yield: 3.0 g (99% of theory); ESI mass spectrum: [M+H]$^+$=164; r.t. HPLC: 0.61 min (X011_S03).

66b: 3-Methyl-4-methylsulfanyl-benzylamine

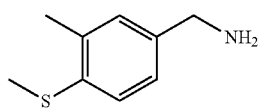

A solution of lithium aluminium hydride (1.0 M in THF, 18.4 mL, 18.4 mmol) is cooled in an ice bath and treated slowly with a solution of 3-methyl-4-methylsulfanyl-benzonitrile (preparation 66a, 1.0 g, 6.1 mmol) in THF (10 mL) while the temperature is kept below 5° C. The mixture is allowed to warm to room temperature and stirred over night. The mixture is cooled again at 0° C., and water (2 mL) and aqueous sodium hydroxide (4 M, 2 mL) is added. The mixture is filtered and the filtrate is extracted twice with dichloromethane. The combined organic layers are concentrated under reduced pressure. Yield: 923 mg (90% of theory); ESI mass spectrum: [M+H–NH$_3$]$^+$=151; r.t. HPLC: 0.61 min (X011_S03).

66c: 1-Isopropyl-6-methyl-4-oxo-5-(3-trifluoromethyl-phenyl)-1,4-dihydro-pyridine-3-carboxylic acid 3-methyl-4-methylsulfanyl-benzylamide

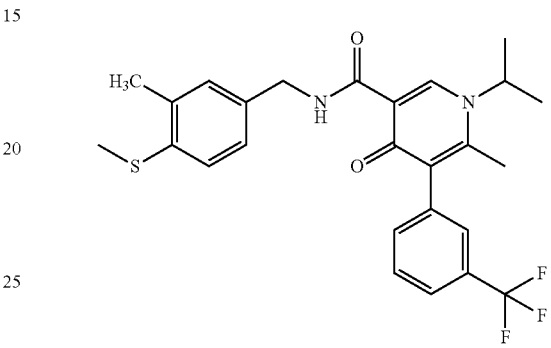

The title compound is prepared following the procedure described for example 60, using 3-methyl-4-methylsulfanyl-benzylamine (preparation 66b) as starting material, and replacing HBTU with TBTU. ESI mass spectrum: [M+H]$^+$=489; r.t. HPLC: 0.77 min (X011_S03).

66d: 1-Isopropyl-6-methyl-4-oxo-5-(3-trifluoromethyl-phenyl)-1,4-dihydro-pyridine-3-carboxylic acid 3-methyl-4-(N-cyano-S-methylsulfinimidoyl)-benzylamide

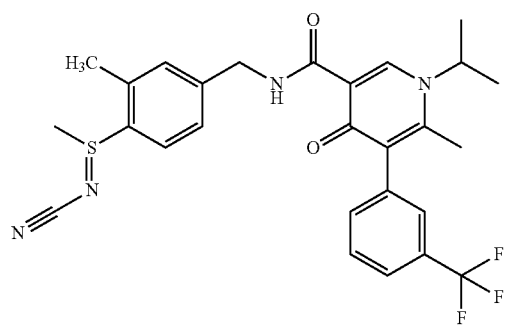 [SMILES: Cc1cc(CNC(=O)c2cn(C(C)C)c(C)c(-c3cccc(C(F)(F)F)c3)c2=O)ccc1/S(C)=N/C#N]

N-Bromosuccinimide (63 mg, 0.35 mmol) is added to a mixture of 1-isopropyl-6-methyl-4-oxo-5-(3-trifluoromethyl-phenyl)-1,4-dihydro-pyridine-3-carboxylic acid 3-methyl-4-methylsulfanyl-benzylamide (preparation 66c, 115 mg, 0.24 mmol), cyanamide (14 mg, 0.33 mmol) and potassium tert-butoxide (32 mg, 0.29 mmol) in methanol (1.1 mL). After 20 min saturated aqueous sodium thiosulfate solution is added, and the mixture is extracted twice with dichloromethane. The combined organic layers is dried over Na$_2$SO$_4$ and concentrated under reduced pressure. The residue is directly used in the next step without further purification. Yield: 99 mg (80% of theory); ESI mass spectrum: [M+H]⁺=529; r.t. HPLC: 0.58 min (X012_S01).

Example 66

1-Isopropyl-6-methyl-4-oxo-5-(3-trifluoromethyl-phenyl)-1,4-dihydro-pyridine-3-carboxylic acid 3-methyl-4-(N-cyano-S-methylsulfonimidoyl)-benzylamide

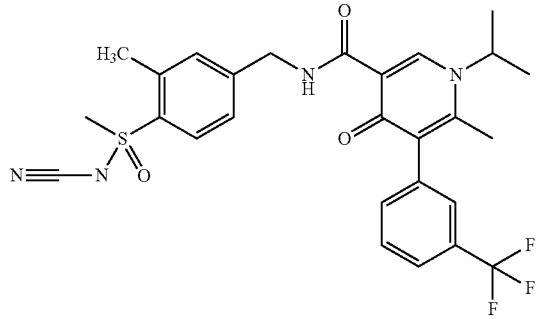

A solution of 1-isopropyl-6-methyl-4-oxo-5-(3-trifluoromethyl-phenyl)-1,4-dihydro-pyridine-3-carboxylic acid 3-methyl-4-(N-cyano-S-methylsulfinimidoyl)-benzylamide (preparation 66d, 25 mg, 47 μmol) and acetic acid (3 μL, 50 μmol) in acetonitrile (0.2 mL) is added to a solution of potassium permanganate (8 mg, 50 μmol) in acetonitrile (0.15 mL) and water (0.15 mL). After 3 h another portion of potassium permanganate (8 mg, 50 μmol) is added and the mixture is heated at reflux. After 2 h saturated aqueous sodium thiosulfate solution is added, and the mixture is extracted twice with dichloromethane. The organic layer is dried over Na₂SO₄ and concentrated under reduced pressure. The residue is purified by preparative reversed phase HPLC (Xbridge, gradient of acetonitrile in water, 0.1% TFA). Yield: 2 mg (8% of theory); ESI mass spectrum: [M+H]⁺=545; r.t. HPLC: 0.61 min (X012_S01).

Example 67

1-Isopropyl-6-methyl-4-oxo-5-(3-trifluoromethyl-phenyl)-1,4-dihydro-pyridine-3-carboxylic acid 4-(N,S-dimethylsulfonimidoyl)-benzylamide

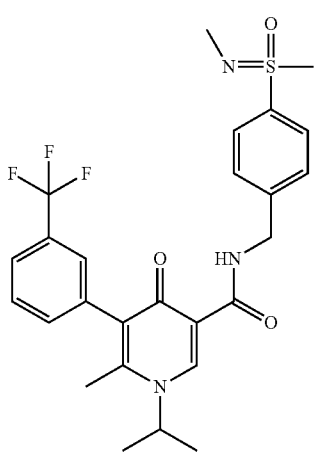 [SMILES: CN=S(C)(=O)c1ccc(CNC(=O)c2cn(C(C)C)c(C)c(-c3cccc(C(F)(F)F)c3)c2=O)cc1]

67a: 2-(4-(N,S-Dimethylsulfonimidoyl)benzyl)isoindoline-1,3-dione

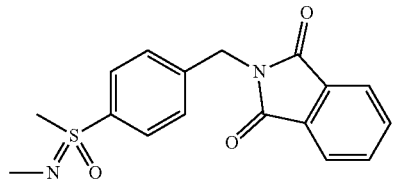 [SMILES: CN=S(C)(=O)c1ccc(CN2C(=O)c3ccccc3C2=O)cc1]

A mixture of 2-(4-(S-methylsulfonimidoyl)benzyl)isoindoline-1,3-dione (preparation 17b, 200 mg, 63.6 mmol) and paraformaldehyde (115 mg, 1.27 mmol) in acetic acid (2 mL) is heated in a microwave at 100° C. for 4 h. The mixture is concentrated under reduced pressure, and the residue is purified by flash chromatography on silica (gradient dichloromethane to dichloromethane/methanol 95:5). Yield: 189 mg (90% of theory); ESI mass spectrum: [M+H]⁺=329; r.t. HPLC: 0.45 min (X011_S03).

67b: 4-(N,S-Dimethylsulfonimidoyl)benzylamine

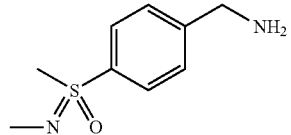

A mixture of 2-(4-(N,S-dimethylsulfonimidoyl)benzyl)isoindoline-1,3-dione (189 mg, 0.58 mmol) and 1,2-diaminoethane (132 μL, 3.44 mmol) in a 2:1:1 mixture of acetonitrile, tetrahydrofuran and ethanol (2 mL) is heated at reflux for 1 h. All volatiles are removed under reduced pressure, and the residue is treated with dichloromethane. The mixture is filtered, and the filtrate is concentrated under reduced pressure. Yield: 114 mg (85% of theory); ESI mass spectrum: [M+H]⁺=199; r.t. HPLC: 0.22 min (X011_S03).

Example 67

1-Isopropyl-6-methyl-4-oxo-5-(3-trifluoromethyl-phenyl)-1,4-dihydro-pyridine-3-carboxylic acid 4-(N,S-dimethylsulfonimidoyl)-benzylamide

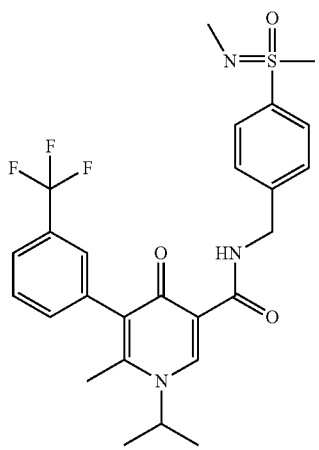 [SMILES: CN=S(C)(=O)c1ccc(CNC(=O)c2cn(C(C)C)c(C)c(-c3cccc(C(F)(F)F)c3)c2=O)cc1]

The title compound is prepared following the procedure described for example 60, substituting 4-(aminomethyl)-N, N,N'-trimethylbenzenesulfonimidamide with 4-(N,S-Dimethylsulfonimidoyl)benzylamine (preparation 67b), and replacing HBTU with TBTU. ESI mass spectrum: [M+H]$^+$=520; r.t. HPLC: 0.58 min (X011_S03).

EXAMPLES

Other features and advantages of the present invention will become apparent from the following more detailed examples which illustrate, by way of example, the principles of the invention.

Human Neutrophil Elastase Assay

Materials: Human neutrophil elastase was purchased from Calbiochem (Cat. No.: 324681) and the elastase substrate MeOSuc-Ala-Ala-Pro-Val-AMC from Bachem (Cat. No.: I-1270). All other materials were of the highest grade commercially available.

The following buffers were used: Compound buffer: 100 mM Tris, 500 mM NaCl, adjusted to pH 7.5; Assay buffer: 100 mM Tris, 500 mM NaCl, adjusted to pH 7.5, containing 0.01% BSA.

Assay conditions: Test compounds were prediluted in DMSO and subsequently in compound buffer (5% DMSO final). 5 µL of these compound dilutions were mixed with 10 µl Neutrophil elastase (9 ng/ml in assay buffer) in a black 384 well OptiPlate (Perkin Elmer, Cat No.: 6007270) and incubated for 15 min at room temperature. Subsequently 10 µL substrate solution in assay buffer were added (250 µM final concentration) and the plates were incubated for 60 min at room temperature. After inactivation of the enzyme, fluorescence intensities were measured at 380 nm excitation and 460 nm emission wavelengths.

Each plate contains wells with a high value control (DMSO+enzyme+substrate) and wells with a low value control (DMSO+inactivated enzyme+substrate). IC50 values were estimated using a sigmoidal concentration response curve with variable slope. Means of low values were taken as 0%, means of high values as 100%. IC50 values of selected compound in the Neutrophil Elastase assay:

| Example | IC50 [nM] |
| --- | --- |
| 1 | 1.3 |
| 1A | 3.1 |
| 1B | 1.3 |
| 2 | 1.7 |
| 2A | 2.3 |
| 2B | 1.1 |
| 3 | 4.7 |
| 3A | 12.0 |
| 3B | 5.1 |
| 4 | 3.0 |
| 4A | 4.1 |
| 4B | 1.6 |
| 5 | 2.5 |
| 6 | 2.4 |
| 7 | 2.1 |
| 8 | 2.4 |
| 9 | <1 |
| 9A | <1 |
| 9B | <1 |
| 10 | 1.2 |
| 10A | 2.7 |
| 10B | 1.2 |
| 5.5A | 5.0 |
| 5.5B | 2.7 |
| 11 | <1 |
| 12 | <1 |
| 13 | 2.4 |
| 14 | 1.5 |
| 15 | 2.2 |
| 16 | 1.9 |
| 17 | 7.3 |
| 18 | 1.5 |
| 19 | 1.0 |
| 20 | 5.6 |
| 21A | 5.2 |
| 21B | 2.1 |
| 22A | 4.5 |
| 22B | 1.2 |
| 23 | 2.6 |
| 24 | 5.5 |
| 25 | 4.3 |
| 26 | 3.3 |
| 27 | 2.5 |
| 28 | 3.3 |
| 29 | 1.5 |
| 29A | 2.2 |
| 29B | <1 |
| 30 | <1 |
| 30A | 1.8 |
| 30B | <1 |
| 31 | <1 |
| 31A | <1 |
| 31B | <1 |
| 32 | 1.1 |
| 33 | 2.5 |
| 34 | 2.4 |
| 35 | 8.0 |
| 36 | 1.0 |
| 37 | <1 |
| 38 | 3.7 |
| 39 | 3.7 |
| 40 | 4.0 |
| 41 | 1.8 |
| 42 | 4.7 |
| 43 | 13.4 |
| 44 | 14.9 |
| 45 | 14.4 |
| 46 | 11.7 |
| 47 | 1.2 |
| 48 | 9.4 |
| 49 | 7.3 |
| 50 | 8.6 |
| 53 | 2.3 |
| 54 | 2.3 |
| 55 | 1.8 |
| 56 | 3.1 |
| 57 | 1.7 |
| 58 | 4.7 |
| 59 | 7.9 |
| 60 | 22.0 |
| 61 | 10.2 |
| 62 | 2.7 |
| 63 | 1.4 |
| 64 | 24.5 |
| 65 | 57.1 |
| 66 | 3.4 |
| 67 | 49.3 |

Combinations

The compounds of general formula I may be used on their own or combined with other active substances of formula I according to the invention. The compounds of general formula I may optionally also be combined with other pharmacologically active substances. These include, β2-adrenoceptor-agonists (short and long-acting), anti-cholinergics (short and long-acting), anti-inflammatory steroids (oral and topical corticosteroids), cromoglycate, methylxanthine, dissociated-glucocorticoidmimetics, PDE3 inhibitors, PDE4-inhibitors, PDE7-inhibitors, LTD4 antagonists, EGFR-inhibitors, Dopamine agonists, PAF antagonists, Lipoxin A4 derivatives, FPRL1 modulators, LTB4-receptor (BLT1, BLT2) antagonists, Histamine H1 receptor antagonists, Histamine H4 receptor antagonists, dual Histamine H1/H3-receptor antagonists, PI3-kinase inhibitors, inhibitors of non-receptor tyrosine kinases as for example LYN, LCK, SYK, ZAP-70, FYN, BTK or ITK, inhibitors of MAP kinases as for example p38, ERK1, ERK2, JNK1, JNK2, JNK3 or SAP, inhibitors of the NF-κB signalling pathway as for example IKK2 kinase inhibitors, iNOS inhibitors, MRP4 inhibitors, leukotriene biosynthese inhibitors as for example 5-Lipoxygenase (5-LO) inhibitors, cPLA2 inhibitors, Leukotriene A4 Hydrolase inhibitors or FLAP inhibitors, MMP9-inhibitors, MMP12-inhibitors Non-steroidale anti-inflammatory agents (NSAIDs), Cathepsin C (or DPPI/Dipeptidyl-aminopeptidase I) inhibitors, CRTH2 antagonists, DP1-receptor modulators, Thromboxane receptor antagonists, CCR3 antagonists, $CCR^4$ antagonists, $CCR^1$ antagonists, CCR5 antagonists, CCR6 antagonists, CCR7 antagonists, CCR8 antagonists, CCR9 antagonists, CCR30 antagonists, $CXCR^3$ antagonists, $CXCR^4$ antagonists, $CXCR^2$ antagonists, $CXCR^1$ antagonists, CXCR5 antagonists, CXCR6 antagonists, $CX3CR^3$ antagonists, Neurokinin (NK1, NK2) antagonists, Sphingosine 1-Phosphate receptor modulators, Sphingosine 1 phosphate lyase inhibitors, Adenosine receptor modulators as for example A2a-agonists, modulators of purinergic receptors as for example P2X7 inhibitors, Histone Deacetylase (HDAC) activators, Bradykinin (BK1, BK2) antagonists, TACE inhibitors, PPAR gamma modulators, Rho-kinase inhibitors, interleukin 1-beta converting enzyme (ICE) inhibitors, Toll-Like receptor (TLR) modulators, HMG-CoA reductase inhibitors, VLA-4 antagonists, ICAM-1 inhibitors, SHIP agonists, GABAa receptor antagonist, ENaC-inhibitors, Prostasin-inhibitors, Melanocortin receptor (MC1R, MC2R, MC3R, MC4R, MC5R) modulators, CGRP antagonists, Endothelin antagonists, TNFα antagonists, anti-TNF antibodies, anti-GM-CSF antibodies, anti-CD46 antibodies, anti-IL-1 antibodies, anti-IL-2 antibodies, anti-IL-4 antibodies, anti-IL-5 antibodies, anti-IL-13 antibodies, anti-IL-4/IL-13 antibodies, anti-TSLP antibodies, anti-OX40 antibodies, mucoregulators, immunotherapeutic agents, compounds against swelling of the airways, compounds against cough, VEGF inhibitors, but also combinations of two or three active substances.

Preferred are betamimetics, anticholinergics, corticosteroids, PDE4-inhibitors, LTD4-antagonists, EGFR-inhibitors, Cathepsin C inhibitors, CRTH2 inhibitors, 5-LO-inhibitors, Histamine receptor antagonists and SYK-inhibitors, especially Cathepsin C inhibitors, but also combinations of two or three active substances, i.e.:

Betamimetics with corticosteroids, PDE4-inhibitors, CRTH2-inhibitors or LTD4-antagonists,
Anticholinergics with betamimetics, corticosteroids, PDE4-inhibitors, CRTH2-inhibitors or LTD4-antagonists,
Corticosteroids with PDE4-inhibitors, CRTH2-inhibitors or LTD4-antagonists
PDE4-inhibitors with CRTH2-inhibitors or LTD4-antagonists
CRTH2-inhibitors with LTD4-antagonists.

Indications

The compounds of the invention and their pharmaceutically acceptable salts have activity as pharmaceuticals, in particular as inhibitors of neutrophil elastase, and thus may be used in the treatment of:

1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; alpha1-antitrypsin deficiency; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus; acute lung injury (ALI) and adult respiratory diseases syndrome (ARDS).

2. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia areata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;

3. eyes: blepharitis; conjunctivitis, including perennial and vernal allergic conjunctivitis; iritis; anterior and posterior uveitis; choroiditis; autoimmune, degenerative or inflammatory disorders affecting the retina; ophthalmitis including sympathetic ophthalmitis; sarcoidosis; infections including viral, fungal, and bacterial;

4. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);

5. allograft rejection: acute and chronic following, for example, transplantation of kidney, heart, liver, lung, bone marrow, skin or cornea or following blood transfusion; or chronic graft versus host disease;

6. other auto-immune and allergic disorders including rheumatoid arthritis, irritable bowel syndrome, systemic lupus erythematosus, multiple sclerosis, Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome and Sazary syndrome;

7. oncology: treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes; and, 8. infectious diseases: virus diseases such as genital warts, common warts, plantar warts, hepatitis B, hepatitis C, herpes simplex virus, molluscum contagiosum, variola, human immunodeficiency virus (HIV), human papilloma virus (HPV), cytomegalovirus (CMV), varicella zoster virus (VZV), rhinovirus, adenovirus, coronavirus, influenza, para-influenza; bacterial diseases such as tuberculosis and *mycobacterium avium*, leprosy; other infectious diseases, such as fungal diseases, chlamydia, *Candida, aspergillus*, cryptococcal meningitis, *Pneumocystis carnii*, cryptosporidiosis, histoplasmosis, toxoplasmosis, trypanosome infection and leishmaniasis.

For treatment of the above-described diseases and conditions, a therapeutically effective dose will generally be in the range from about 0.01 mg to about 100 mg/kg of body weight per dosage of a compound of the invention; preferably, from about 0.1 mg to about 20 mg/kg of body weight per dosage. For Example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

The actual pharmaceutically effective amount or therapeutic dosage will of course depend on factors known by those skilled in the art such as age and weight of the patient, route of administration and severity of disease. In any case the active ingredient will be administered at dosages and in a manner which allows a pharmaceutically effective amount to be delivered based upon patient's unique condition.

What we claim:

1. A compound of formula 1

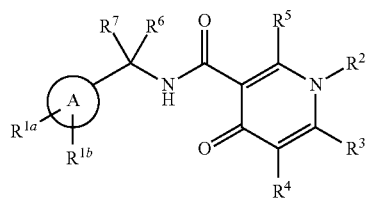

wherein
A is phenyl or pyridinyl;
$R^{1a}$ is

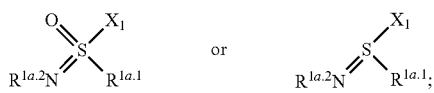

$R^{1a.1}$ is $C_{1-4}$-alkyl-;
$R^{1a.2}$ is NC—;
$R^{1b}$ is H;
$R^2$ is $C_{1-6}$-alkyl or a residue selected from the group consisting of $C_{3-6}$-cycloalkyl-, phenyl-$C_{1-4}$-alkyl- and a five- or six-membered, aromatic heteroring containing one or two nitrogen atoms, each of the above rings optionally substituted with $C_{1-4}$-alkyl-, halogen or NC—;
$R^3$ is methyl;
$R^4$ is phenyl, a five- or six-membered, aromatic ring containing one or two nitrogen atom, each ring optionally substituted with one or two residues selected independently from each other from the group consisting of $C_{1-4}$-alkyl-, halogen or $C_{1-4}$-haloalkyl-;

$R^5$ is H;
$R^6$ is H;
$R^7$ is H;
or a pharmaceutically acceptable salt thereof.

2. A compound of formula 1, according to claim 1, wherein
A is phenyl or pyridinyl;
$R^{1a}$ is

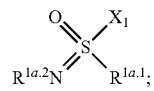

$R^{1a.1}$ is $C_{1-4}$-alkyl-;
$R^{1a.2}$ is NC—;
$R^{1b}$ is H;
$R^2$ is $C_{1-6}$-alkyl or a residue selected from the group consisting of $C_{3-6}$-cycloalkyl-, phenyl-$C_{1-4}$-alkyl- and a five-membered, aromatic ring containing two nitrogen atoms; each optionally substituted with methyl or NC—;
$R^3$ is methyl;
$R^4$ is phenyl or a six-membered, aromatic heteroring containing one or two nitrogen atom, each ring substituted with one or two residues selected independently from each other from the group consisting of $C_{1-4}$-alkyl-, halogen or $C_{1-4}$-haloalkyl-;
$R^5$ is H;
$R^6$ is H;
$R^7$ is H;
or a pharmaceutically acceptable salt thereof.

3. A compound of formula 1, according to claim 1, wherein
A is phenyl or pyridinyl;
$R^{1a}$ is

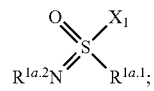

$R^{1a.1}$ is methyl, ethyl, i-propyl, n-propyl;
$R^{1a.2}$ is NC—;
$R^{1b}$ is H;
$R^2$ is ethyl, i-propyl, 2-butyl, cyclobutyl, 1-methylpyrazolyl, or benzyl or 4-NC-benzyl;
$R^3$ is methyl;
$R^4$ is phenyl or pyridinyl, each ring substituted with one or two residues selected independently from each other from the group consisting of methyl, ethyl, propyl, F, Br, Cl, $F_2HC-$ or $F_3C-$;
$R^5$ is H;
$R^6$ is H;
$R^7$ is H;
or a pharmaceutically acceptable salt thereof.

4. A compound of formula 1, according to claim 1, wherein
A is phenyl;
$R^{1a}$ is

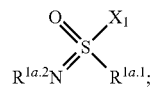

$R^{1a.1}$ is methyl;
$R^{1a.2}$ is NC—;
$R^{1b}$ is H;
$R^2$ is ethyl, i-propyl, cyclobutyl, 1-methylpyrazolyl, benzyl or 4-NC-benzyl;
$R^3$ is methyl;
$R^4$ is phenyl or pyridinyl, each ring substituted with one or two residues selected independently from each other from the group consisting of F, $F_2HC$— or $F_3C$—;
$R^5$ is H;
$R^6$ is H;
$R^7$ is H;
or a pharmaceutically acceptable salt thereof.

5. A compound of formula 1, according to claim 1, wherein
A is phenyl;
$R^{1a}$ is

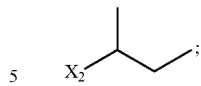

$R^{1a.1}$ is methyl;
$R^{1a.2}$ is NC—;
$R^{1b}$ is H;
$R^2$ is selected from a group consisting of

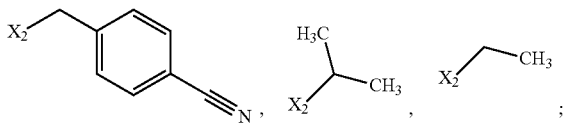

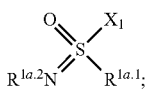 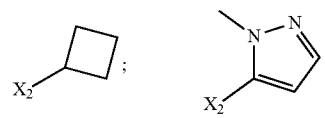

$R^3$ is methyl;
$R^4$ is selected from a group consisting of

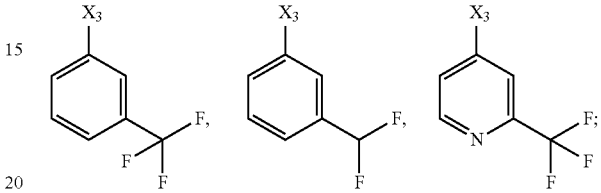

$R^5$ is H;
$R^6$ is H;
$R^7$ is H;
or a pharmaceutically acceptable salt thereof.

6. A pharmaceutical composition comprising a compound of formula 1 according to claim 1 or a pharmaceutically active salt thereof and a pharmaceutically acceptable carrier.

* * * * *